(12) United States Patent
Kim et al.

(10) Patent No.: US 8,492,343 B2
(45) Date of Patent: Jul. 23, 2013

(54) PROTEIN SCAFFOLD LIBRARY BASED ON KRINGLE DOMAIN STRUCTURE AND USES THEREOF

(75) Inventors: Yong-Sung Kim, Suwon-si (KR); Myung-Hee Kwon, Suwon-si (KR); Chang-Han Lee, Gimcheon-si (KR)

(73) Assignee: Ajou University Industry-Academic Cooperation Foundation, Suwon-Si, Gyeonggi-Do (KR)

( * ) Notice: Subject to any disclaimer, the term of this patent is extended or adjusted under 35 U.S.C. 154(b) by 85 days.

(21) Appl. No.: 13/058,810

(22) PCT Filed: Aug. 7, 2009

(86) PCT No.: PCT/KR2009/004423
§ 371 (c)(1),
(2), (4) Date: Feb. 11, 2011

(87) PCT Pub. No.: WO2010/018950
PCT Pub. Date: Feb. 18, 2010

(65) Prior Publication Data
US 2012/0021993 A1    Jan. 26, 2012

(30) Foreign Application Priority Data
Aug. 11, 2008   (KR) .................. 10-2008-0078475

(51) Int. Cl.
*A61K 38/00* (2006.01)
*A61P 35/00* (2006.01)
*C12Q 1/68* (2006.01)
*C12N 15/74* (2006.01)
*C12N 1/20* (2006.01)

(52) U.S. Cl.
USPC ......... 514/19.3; 435/6.1; 435/472; 435/252.3

(58) Field of Classification Search
None
See application file for complete search history.

(56) References Cited

U.S. PATENT DOCUMENTS
2007/0212703 A1* 9/2007 Stemmer et al. .................. 435/6

FOREIGN PATENT DOCUMENTS
WO          02/088171 A2   11/2002
WO    WO 2005016281 A2 *  2/2005

OTHER PUBLICATIONS

Salinas et al., J Tissue Eng Regen Med, 2008; 2: 296-304, published online on May 30, 2008.*
Castellino, et al., "The Kringle Domains of Human Plasminogen", Novartis Foundation Symposium 212—Plasminogen-Related Growth Factors, Sep. 28, 2007, John Wiley & Sons, Ltd., Chichester, UK, XP55023077, ISBN: 978-0-47-197456-7, pp. 46-65.
Chang, et al., "Structure and Ligand Binding Determinants of the Recombinant Kringle 5 Domain of Human Plasminogen", Biochemistry, Mar. 1, 1998, vol. 37, No. 10, pp. 3258-3271.
Binz, et al., "Engineering Novel Binding Proteins from Nonimmunoglobulin Domains", Nature Biotechnology, Oct. 1, 2005, vol. 23, No. 10, pp. 1257-1268.
European Search Report dated May 8, 2012, for European Application No. 09 80 6812.5—10 pages.
Cao, Yihai et al., Kringle Structures and Antiangiogenesis, Curr Med Chem—Anti-Cancer Agents, 2:667-681, 2002.
Castellino, Francis J. et al., The Genetic Relationships between the Kringle Domains of Human Plasminogen, Prothrombin, Tissue Plasminogen Activator, Urokinase, and Coagulation Factor XII, Journal of Molecular Evolution, 26:358-369, 1987.
Hey, Thomas et al., Artificial, non-antibody binding proteins for pharmaceutical and industrial applications, Trends in Biotechnology, 23(10): 514-522, 2005.
Hulo, Nicolas et al. The 20 years of PROSITE, Nucleic Acids Research, 36:D245-249, 2008.
Ikeo, Kazuho et al., Different Evolutionary Histories of Kringle and Protease Domains in Serine Proteases: A Typical Example of Domain Evolution, Journal of Molecular Evolution, 40:331-336, 1995.
Klose, Regina et al., Mapping of a Minimal Apolipoprotein(a) Interaction Motif Conserved in Fibrin(ogen) Beta- and Gamma-Chains, The Journal of Biological Chemistry, vol. 275(49):38206-38212, Dec. 8, 2000.
Letunic, Ivica et al., SMART 5: domains in the context of genomes and networks, Nucleic Acids Research, 34: D257-D260, 2006.
Marti, Daniel N. et al., Solution Structure and Dynamics of the Plasminogen Kringle 2-AMCHA Complex: 31-Helix in Homologous Domains, Biochemistry, 38:15741-15755, 1999.
Nakamura, Takahiro et al., Molecular cloning and characterization of Kremen, a novel kringle-containing transmembrane protein, Biochimica et Biophysica Acta, 1518:63-72, 2001.

(Continued)

Primary Examiner — Marcela M Cordero Garcia
Assistant Examiner — Kaipeen Yang
(74) *Attorney, Agent, or Firm* — Knobbe, Martens, Olson & Bear, LLP

(57) ABSTRACT

There are provided a Kringle domain structure, comprising: inducing artificial mutations at amino acid residues except for conserved amino acid residues that are important to maintain the structural scaffold of a Kringle domain; and protein scaffold variants, based on the Kringle domain structure, which modulate the biological activities of a variety of target molecules derived from the protein scaffold library by specifically binding to the target molecules. Also, there is provided a method for constructing homo-/hetero-oligomers which allow multi-specificity binding to multiple targets by the tandem assembly monomeric Kringle domain variants using a linker. Additionally, there is provided a method for preparing multispecific monomers and multivalent monomers by grafting target-binding loops of a Kringle domain variant into non-binding loops of another Kringle domain variant with the same or different target binding specificity. Furthermore, a protein scaffold variant based on the Kringle domain structure that specifically binds to target molecules, DNA encoding the protein scaffold variant, or a method and composition for prevention, detection, diagnosis, treatment or relieving diseases or disorders, particularly cancers and other immune-related diseases, comprising: administering an effective amount of the related molecule to animals, preferably human.

13 Claims, 43 Drawing Sheets

OTHER PUBLICATIONS

Nygren, Per-Ake et al., Binding proteins from alternative scaffolds, Journal of Immunological Methods, 290:3-28, 2004.

Rice, Glenn C. et al., Random PCR mutagenesis screening of secreted proteins by direct expression in mammalian cells, Proc. Natl. Acad Sci., 89:5467-5471, Jun. 1992.

Skerra, Arne, Alternative non-antibody scaffolds for molecular recognition, Current Opinion in Biotechnology, 18:295-304, 2007.

Skerra, Arne, Alternative binding proteins: Anticalins—harnessing the structural plasticity of the lipocalin ligand pocket to engineer novel binding activities, The FEBS Journal, 275:2677-2683, 2008.

Yoshimura, Teizo et al., Cloning Sequencing, and Expression of Human Macrophage Stimulating Protein (MSP, MST1) Confirms MSP as a Member of the Family of Kringle Proteins and Locates the MSP Gene on Chromosome 3, The Journal of Biological Chemistry, 268(21):15461-15468, 1993.

International Search Report and Written Opinion dated Mar. 16, 2010, for International Application No. PCT/KR2009/004423.

Rios-Steiner, et al., "Structure and Binding Determinants of the Recombinant Kringle-2 Domain of Human Plasminogen to an Internal Peptide From a Group A Streptococcal Surface Protein", J. Mol. Biol. (2001) 308, 705-719.

* cited by examiner

FIG. 1

| | protein size |
|---|---|
| 1. | marker |
| 2. | KD404 |
| 3. | KD408 |
| 4. | KD409 |
| 5. | KD413 |
| 6. | KD415 |
| 7. | KD421 |
| 8. | KD437 |
| 9. | KD445 |
| 10. | KD456 |
| 11. | KD459 |

| | protein size |
|---|---|
| 1. | marker |
| 2. | KD404 |
| 3. | KD408 |
| 4. | KD409 |
| 5. | KD413 |
| 6. | KD415 |
| 7. | KD421 |
| 8. | KD437 |
| 9. | KD445 |
| 10. | KD456 |
| 11. | KD459 |

| | protein size |
|---|---|
| 1. | marker |
| 2. | KD502 |
| 3. | KD503 |
| 4. | KD504 |
| 5. | KD506 |
| 6. | KD509 |
| 7. | KD537 |
| 8. | KD542 |
| 9. | KD548 |
| 10. | KD555 |
| 11. | KD559 |

| | protein size |
|---|---|
| 1. | marker |
| 2. | KD502 |
| 3. | KD503 |
| 4. | KD504 |
| 5. | KD506 |
| 6. | KD509 |
| 7. | KD537 |
| 8. | KD542 |
| 9. | KD548 |
| 10. | KD555 |
| 11. | KD559 |

| kDa | 1 2 3 4 5 | protein size |
|---|---|---|
| 175- | | 1. marker |
| 80- | | 2. KDT01 |
| 58- | | 3. KDT02 |
| 46- | | 4. KDT08 |
| 30- | | 5. KDT26 |
| 25- | | |
| 17- | | |
| 7- | | |

| kDa | 1 2 3 4 5 | protein size |
|---|---|---|
| 175- | | 1. marker |
| 80- | | 2. KDT01 |
| 58- | | 3. KDT02 |
| 46- | | 4. KDT08 |
| 30- | | 5. KDT26 |
| 25- | | |
| 17- | | |
| 7- | | |

Affinity of the selected KR clones against DR4

Affinity of the selected clones agaisnt DR5

Affinity of the selected KR clones against TNF-α

Heterodimer

PROTEIN SCAFFOLD LIBRARY BASED ON KRINGLE DOMAIN STRUCTURE AND USES THEREOF

TECHNICAL FIELD

The present invention relates to a method for constructing a protein scaffold library based on the Kringle domain structure, protein scaffold variants from the Kringle domain library, which bind to various targeted molecules to modulate their biological activities, a method for constructing homo-/hetero-oligomers which allow multi-specificity binding to multiple targets by the tandem assembly monomeric Kringle domain variants. Additionally, the present invention relates to a method for preparing multispecific monomers and multivalent monomers by grafting target-binding loops of a Kringle domain variant into other non-binding loops of another Kringle domain variant with the same or different target binding specificity. Further the present invention provides a method and a composition of Kringle domain variants for prevention, detection, diagnosis, treatment or relieving of diseases or disorders, particularly cancers and other immune-related diseases, and administering an effective amount of Kringle domain variants to animals.

BACKGROUND ART

From the analysis of amino acid sequences and secondary and tertiary structures of proteins, a large number of the proteins are composed of separate domains (or modules). For the proteins, a domain is referred to a separate functional and/or structural unit. At least one identical domain may be distributed in various proteins, and one protein may be composed of various different domains. Specific information of the domain may be searched on web sites for bioinformatics, such as Prosite (Hulo N., et al., Nucleic Acids Res, 36:D245-249, 2008; Website: http://kr.expasy.org/prosite/), SMART (Letunic I., et al., Nucleic Acids Res., 34:D257-D260, 2006; Website: http://smart.embl-heidelberg.de/), and representative examples of the domain include immunoglobulin-like, fibronectin II and III, Kringle, etc.

Interactions between biomolecules (for example, protein-protein, protein-nucleic acid interactions) play important roles in various life phenomena such as growth, differentiation and development of cells, intercellular/intracellular signal transductions, and mass transport. As known molecules that specifically bind to target molecules to control the biological activities of the target molecules, antibodies (full-length antibodies or their fragments) have been under leading development. However, the antibodies have various problems in that they are purely expressed and low in solubility, they should be expressed in an animal cell-expressing cell line, the purification costs are very expensive, and their stabilities are very low in the reducing intracellular environment. In order to solve the above problems, there have been attempts to develop proteins, other than the antibodies, that specifically bind to target molecules, such as antibodies, while solving the problems regarding the antibodies (Review Article: Hey, et al., Trends in Biotech. 23:514-522, 2005; Skerra, Current Opin. Biotech., 18:295-304, 2007). These proteins are referred to as protein scaffold, alternative protein scaffold, alternative scaffold, non-antibody protein scaffold, or alternative binding proteins (hereinafter, as referred to as 'protein scaffold') (Skerra A, FEBS J, 275:2677-2683, 2008; Skerra, Current Opin. Biotech., 18:295-304, 2007; Nygren P., et al., J. Immunol. Method, 290:3-28, 2004). A model protein scaffold is prepared by constructing a protein library by inducing random or designed mutagenesis at residues or loop structures of a protein exposed from a surface thereof while conserving an amino acid sequence that gives the structural stability in order to maintain its structural scaffold, and separating a variant that specifically binds to a target molecule.

Kringle domains occur as separate modules in proteins of various species including human, and several tens or hundreds Kringle domains are present in one protein (see Table 1) (Castellino, et al., J Mol Evol, 26:358-369, 1987; Ikeo, et al., J Mol Evol, 40:331-336, 1995; Cao, et al., Curr Med Chem-Anti-Cancer agents, 2:667-681, 2002). For a variety of living organisms existing in the nature, 1663 different kinds of Kringle domains have been founded from 893 proteins, and 39 Kringle domains whose amino acid sequences are different from each other are distributed in 31 human proteins (See: Prosite (Hulo N., et al., Nucleic Acids Res, 36:D245-249, 2008; Website: http://kr.expasy.org/prosite/; SMART (Letunic I., et al., Nucleic Acids Res, 34:D257-D260, 2006; Website: http://smart.embl-heidelberg.de/) (Castellino, et al., J Mol Evol, 26:358-369, 1987; Ikeo, et al., J Mol Evol, 40:331-336, 1995). A loop (inter-Kringle domain) including approximately 20 amino acids is present between the Kringle domains. The exact functions of the Kringle domains are not known, but the Kringle domains play a role in binding to various biomolecules (for example, proteins, peptides, carbohydrates, cell membranes, phospholipids and the like) to give the binding activity to corresponding proteins and controlling various biological activities of the corresponding proteins (Cao, et al., Curr Med Chem-Anti-Cancer agents, 2:667-681, 2002). Kringle domains are typically distributed in growth factors, proteases, blood coagulation factors, transmembrane receptors, and the like (Castellino, et al., J Mol Evol, 26:358-369, 1987). In particular, the Kringle domains are present independently from the other proteins, or present with the other proteins (for example, endostatin, angiostatin), and also serve to inhibit angiogenesis (antiangiogenesis). Angiostatin has 4 Kringle domains, and this structure of the angiostatin is necessarily used to inhibit angiogenesis (Cao, et al., Curr Med Chem-Anti-Cancer agents, 2:667-681, 2002). Lysine binding sites of Kringle domains in plasminogen and plasmin, which are associated with the fibrinolysis, have been known to be binding sites between extracellular matrix molecules of the two proteins and cell receptors, and thus the lysine binding sites of the Kringle domain has been considered to be important for the fibrinolysis that is the function of the two proteins (Cao, et al., Curr Med Chem-Anti-Cancer agents, 2:667-681, 2002).

TABLE 1

| Protein names | No. of Kringle domains |
|---|---|
| Prothrombin | 2 |
| Plasminogen | 5 |
| Urokinase-type plasminogen activator (uPa) | 1 |
| Tissue-type plasminogen activator (tPa) | 2 |
| Blood coagulation factor XII (Hagenman factor) | 1 |
| Apolipoprotein A | 38 |
| Hepatocyte growth factor/Scatter Factor (HGF/SF) | 4 |
| Macrophage-stimulating protein (MSP)/HGF like protein | 4 |
| HGF activator | 1 |
| Kremen | 1 |
| Neurotrypsin/Motopsin | 1 |
| Plasma hyaluronan binding protein (PHBP) | 1 |
| Serine protease (*Hermandid momus*) | 1 |
| ROR 1&2 | 1 |

TABLE 1-continued

| Protein names | No. of Kringle domains |
|---|---|
| *Drosophila* neurospecific receptor kinase | 1 |
| *Drosophila* receptor kinase | 1 |
| *C. elegans* ROR receptor tyrosin kinase | 1 |
| Muscle specific tyrosin kinase (Musk) (*Torpedo, Xenopus*) | 1 |

Proteins including Kringle domains, and the number of Kringle domains in the proteins are listed in Table 1.

Kringle is a domain or module that has an independent tertiary structure at a variety of proteins in various living organisms, such as humans. A typical Kringle domain is composed of approximately 80 amino acids, and has a tertiary structure connected with 3 disulfide bonds (S—S bond), which provides structurally strong loop structures (Castellino, et al., J Mol Evol, 26:358-369, 1987; Ikeo, et al., J Mol Evol, 40:331-336, 1995; Castellino, et al., Ciba Found Symp, 212:46-60, 1997; Marti, et al., Biochemistry, 38:15741-15755, 1999). The typical Kringle domain has three 1-6, 2-4 and 3-5 disulfide bonding patterns. That is, the disulfide bonding patterns are formed between cysteines 1 and 80, between cysteines 22 and 63, and between cysteines 51 and 75 (Ikeo, et al., J Mol Evol, 40:331-336, 1995; Castellino, et al., Ciba Found Symp, 212:46-60, 1997; Marti, et al., Biochemistry, 38:15741-15755, 1999).

Kringle domains have been found in more than 893 proteins (at least 31 human proteins) from the living organisms living in the nature. In the case of the Kringle domains, some of their amino acids that give the structural stability were conserved, but the other amino acids were not conserved at an amino acid or nucleotide level. Accordingly, it is necessary to construct a variant library by conserving an amino acid sequence of the Kringle domain, which gives the typical structural characteristics, to form a structural scaffold (for example, 3 intracellular disulfide bonds (with 1-6, 2-4 and 3-5 disulfide bonding patterns) and thus a prepared loop structure) and introducing designed or random mutations into structurally flexible regions of the loop structures to have various combinations of amino acid sequences that do not exist in the nature, and also to characterize the variants based on the Kringle domain structural scaffold, which specifically bind to a variety of target molecules from the designed library, by separating and identifying the variants. Also, since the Kringle domain structure-based variants control the biological activities of the target molecules, they may be used to develop methods and compositions for prevention, detection, diagnosis, treatment and relieving of various diseases.

DISCLOSURE OF INVENTION

Technical Problem

An aspect of the present invention provides a method for constructing a protein scaffold library based on the Kringle domain structure.

Another aspect of the present invention provides protein scaffold variants based on the Kringle domain structure that are derived from the constructed library, which specifically bind to a variety of target molecules to modulate the biological activities of the target molecules.

Still another aspect of the present invention provides DNAs encoding the Kringle domain structure-based protein scaffold variants that specifically bind to the target molecules, and expression vectors comprising the same.

Still another aspect of the present invention provides a method for expressing and purifying protein scaffold variants, based on the Kringle domain structure, that specifically bind to the target molecules.

Still another aspect of the present invention provides a method for preparing Fc-fused protein scaffold variants by fusing an Fc domain of human antibody IgG1 with monomers of the protein scaffold variants based on the Kringle domain structure, whereby Fc-fused protein scaffold variants induce the avidity and immune response.

Still another aspect of the present invention provides a method for constructing homo- and hetero-oligomers by combination of the monomers of the protein scaffold variants based on the Kringle domain structure, and a method for preparing hetero-oligomers to give the multispecificity.

Still another aspect of the present invention provides a method for preparing multispecific monomers and multivalent monomers by grafting target-binding loops of a Kringle domain variant into other loops of another Kringle domain variant with the same or different target binding specificity Yet another aspect of the present invention provides a method and a composition for prevention, detection, diagnosis, treatment or relieving of diseases or disorders, particularly cancers and other immune-related diseases, comprising: administering an effective amount of the Kringle domain structure-based protein scaffold variants to animals.

Technical Solution

According to an aspect of the present invention, there is provided a method for preparing a protein scaffold library based on the Kringle domain structure. Here, the method includes: inducing artificial mutations at amino acid residues except for conserved amino acid residues that are important to maintain the structural scaffold of Kringle domain.

According to one exemplary embodiment of the present invention, the conserved amino acid residues that are important to maintain the structural scaffold of a Kringle domain may include, but is not particularly limited to, at least one residue selected from the group consisting of C1, G6, Y9, D10, G11, T16, G19, C22, Q23, W25, P30, H31, H33, G34, K48, N49, Y50, C51, R52, N53, P54, D55, P61, W62, C63, F64, T65, E73, L74, C75, P78, R79, and C80.

According to one exemplary embodiment of the present invention, the artificial mutation may occur at least one residue selected from the group consisting of amino acid residues 2, 3, 4, 5, 7, 8, 12, 13, 14, 15, 17, 18, 20, 21, 24, 26, 27, 28, 29, 32, 36, 37, 38, 39, 40, 41, 42, 43, 44, 45, 46, 47, 56, 57, 58, 59, 66, 67, 68, 69, 70, 71, 72, 76, and 77, and the amino acid residues may be deleted or substituted with one residue selected from the group consisting of serine, tyrosine, proline, histidine, threonine, asparagine, alanine, aspartate, glutamine, arginine, lysine, glutamic acid or glycine, but the present invention is not particularly limited thereto.

As described above, the numbering system of the Kringle domain residues is dependent on the standard Kringle domain numbering convention (Cao Y et al. (2002) Curr. Med. Chem. Anticancer Agents, 2(6): 667-681; Marti D N et al. (1999) Biochemistry 38(48):15741-15755).

According to another exemplary embodiment of the present invention, the method may further include: inducing artificial mutations at amino acid residues except for conserved amino acid residues that are important to maintain the structural scaffold of a Kringle domain, so that the Kringle domain has an amino acid sequence that does not exist in the nature, by performing PCR on a gene of the Kringle domain that exists in the nature using the gene of the Kringle domain as a template, and primers:

In this case, the variants derived from protein scaffold library may be protein variants based on the Kringle domain structure that have the following amino acid sequence:

(SEQ ID NO: 19)
CXxXxGXxYDGXxXxTXxGXxCQXWXxXxPHXHGXxXxXxXxXxXxKN

YCRNPDXxXxPWCFTXxXxXxXELCXxPRC wherein, X represents one residue selected from the group consisting of serine, tyrosine, proline, histidine, threonine, asparagine, alanine or aspartate, and x represents glutamine, arginine, lysine, glutamic acid and glycine.

According to one exemplary embodiment of the present invention, the Kringle domain may be a Kringle domain derived from human plasminogen, but the present invention is not particularly limited thereto.

According to one exemplary embodiment of the present invention, the primers may be selected from the group consisting of SEQ ID NO: 1 to SEQ ID NO: 8, but the present invention is not particularly limited thereto.

According to one exemplary embodiment of the present invention, examples of the Kringle domain may include a Kringle domain of the plasminogen, but the present invention is not particularly limited thereto. Then, the Kringle domain of the plasminogen has an amino acid sequence set forth in SEQ ID NO: 49, and Kringle domains of variant plasminogens in which at least one amino acid of the amino acid sequence is mutated, that is, substituted, deleted, inversed or translocated are included within the scope of the present invention.

According to one exemplary embodiment of the present invention, the gene encoding the Kringle domain of the plasminogen may include a gene having a DNA sequence set forth in SEQ ID NO: 50, or a gene having more than 80% homology with the DNA sequence in consideration of the degeneracy of genetic codes, but the present invention is not particularly limited thereto.

In addition, there is provided a protein scaffold library constructed based on the Kringle domain prepared in the method for preparing a protein scaffold library according to the present invention.

According to one exemplary embodiment of the present invention, the library may include a library set forth in SEQ ID NO: 13, but the invention is not particularly limited thereto. According to one exemplary embodiment of the present invention, the library may also include a protein scaffold library selected from the group consisting of SEQ ID NO: 14 to SEQ ID NO: 18, but the invention is not particularly limited thereto.

In addition, there is provided a method for screening protein scaffold variants based on the Kringle domain structure with a high specific affinity to the target molecules. Here, the method include: reacting the protein scaffold library with a target molecule.

In the method for screening protein scaffold variants according to the present invention, examples of the target molecule may include, but are not particularly limited to, a death receptor (DR) 4, a death receptor (DR) 5, a tumor necrosis factor-α (TNFα, a glycoprotein IIβIIIα receptor or glycoprotein IIIβIIIα, a vascular endothelial growth factor (VEGF), a vascular endothelial growth factor receptor (VEGFR), a tyrosin kinase inhibitor, an epidermal growth factor receptor, a platelet-derived growth factor (PDGF), a platelet-derived growth factor receptor (PDGFR), a stem cell factor receptor (c-kit), Fms-like tyrosine kinase-3 (Flt-3), interleukin 1, interleukin 6, interleukin 32, an interleukin 2 receptor, CD3, CD11a, CD14, CD15, CD16, CD20 CD32, CD64, or Raf.

Additionally, there is provided a Kringle domain variant having a high specific affinity to the target molecule prepared in the method for screening protein scaffold variants based on the Kringle domain structure that have a high specific affinity to the target molecule.

According to one exemplary embodiment of the present invention, the variant may be a protein scaffold variant based on the Kringle domain structure having at least one amino acid sequence selected from the group consisting of the following amino acid sequences, but the present invention is not particularly limited thereto.

TABLE 2

| SEQ ID NOs | Clone names | Amino acid sequences |
|---|---|---|
| 20 | KD404 | CSRDKGYRYDGDGNKTLKGHKCQHWTKSKPHDHGYRHKLGNED KFKKNYCRNPDTRAGPWCFTDQYRDRDELCYQPRC |
| 21 | KD408 | CDRHKGPKYDGFRDRTHKGHKCQYWDKPRPHHHGHKHGDEFRN RLGKNYCRNPDSQAEPWCFTHKDKYKYELCYQPRC |
| 22 | KD409 | CAKDKGDKYDGHKHKTNRGDKCQTWAKNRPHFHGHRFEVGHEH KIRKNYCRNPDDQDKPWCFTHGYRNQDELCDGPRC |
| 23 | KD413 | CAKAEGTGYDGHEHKTHKGIRCQNWYKSKPHYHGHQFRDGDKIK NKKNYCRNPDPRAGPWCFTHGNRNRYELCNQPRC |
| 24 | KD415 | CTRSKGDEYDGHKHKTNRGLRCQHWPGTKPHFHGDKIKDRHGFR LKKNYCRNPDPQDQPWCFTNRHQHKNELCNQPRC |
| 25 | KD421 | CAGAEGNEYDGDKYKTHKGYRCQRWDKSRPHNHGNKDRHQHEN KVGKNYCRNPDNEAEPWCFTDQHKHGNELCDRPRC |
| 26 | KD437 | CAKSRGYKYDGNRYKTNKGDKCQAWTKTKPHDHGHRHGHGDRF RNRKNYCRNPDHESKPWCFTYRDRYRHELCNRPRC |
| 27 | KD444 | CHRTRGDKYDGYEHKTHGGHRCQHWTEPKPHYHGHRDRNKNGI RDKKNYCRNPDPRAEPWCFTNKNGDKHELCDKPRC |

TABLE 2-continued

| SEQ ID NOs | Clone names | Amino acid sequences |
|---|---|---|
| 28 | KD445 | CHETKGHKYDGHRLRTNKGDRCQPWTKDKPHHHGFRDQYQVRY KLKKNYCRNPDDQNKPWCFTDGNQHEHELCNGPRC |
| 29 | KD449 | CDRYKGYRYDGHRYKTHKGHKCQHWDEDQPHNHGHGHRIKDGF EVRKNYCRNPDAGTKPWCFTDKDQNRHELCYKPRC |
| 30 | KD456 | CDKNRGNGYDGNEIQTDGGVQCQHWTKTKPHHHGLKLQHEHRV KHEKNYCRNPDARTQPWCFTDKHQHKDELCIEPRC |
| 31 | KD459 | CSRYRGHKYDGYKHRTYKGYQCQSWTKDKPHHHGIRHRNKIRDR FGKNYCRNPDTQNQPWCFTYGDEYRYELCNKPRC |
| 32 | Consensus | CARDKGDKYDGHKHKTHKGHKCQHWTKDKPHHHGHRHRDKHR FKLKKNYCRNPDARAKPWCFTDKDRHRHELCNQPRC |

According to another exemplary embodiment of the present invention, the variant may be a protein scaffold variant based on the Kringle domain structure having at least one amino acid sequence selected from the group consisting of the following amino acid sequences, but the present invention is not particularly limited thereto.

TABLE 3

| SEQ ID NOs | Clone names | Amino acid sequences |
|---|---|---|
| 33 | KD502 | CAEDKGARYDGYQYRTHKGIKCQPWYQHEPHYHGHKDKIRHK NRNKKNYCRNPDAGDRPWCFTHRDKYEHELCNRPRC |
| 34 | KD503 | CTQTKGHRYDGYKYETNWGHQCQAWTKHKPHLHGNGHRNR HKVGHEKNYCRNPDHRDGPWCFTNQYENENELCHQPRC |
| 35 | KD505 | CPEDQGDEYDGHEHKTHRGNRCQSWYRPKPHNHGHRIKDRYK YKVKKNYCRNPDTQARPWCFTNRHRDEHELCDQPRC |
| 36 | KD506 | CPEDRGHEYDGDGDKTNRGHGCQYWDQNKPHHHGHRDKDKF KHRIKKNYCRNPDYETGPWCFTNRYRNKNELCHEPRC |
| 37 | KD509 | CAQSKGYRYDGDKDKTNKGHKCQDWAQNKPHVHGHRHEDRH QVKSRKNYCRNPDARARPWCFTNQVRYRNELCYKPRC |
| 38 | KD537 | CTRTKGAKYDGYKHRTHEGNKCQSWNKARPHLHGDRLGNKY EHKARKNYCRNPDNRAEPWCFTDKNQNQHELCYGPRC |
| 39 | KD542 | CNRAGGHKYDGDRYRTHRGDGCQNWAKTKPHHHGIGHRDKIR DKYRKNYCRNPDAKNGPWCFTNRNGDKNELCIQPRC |
| 40 | KD548 | CHQTQGPKYDGNKDKTHKGHKCQSWTKNRPHHHGNKIENED ENRFQKNYCRNPDNKHEPWCFTHGHRDKHELCHEPRC |
| 41 | KD555 | CDGAQGNGYDGNKHKTHRGNKCQAWPKHGPHYHGNGDQDGH RNKHKKNYCRNPDTRSRPWCFTDQNGHKDELCHGPRC |
| 42 | KD559 | CNKHKGPRYDGHKDKTNKGHECQPWNRPKPHDHGHKHQFKD KNRLEKNYCRNPDHRNEPWCFTGNRNGDELCFRPRC |
| 43 | Consensus | CTEDKGHRYDGDKHKTHKGHKCQSWNKHKPHHHGHRHKDR HKNKHKKNYCRNPDHRARPWCFTNRNRNENELCHRPRC |

According to still another exemplary embodiment of the present invention, the variant may be a protein scaffold variant based on the Kringle domain structure having at least one amino acid sequence selected from the group consisting of the following amino acid sequences, but the present invention is not particularly limited thereto.

TABLE 4

| SEQ ID NOs | Clone names | Amino acid sequences |
|---|---|---|
| 44 | KDT01 | CYEDKGPQYDGDEYGTHKGHRCQNWDENRPHPHGIGHQHKHQ VKDGKNYCRNPDDETEPWCFTHKDKYGHELCNRPRC |
| 45 | KDT02 | CAQDGGPGYDGDKHGTHGGHECQDWTKDGPHIHGFRDQFRDE DQHGKNYCRNPDSQHGPWCFTNEDEHRNELCHEPRC |
| 46 | KDT08 | CPKSGGNGYDGYKHGTNEGLQCQNWDRAKPHDHGIEVQNEYG DRHEKNNCRNPDDKTRPWCFTHKDRYRNELCYQPRC |
| 47 | KDT26 | CPRDQGNQYDGFRYGTYRGHRCQHWTRDEPHFHGFGHQHKYT YRHKKNYCRNPDARPRPWCFTHRYQNRNELCHQPRC |
| 48 | Consensus | CDEDKGPGYDGDKHGTHKGHECQDWTKDRPHDHGHGDQHKY EDKHGKNYCRNPDDETRPWCFTHKDRNRNELCDQPRC |

Additionally, there is provided a method for preparing Fc-fused structures, homo-oligomers or hetero-oligomers using the monomers of the protein scaffold variant, prepared in the method for screening protein scaffold variants based on the Kringle domain structure according to the present invention, which binds to the same target molecule.

Also, there is provided a method for preparing oligomers capable of binding to multitarget molecules at the same time. Here, the method includes: isolating the protein scaffold monomers, as prepared in the method for screening protein scaffold variants based on the Kringle domain structure according to the present invention, which bind respectively to two or more different target molecules, and combining the monomers, by tandem assembly using a linker, to prepare oligomers.

In addition, there is provided a method for preparing multispecific monomers and multivalent monomers by grafting target-binding loops of a Kringle domain variant into other loops of another Kringle domain variant with the same or different target binding specificity. Here, the method includes: isolating the protein scaffold monomers from Kringle domain library, as prepared in the method for screening protein scaffold variants based on the Kringle domain structure according to the present invention, which bind respectively to two or more different target molecules, and analyzing a binding loop of the protein scaffold monomers.

Additionally, there is provided a composition for treatment or prevention of cancer, comprising as an active component the Kringle domain variant having a high specific affinity to the target molecule according to the present invention.

Also, there is provided a composition for treatment or prevention of autoimmune diseases that are caused by the over-expression or presence of excessive TNFα comprising the protein scaffold variant having a high specific affinity to the target molecule according to the present invention.

Hereinafter, exemplary embodiments of the present invention are described in more detail.

In accordance with the present invention, the Kringle domain used in the protein scaffold (or, protein template) library includes 1663 Kringle domains, which have different amino acid sequences and are distributed in 893 proteins of various living organisms existing in the nature, or preferably includes 39 Kringle domains, which have different amino acid sequences and are distributed in 31 human-derived proteins (see: Prosite: http://kr.expasy.org/prosite/; SMART: http://smart.embl-heidelberg.de/).

In accordance with the present invention, the Kringle domain may be a human-derived protein such as prothrombin, plasminogen, plasmin, a urokinase-type plasminogen activator (uPa), a tissue-type plasminogen activator (tPa), a blood coagulation factor XII (Hagenman factor), apolipoprotein A, a hepatocyte growth factor (HGF/Scatter Factor, HGF/SF), a macrophage-stimulating protein (MSP/HGF like protein), Kremen, neurotrypsin (Neurotrypsin/Motopsin), or a plasma hyaluronan binding protein (PHBP).

In accordance with the present invention, the term target molecule means molecules present in the nature, such as proteins, phospholipids, cell membranes, nucleic acids (DNA, RNA), carbohydrates, ions, and the like, and the target molecule includes single molecules or their complex molecules. Also, the target molecule may include cells, tissues, or new types of molecules that do not exist in the nature.

In accordance with the present invention, human-derived DR5 is a receptor that belongs to one of a (death receptor-5; TRAIL-receptor 2; DR5) TNF receptor family, binds to TRAIL, and has intracellular death domain at the C terminus (Pan, et al., Science 277:815-818, 1997). When DR5 binds to TRAIL, the apoptosis is induced in vitro or in vivo in a variety of cancer cell lines.

In accordance with the present invention, human-derived DR4 is a receptor that belongs to one of a (death receptor-4; TRAIL-receptor 1; DR4) TNF receptor family, binds to TRAIL, and has intracellular death domain at the C terminus (Pan, et al., Science 276: 111-113, 1997). When DR4 binds to TRAIL, the apoptosis is induced in vitro or in vivo in a variety of cancer cell lines (Pan, et al., Science 276:111-113, 1997).

In accordance with the present invention, human-derived tumor necrosis factor alpha (TNFα is inflammatory cytokine secreted from various cells such as monocytes or macrophage and an inflammation-inducing protein having various functions (Pennica D. et al., Nature, 312:724-729, 1984; Feldmann M, Nature Rev. Immunol, 2:364-371, 2002; Zhang G, Curr Opin Struct Biol, 14:154-160, 2004). TNFα is associated with various diseases such as arthritis, insulin resistance, lipid metabolism and the like. The TNFα functions to induce diseases by inducing the cell death in various cells expressing TNF receptors (TNFR1, TNFR2) (Feldmann M, Nature Rev. Immunol, 2:364-371, 2002; Zhang G, Curr Opin Struct Biol, 14:154-160, 2004).

The method for constructing a protein scaffold library based on the Kringle domain structure according to the present invention is used to maintain an amino acid sequence that give the typical structural stability of the Kringle domain (for example, 3 intramolecular disulfide bonds (with 1-6, 2-4 and 3-5 disulfide bonding patterns) and their surrounding conserved amino acid residues), and to allow a region of the loop structure to include various combinations of amino acid sequences that do not exist in the nature, wherein the region of the loop structure is formed by disulfide bonding.

From the protein scaffold library based on the Kringle domain structure according to the present invention, it is possible to screen and isolate Kringle domain variants that specifically bind to various target molecules to control the biological activities of the target molecules.

Since the Kringle domain variants specifically binding to the target molecules according to the present invention not only bind to specific sites of the target molecules but also specifically bind to various sites of the target molecules, it is possible to isolate polyclonal Kringle domain variants binding to the target molecule.

The Kringle domain variants specifically binding to the target molecules according to the present invention may be expressed and purified in a liquid phase in yeast, *pichia* or animal host cells.

The Kringle domain variants specifically binding to the target molecules according to the present invention may be constructed in the form of monomers or oligomers by combinations of the monomers, and multispecific oligomers specifically binding to only one target molecule may be constructed by the combination of selected monomers with respect to various target molecules.

Based on the analysis of the binding loops of the monomers which binds to different sites of the same target molecule or two or more different target molecules according to the present invention, multivalent monomers or multispecific monomers may be prepared by grafting target-binding loops of a Kringle domain variant into other loops of another Kringle domain variant with the same or different target binding specificity.

The Kringle domain variants specifically binding to the target molecules DR4 and DR5 according to the present invention are used as monomers that may induce cell death in different cancer cell lines. Also, the Kringle domain variants according to the present invention may be constructed in the form of oligomers that bind to their same target molecules, and be used to generate dual specific oligomers that may bind to the target molecules DR4 and DR5 at the same time, thus to maximize the effect on apoptotic cancer cell death. The selected monomers that bind to the various target molecules may also combined to prepare multispecific oligomers that specifically bind to at least one target molecule. Based on the analysis of the binding loop, it is possible to prepare multivalent monomers by the binding loop grafting into the same Kringle domain variant with the same target molecule, and also to prepare multispecific monomers by grafting the binding loops into the same or different Kringle domain variant against the same or different target molecule.

The Kringle domain variants that may specifically bind to the target molecule TNFα according to the present invention may be used to treat diseases (i.e. arthritis, Crohn's disease) caused by the presence of excessive TNFα by neutralizing various kinds of TNFα with monomers. Also, the Kringle domain variants according to the present invention may be constructed in the form of oligomers that bind to the target molecule TNFα and be fused with marker molecules (for example, Tags) or constant regions (Fc) of antibodies to maximize the biological activities. Also, the selected monomers that bind to the different target molecules may be combined to prepare multispecific oligomers that specifically bind to at least one target molecule. Based on the analysis of the binding loop, it is possible to prepare multivalent monomers by grafting the binding loops into the same Kringle domain variant with the same target molecule, and also to prepare multispecific monomers by grafting the binding loops into the same or different Kringle domain variant against the same target molecule.

Another exemplary embodiment of the present invention is to provide a method and composition for prevention, detection, diagnosis, treatment or relieving of diseases or disorders, particularly cancers and other immune-related diseases, comprising: administering an effective amount of the monomers, oligomers, fusion proteins, multivalent monomers, multispecific monomers and the like of the Kringle domain variant to animals, preferably human.

One exemplary embodiment of the present invention is to provide a protein comprising artificial monomers that specifically bind to the target molecules. According to some exemplary embodiments, a monomer domain of the protein has one, two, three or more disulfide bonds.

In the present invention, the term "monomer domain" or "monomer" means a separate region found in proteins or polypeptides. The monomer domain forms a tertiary structure in solution in the absence of flanking natural amino acid sequences. The monomer domain of the present invention may be selected to specifically bind to target molecules.

In the present invention, the term "loop" means a region of the monomer domain typically exposed to the environment by the binding of a scaffold structure of the monomer domain protein and is associated with the binding to the target molecules.

In the present invention, the term "oligomer" means a peptide containing at least two monomer domains. Monomer domains separated in an oligomer may be linked by a linker. Homo-oligomers are composed of the same Kringle domain variants and Hetero-oligomers are composed of two or more different Kringle domain variants.

The term "target molecule" according to the present invention includes wide range of substances and molecules spanning from single molecules to complex target molecules. The target molecules may be other molecules that may be recognized by proteins, nucleic acids, lipids, carbohydrates or peptide domains. The target molecules are included in the screening analysis as disclosed herein, or may be defined to facilitate or inhibit the interaction of specific proteins.

In the present invention, the term "linker" means a region or a group of regions that link two or more separate monomer domains or bind to the separate monomer domains. The linker maintains a separate state of the monomer domains when it connects the separate monomer domains together with oligomers. Suitable linkers comprise polypeptides, polynucleic acids and analogs thereof. Suitable linkers selectively substituted alkylene having at least one oxygen atom introduced into the carbon backbone. A linker may comprise some portions of original sequences, and their variant or synthetic sequences.

In the present invention, the term "vector" means a polynucleotide that may replicate in a host independently from the host chromosome. Examples of vectors comprise plasmids. Typically, vectors have their replication origins, and may include transcription and translation terminators, transcription and translation initiation sequences, and a promoter that is useful to control the expression of specific nucleic acids.

In the present invention, the term "recombination" means that nucleic acids, proteins or vectors are modified by administration of heterologous nucleic acids or proteins, or changes of natural nucleic acids or proteins. Accordingly, recombinant cells express genes that are not found in the form of original (non-recombinant) cells, or express genes that are not expressed at all or are abnormal but not well-expressed.

In the present invention, the term "protein variant based on the Kringle domain structure" or "protein scaffold variant based on the Kringle domain structure" means proteins that function to maintain the structure of Kringle domain but include amino acid sequences that do not exist in the nature since the amino acid sequences, which provide typical structural stability to the Kringle domains existing in the nature, are conserved to form a structural scaffold [for example, 3 intracellular disulfide bonds (with 1-6, 2-4 and 3-5 disulfide bonding patterns) and thus a prepared loop structure scaffold], but the loop structure also includes various combinations of amino acid sequences that do not exist in the nature. In addition to proteins to which Kringle domains existing in the nature, these protein variants based on the Kringle domain structure may specifically bind to a variety of target molecules to control their biological activities.

In the present invention, the expression "protein scaffold library" means a library that is composed of protein scaffolds whose amino acid sequences that provide typical structural stability to Kringle domains are conserved, but whose various amino acid sequences that do not exist in the nature are at the loop structure. This protein scaffold library may be prepared in various techniques, such as overlapping PCR, DNA shuffling, error prone PCR, artificial DNA synthesis and the like, using a variety of synthetic primers. Also, the amplified library may be inserted into a yeast surface expression vector or an animal cell surface expression vector, transformed and expressed. Since there is no limit to the size of the protein scaffold library but the library size is limited in a transformation procedure, the diversity of the library is generally in a range of approximately $10^7$ to $10^{13}$. From such expressed protein scaffold library, it is possible to screen and isolate certain protein scaffold variants that specifically bind to various target molecules.

In the present invention, the expression "amino acids that do not exist in the nature" mean amino acids other than amino acids that occur in the corresponding positions by arrangement of naturally occurring polypeptides.

The oligomers of the present invention comprise two or more monomers. For example, the oligomers of the present invention may comprise 2 to approximately 4, 2 to approximately 8, 2 to approximately 10, or 3 to approximately 10 monomer domains and particularly comprise approximately 4, 5, 6 or 7 monomer domains. In some exemplary embodiments, each monomer domain specifically binds to one target molecule. In some of these exemplary embodiments, each monomer domain binds to different positions on a target molecule. Multiple monomer domains that bind to the same target molecule cause the binding effect to allow oligomers to have an improved binding affinity to the target molecule, when compared to individual monomers.

In another exemplary embodiment, oligomers comprise monomer domains having specificity to different target molecules. For example, various oligomers in the monomer domain may specifically bind to different components of the viral replication system, or bind to different target molecules in the target cells or tissues. Similarly, therapeutic molecules may target cells or tissues by allowing a therapeutic substance to bind to monomers of an oligomer comprising another monomer domain having specificity to the cells or tissues.

Oligomers may comprise various combinations of monomers. For example, monomer domains selected from a single oligomer may be the same as or identical to each other.

In accordance with the present invention, for example, an oligomer may be one selected from the group consisting of: (1) homogeneous oligomers (i.e. A1-A1-A1-A1 in the same domain); (2) heterogenous oligomers, (i.e. A1-A2-A3-A4).

In the present invention, the selected monomer domains may be linked by a linker to form an oligomer.

The linking of the selected monomer domains by the linker may be achieved by using a variety of techniques known in the art. For example, a combinatorial assembly of polynucleotides coating the selected monomers may be achieved by treatment of restriction enzymes and ligation, a PCR-based self-priming overlap reaction, or other recombination methods.

Linkers may naturally occur or be synthesized, or be combinations of the natural or synthetic linkers. For example, the synthetic linkers may be linkers having randomized sequences and sizes.

In the present invention, the selected monomer domains may form multivalent monomer and multispecific monomers by the loop grafting, based on the analysis of the binding loop.

The analysis of the binding loop may be achieved by a yeast cell expression technique based on loops 1-7 described in Examples and shown in FIG. 3.

The loop grafting may be achieved by using a variety of techniques known in the art. For example, a combinatorial assembly of polynucleotides encoding the selected monomers may be achieved by treatment of restriction enzymes and re-ligation, a PCR-based self-priming overlap reaction, or other recombination methods.

Advantageous Effects

As described above, the method for constructing a protein scaffold library based on the Kringle domain structure according to one exemplary embodiment of the present invention may be useful to screen and isolate Kringle domain variants that may specifically bind to various target molecules to modulate the biological activities of the target molecules, by using the protein scaffold library based on the Kringle domain structure, by maintaining an amino acid sequence that provide the typical structural stability of Kringle domains and allowing a region of the loop structure to include various amino acid sequences that do not exist in the nature, wherein the region of the loop structure is formed by disulfide bonding.

Also, the Kringle domain variant specifically binding to target molecules according to one exemplary embodiment of the present invention may be useful to isolate polyclonal Kringle domain variant from the target molecules since they may not only bind to a specific region of the target molecules but also specifically bind to several regions of the target molecules.

In addition, the Kringle domain variant specifically binding to target molecules according to one exemplary embodiment of the present invention may be useful to prepare multispecific oligomers that specifically bind to at least one target molecule since they may be expressed and purified in a liquid state in *pichia* host cells, be constructed into oligomers by using these monomers or their combinations and the selected monomers binding to a variety of the target molecules are combined with each other.

For example, the Kringle domain variant specifically binding to target molecules DR4 and DR5 according to one exemplary embodiment of the present invention may be used as monomers that may induce cell death in different cancer cell lines. Also, the Kringle domain variants according to one exemplary embodiment of the present invention may be constructed in the form of oligomers that bind to their same target molecules, and be used to generate dual specific oligomers that may bind to the target molecules DR4 and DR5 at the same time, thus to maximize the effect on the death of cancer cell. Furthermore, the Kringle domain variant specifically binding to target molecules DR4 and DR5 according to one exemplary embodiment of the present invention may be useful to generate dual specific oligomers that may bind to the target molecules DR4 and DR5 at the same time, thus to maximize the effect on the cancer cell death. Also, the Kringle domain variants according to one exemplary embodiment of the present invention may be useful to prepare multispecific monomers that may bind to the target molecules DR4 and DR5 at the same time, thus to maximize the effect on the cancer cell death. The Kringle domain variants according to one exemplary embodiment of the present invention may be useful to prepare multispecific monomers by grafting the target binding loops of the selected monomers that bind to various target molecules, and the Kringle domain variants that may specifically bind to the target molecule TNFα according to one exemplary embodiment of the present invention may also be used to treat diseases (i.e. arthritis, Crohn's disease) caused by the presence of excessive TNFα by neutralizing various kinds of TNFα with monomers. Also, the Kringle domain variants according to one exemplary embodiment of the present invention may be useful to maximize the biological activities since they may be constructed in the form of oligomers that bind to the target molecule TNFα and may be fused with marker molecules (for example, Tags) or constant regions (Fc) of antibodies. Also, the Kringle domain variants that may specifically bind to the target molecule TNFα according to one exemplary embodiment of the present invention may be useful to prepare multispecific oligomers that specifically bind to at least one target molecule by the combination of the selected monomers that bind to the different target molecules. Furthermore, the Kringle domain variants that may specifically bind to the target molecule TNFα according to one exemplary embodiment of the present invention may be useful to prepare multivalent monomers by grafting the binding loop into the same Kringle domain variant against the same target molecule.

As described above, the present invention is to provide a method and composition for prevention, detection, diagnosis, treatment or relieving of diseases or disorders, particularly cancers and other immune-related diseases, comprising: administering an effective amount of the monomers, oligomers, fusion proteins, multivalent monomers, multispecific monomers and the like of the Kringle domain variant to animals, preferably human.

BRIEF DESCRIPTION OF DRAWINGS

FIG. 1 shows conserved amino acid sequences of 39 Kringle domains having different amino acid sequences present in human.

FIG. 4a shows the improvement of affinity of a screened Kringle domain variant to each target molecule, FIG. 4b shows the construction of oligomers of the Kringle domain variant according to the biological mechanism of each target molecule, FIG. 4c shows the construction of Fc fused-structures of the screened Kringle domain variant to each target molecule, and FIG. 4d schematically shows the analysis of a binding loop of the screened Kringle domain variant to each target molecule and the construction of multivalent monomers and multispecific monomers.

FIG. 6a shows a procedure to prepare a gene of the Kringle domain protein scaffold library by overlapping 8 primers, and FIG. 6b schematically shows a procedure of yeast surface expression.

FIG. 58 shows the results evaluating that wild-type plasminogen Kringle domain 2, anti-TNFα Kringle domain variants, KDT26 and KDT26-Fc, and infliximab inhibit the TNFα-mediated cell death of a WEHI 164 cell line. FIG. 59 shows log-rank (Mantel-Cox) test illustrating the in vivo inhibition of TNFα mediated toxicity of human IgG1 infliximab and KDT26-Fc as the control. The P-values are indicated at the right.

FIG. 60 shows a schematic picture of the constructed homo-dimers. FIG. 61 shows the affinity of the anti-DR4 KD413 and KD415 homo-dimers against target molecule DR4 which assayed by ELISA. FIG. 62 shows the affinity of the anti-DR5 KD506 and KD548 homo-dimers against target molecule DR5 which assayed by ELISA. FIG. 63 shows the affinity of the anti-TNFα KDT26 homo-dimer against target molecule TNFα which assayed by ELISA.

FIGS. 64-68 show schematic pictures of hetero-dimer that constructed by linking anti-DR4 Kringle domain variant, KD413 or KD415, and anti-DR5 Kringle domain variant, KD506, with using the $(G_4S)_4$ linker, and also represents the affinity of the hetero-dimers against the target molecules which is assayed by ELISA.

FIG. 64 shows a schematic picture of the constructed hetero-dimer.

FIG. 65 show the affinity of the KD413-KD415 hetero-dimer against target molecule DR4, FIG. 66 shows the affinity of the KD413-KD506 hetero-dimer against target molecule DR4, and FIG. 67 shows the affinity of the KD413-KD506 hetero-dimer against target molecule DR5, which assayed by ELISA. FIG. 68 is the picture of the binding of the KD413-KD506 to the DR4 and the DR5 which is assayed by sandwich ELISA.

FIG. 71 is the result that anti-DR4 bivalent monomer, KD413-4, simultaneously binds to target molecule DR4 which coated in the bottom and the soluble DR4. FIG. 72 is the result that anti-DR4/DR5 bispecific monomer, KD413-5, simultaneously binds to target molecule DR4 which coated in the bottom and the soluble DR5. FIG. 73 is the result that anti-DR4/DR5 bispecific monomer, KD506-4, simultaneously binds to target molecule DR5 which coated in the bottom and the soluble DR4. KD413L56, KD506L567, and KD548L56 are used as the control, respectively and it is confirmed that there is no bivalency or bi-specificity, by sandwich ELISA.

BEST MODE FOR CARRYING OUT THE INVENTION

Figure 2:
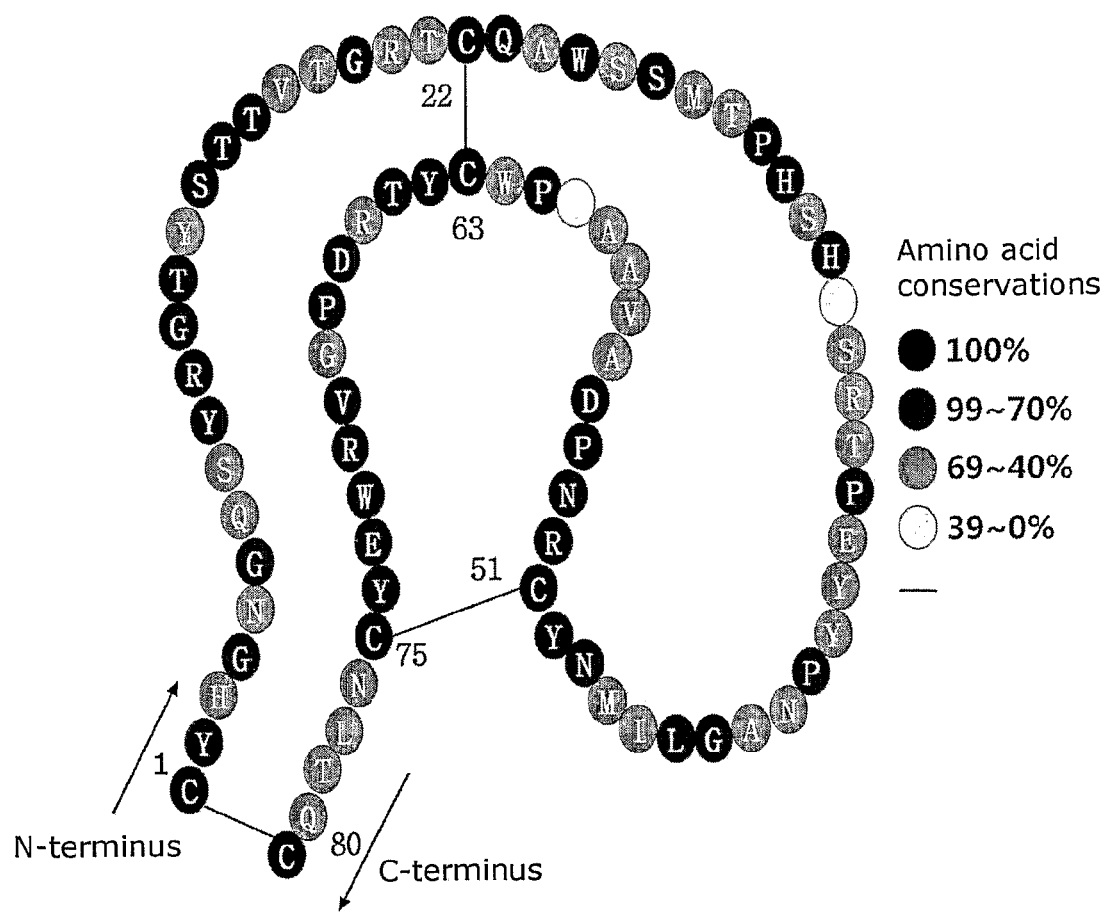
FIG. 2 schematically shows a human-derived Kringle domain having the most conserved amino acid residues and their conservation rates.

Hereinafter, non-limiting examples of the present invention are now described in more detail.

Example 1

Characteristics of Amino Acid Sequence and Structure of Human Kringle Domain

39 Kringle domains having different amino acid sequences are distributed in 31 human proteins (see: Prosite (Hulo N., et al., Nucleic Acids Res, 36:D245-249, 2008; Website: http://kr.expasy.org/prosite/; SMART (Letunic I., et al., Nucleic Acids Res, 34:D257-D260, 2006; Website: http://smart.embl-heidelberg.de/) (Castellino, et al., J Mol Evol, 26:358-369, 1987; Ikeo, et al., J Mol Evol, 40:331-336, 1995). Representative examples of proteins containing the Kringle domains include apolipoprotein A (38 Kringle domains), a blood coagulation factor XII (1 Kringle domain), a hepatocyte growth factor (HGF, 4 Kringle domains), a hepatocyte growth factor like protein (4 Kringle domains), a hepatocyte growth factor activator, plasminogen (5 Kringle domains), thrombin (2 Kringle domains), a tissue plasminogen activator (TPA, 2 Kringle domains), and an urokinase-type plasminogen activator (1 Kringle domain).

Figure 1:
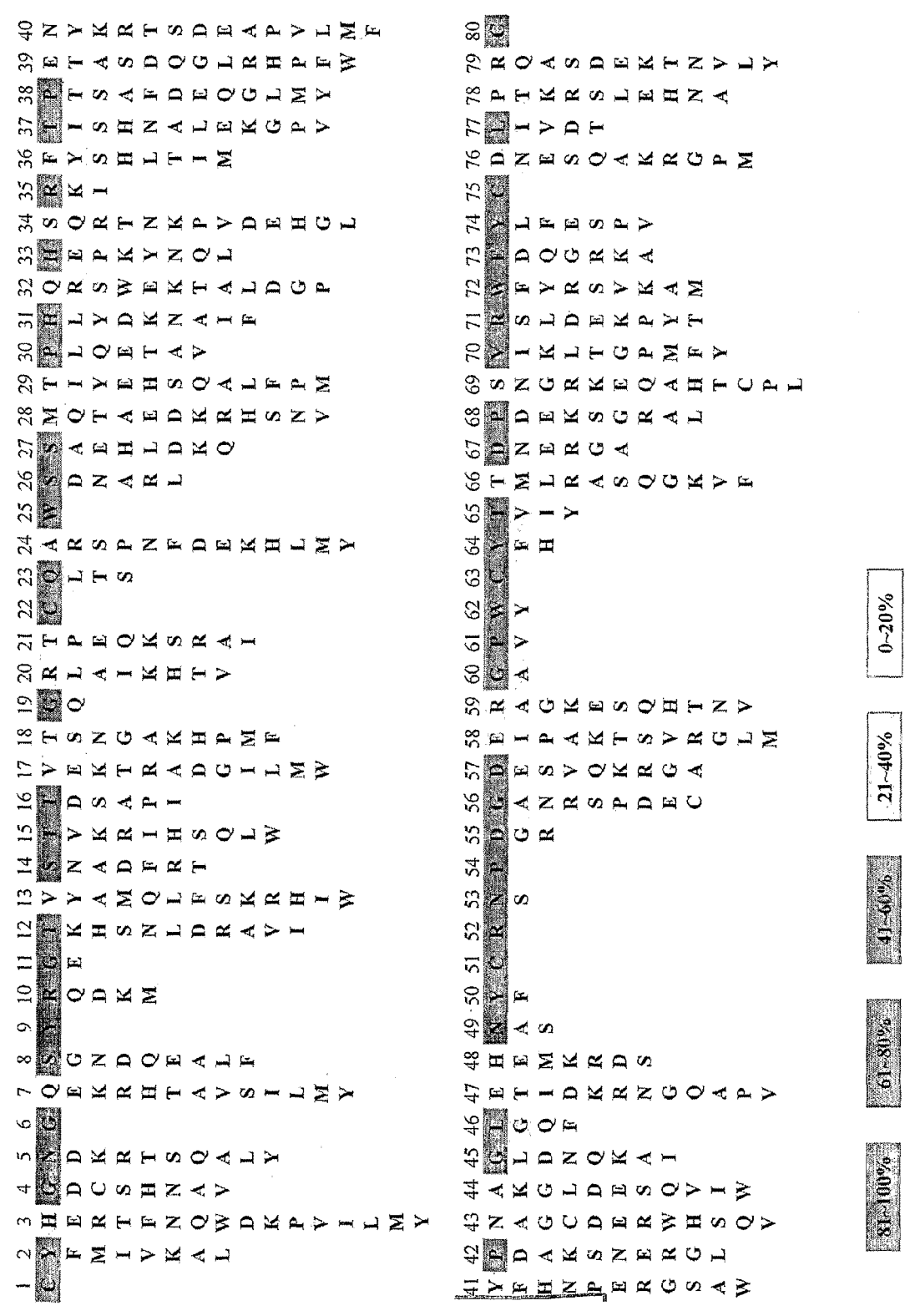

FIG. 1 shows conserved amino acid sequences of 39 Kringle domains having different amino acid sequences present in human. As shown in FIG. 1, each Kringle domain is composed of approximately 80 amino acids, and has 6 conserved cysteines located at specific sites and different non-conserved amino acids distributed at the other sites (Cao, et al., Curr. Med. Chem. 12:667-681, 2002). The amino acids were represented by 5 colors, depending on the conservation rate, and all the other amino acids occurring at each amino acid site are expressed. It was shown that extraordinarily various kinds of amino acids are present in a less-conserved region of the amino acid sequence. This indicates that it is possible to maintain an amino acid sequence that provide the typical structural stability of the Kringle domain (for example, 3 intramolecular disulfide bonds (with 1-6, 2-4 and 3-5 disulfide bonding patterns) and their surrounding conserved amino acid residues), and to construct an amino acid combinatorial library at sites having relatively less-conserved amino acids.

FIG. 2 schematically shows a human-derived Kringle domain having the most conserved amino acid residues and their conservation rates. The 100% conserved residues are cysteine residues (Cys1, Cys22, Cys51, Cys63, Cys75 and Cys80) and their surrounding residues that provide the structural stability of the Kringle domain. Most of the amino acids located at the other sites have more than 40% or 70% conservation rates, and the 35$^{th}$ most conserved amino acid residue is Gly, and its conservation rate is about 35%. The 2-dimensional structure of the typical Kringle domain is characterized by disulfide bonds between its 6 conserved cysteine residues, and has 1-6, 2-4 and 3-5 disulfide bonding patterns. That is, the disulfide bonding patterns are formed between cysteines 1 and 80, between cysteines 22 and 63, and between cysteines 51 and 75 (Ikeo, et al., J Mol Evol, 40:331-336, 1995; Castellino, et al., Ciba Found Symp, 212:46-60, 1997; Marti, et al., Biochemistry, 38:15741-15755, 1999). The 6 conserved cysteines are used to form 3 disulfide bonds, which enhance the structural stability of the Kringle domain (Magnusson, et al., Leiden Universitaire Pers. pp. 25, 1975).

Figure 3:
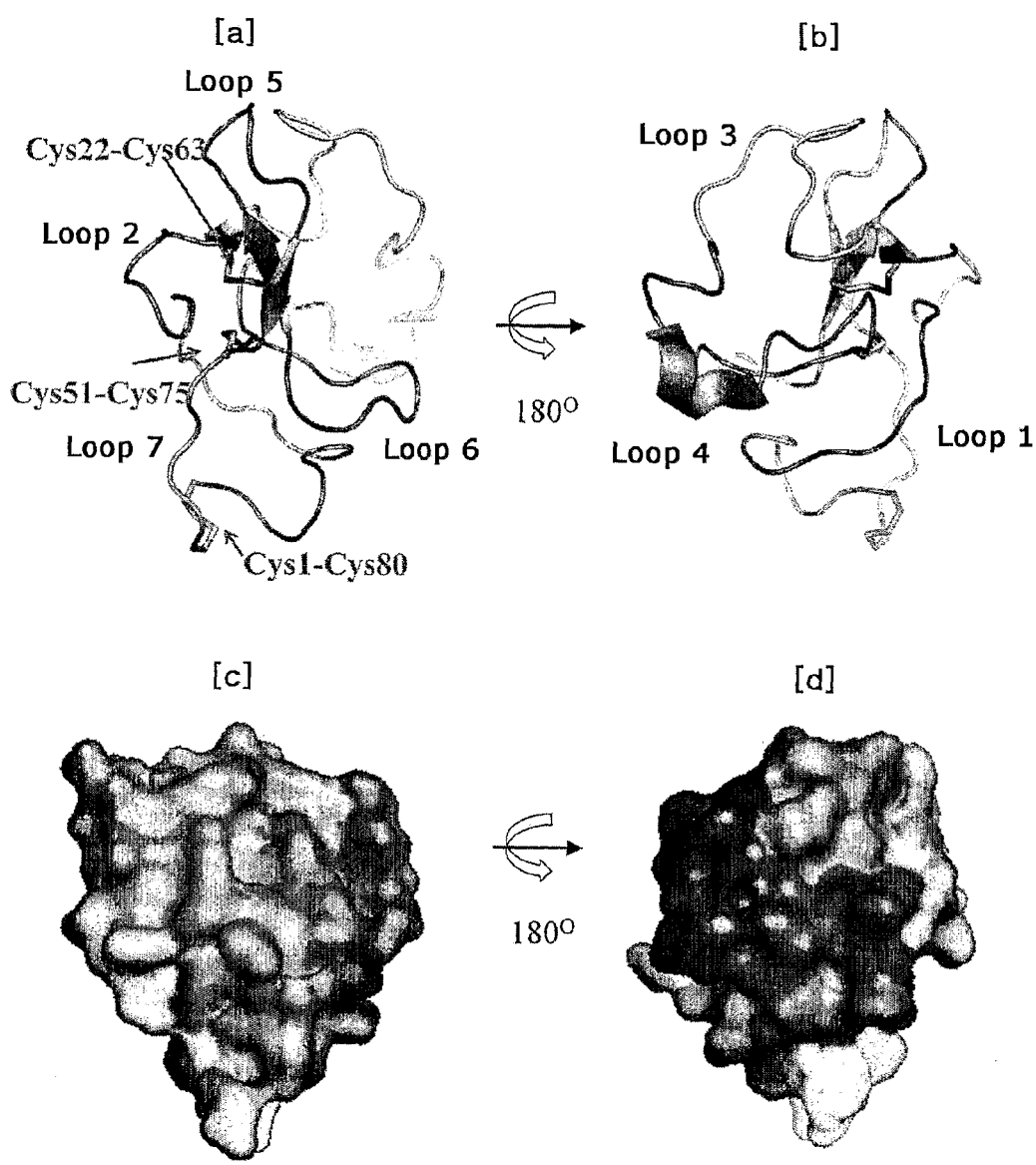
FIG. 3 shows 7 loops each having a less-conserved amino acid sequence, based on the (PDB ID=1B2I) tertiary structure of plasminogen Kringle domain 2. Here, FIG. 3a and b show a secondary structure and 3 disulfide bonds of the plasminogen Kringle domain 2, and FIG. 3c and d show a surface of the plasminogen Kringle domain 2.

FIG. 3 shows 7 loops each having a less-conserved amino acid sequence, based on the (PDB ID=1I5K) tertiary structure of plasminogen Kringle domain 2. Here, FIGS. 3a and b show a secondary structure and 3 disulfide bonds of the plasminogen Kringle domain 2, and FIGS. 3c and d show a surface of the plasminogen Kringle domain 2. In order to develop a protein structural scaffold having high affinity and high specificity for various target molecules such as complementarity determining regions (CDR) of antibody, it is optimal to use proteins having a flexible loop structure including a constant amino acid region that give the structural stability and its surrounding region in which amino acids may be mutated. In this aspect, regions of loops 1 to 7 into which various combinations of amino acids may be introduced were determined, based on the Kringle domain folding. Loops 1 to 7 are composed of residues 2 to 13(loop 1), residues 14 to 21(loop 2), residues 23 to 36(loop 3), residues 37 to 50(loop 4), residues 52 to 62(loop 5), residues 64 to 74(loop 6), and residues 76 to 79(loop 7), respectively. The plasminogen Kringle domain 2 has an approximately 26% β-pleated structure, an approximately 13% β-turn, an approximately 15% $3_1$-helical structure, and an approximately 6% $3_{10}$-helical structure, the reminder of plasminogen Kringle domain 2 has structural characteristics of random loops (Marti D N. Et al., Biochemistry, 38:15741-15755, 1999).

Example 2

Figure 4:
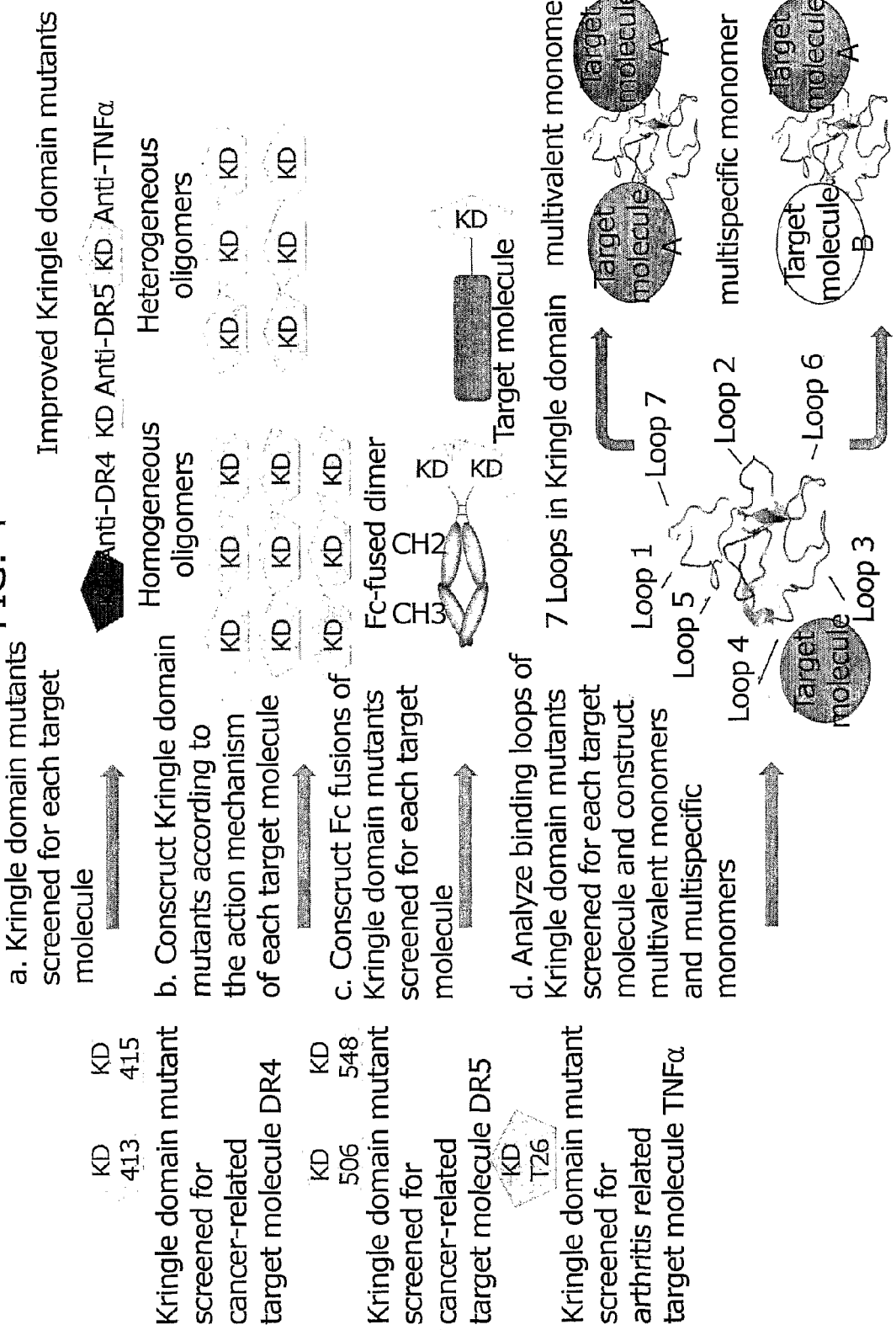
FIG. 4 schematically shows the use of protein scaffold monomers after constructing a protein scaffold library based on the Kringle domain structure and separating protein scaffold monomers that specifically bind to target molecules.

A Method of Constructing Oligomers by Fusion of Variant Monomers Based on Kringle Domain Structure, a Method of Preparing Multispecific-Oligomers and a Construction Method of Fusion with Marker Molecule FIG. 4 schematically shows the use of protein scaffold monomers after constructing a protein scaffold library based on the Kringle domain structure and separating protein scaffold monomers that specifically bind to target molecules. FIG. 4a schematically shows the use of the protein scaffold monomers as monomers that may bind to a target molecule to control the biological activities of the target molecule, and FIG. 4b schematically shows a method of using the protein scaffold monomers as homo-oligomers or hetero-oligomers such as dimers, trimers and the like that are generated by linking of screened monomers by linkers and combination of the linked monomers so that they can bind to target molecules with high affinity and specificity. When target molecules have different among the heterogenous oligomers, the heterogenous oligomers have advantages in that it is possible to recognize target molecules A and B at the same time to newly adjust the biological activities of the target molecules. Of course, the target molecules cannot be two, but more than two. Accordingly, a plurality of target molecules may be used to form a multispecific oligomer. Advantages in construction and generation of oligomers are that the affinity to target molecules is improved due to avidity effect, and it is possible to effectively adjust the biological activities of the target molecule by the combination of monomers that bind to various regions of the target molecules, and the oligomers are advantageous in pharmacokinetic aspects since they have a large volume. FIG. 4c schematically shows a method for constructing a fusion protein fused with marker molecules (for example, 6×His tags, C-myc tag, Zinc-fingers, coiled-coil proteins, DNA binding proteins, enzymes) or constant regions (Fc) of antibodies, based on the screened Kringle domain, thus to provide additional functions to the protein scaffold monomers. When a marker molecule is fused with a Kringle domain, the characteristics of the marker molecule may be additionally introduced into the Kringle domain, and the fusion protein may be used for the purpose of purification, analysis, imaging, treatment, etc. When a constant region of antibody is fused with a Kringle domain, the fusion protein may be used to induce immune cells to have a variety of biological activities in vivo, in addition to the purification and the imaging. Also, these fusion proteins are advantageous in pharmacokinetic aspects since they have a large volume. FIG. 4d shows that analyzing binding loop which binds to a target molecule in selected Kringle domain variants that bind to one or two target molecules as described above, and then grafting the binding loops into other loops that does not participate in the binding to the target molecule, thus to provide new functions. Firstly, when multivalent monomers are constructed by grafting target-binding loops into non-binding loops of the same Kringle domain variant against the same target molecule, only the grafted bivalent monomers may be used to induce the avidity effect. The multi-binding monomers may be applied to a variety of drug delivery systems, in which the use of antibodies is impossible since a protein constantly maintains a molecular weight of 13 kDa. Secondly, when multispecific monomers are constructed by grafting binding loop into the non-binding loops of the same or different Kringle domain variant against the same or different target molecule, the grafted multispecific monomers may be used to overcome the disadvantages in targeting each of the target molecules only, and to induce the synergic effect. Also, the multispecific monomers may apply to a variety of drug delivery systems which the use of antibodies is impossible since a protein constantly maintains a molecular weight of 13 kDa.

Example 3

Construction Strategy and Construction of Protein Scaffold Library Based on Kringle Domain Structure Based on the analysis results of the amino acid sequences and the structural characteristics of the human Kringle domains as described in Example 1, a Kringle domain library was constructed by introducing amino acid mutations onto regions of loops 1-7 while maintaining a stable structural scaffold of the Kringle domain and separating protein scaffold variants based on the Kringle domain structure from the Kringle domain library. Here, the protein scaffold variants function to specifically bind to a variety of target molecules to adjust the biological activities of the target molecule. For this purpose, a strategy for constructing a Kringle domain library was established to maintain a constant amino acid sequence, which provides the typical structural stability of the Kringle domain (for example, 3 intracellular disulfide bonds (with 1-6, 2-4 and 3-5 disulfide bonding patterns) and their surrounding conserved amino acid residues), and introduce mutations into a region of the loop structure, which are generated by the disulfide bonding and structurally flexible, to have various combinations of amino acid sequences that do not exist in the nature.

Figure 5:
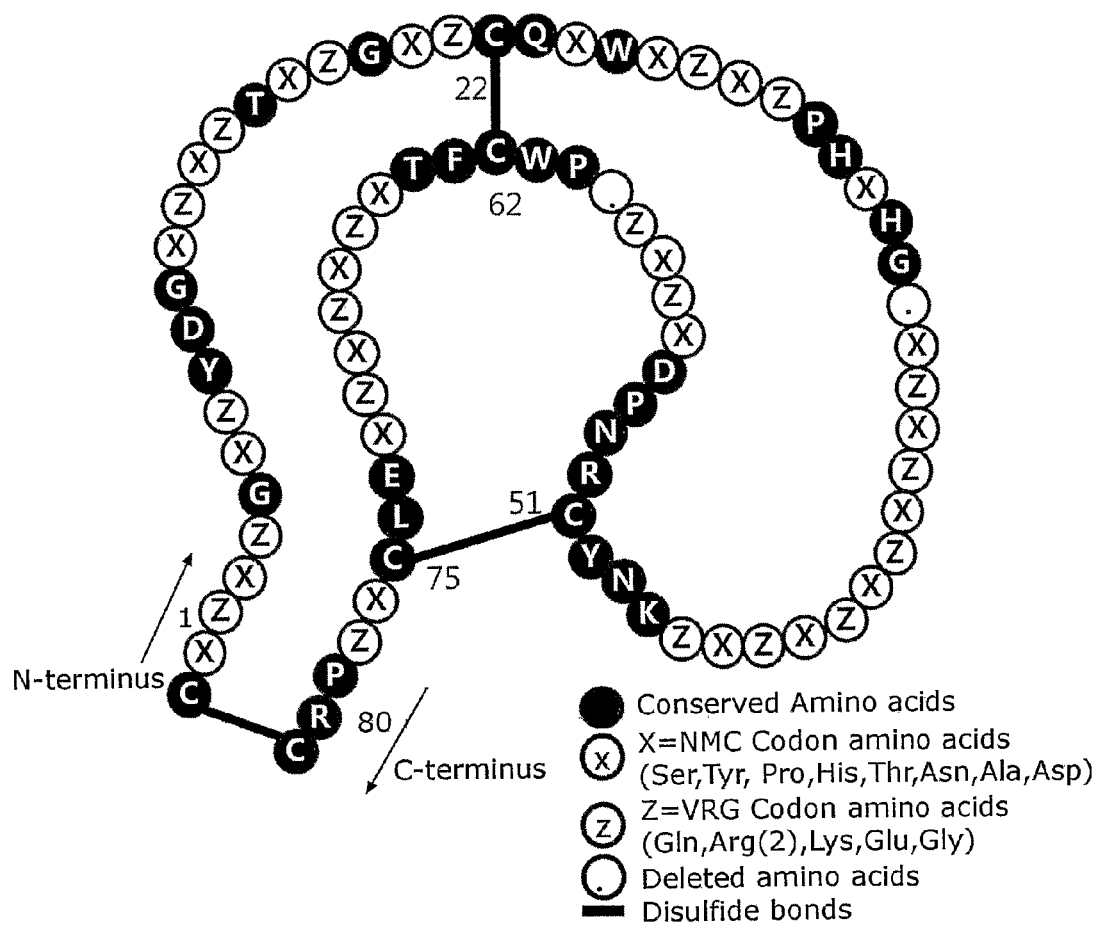
FIG. 5 schematically shows the specific strategy of constructing a Kringle domain library in order to use a protein structural scaffold that may specifically bind to various target molecules, based on the human plasminogen Kringle domain 2.

FIG. 5 schematically shows the specific strategy of constructing a Kringle domain library in order to use a protein structural scaffold that may specifically bind to various target molecules, based on the human plasminogen Kringle domain 2. That is, 6 cysteine residues (C1, C22, C51, C63, C75 and C80), which have the highest conservation rate and form disulfide bonds which are of structural importance, were conserved in an amino acid sequence of the human Kringle domain. Amino acids forming the hydrophobic core in the Kringle domain structure were also conserved (K48, N49, Y50, C51, R52, N53, P54, D55, P61, W62, C63, F64, and T65) (Marti, et al., Biochemistry 38:15741-15755, 1999). In addition, amino acid residues (G6, Y9, D10, G11, T16, G19, Q23, W25, P30, H31, H33, G34, E73, L74, P78 and R79) that have been considered to have a high conservation rate were also conserved. Finally, the Kringle domain s own binding activity was removed to construct a protein structural scaffold having only the specific affinity to target substances. Lysine (Lys) or its analogs bind to binding sites formed by the amino acid residues such as Y36, I37, D55, R56, E57, W62, C63, F64, R71, W72, E73 and L74 (Marti, et al, Biochemistry 38:15741-15755, 1999). The above-mentioned amino acid residues were substituted with other residues, except for the amino acid residues D55, W62, C63, F64, E73 and L74. As a result, the numbers of the mutated amino acid residues were 2, 3, 4, 5, 7, 8, 12, 13, 14, 15, 17, 18, 20, 21, 24, 26, 27, 28, 29, 32, 36, 37, 38, 39, 40, 41, 42, 43, 44, 45, 46, 47, 56, 57, 58, 59, 66, 67, 68, 69, 70, 71, 72, 76, and 77. The mutations at total 45 amino acid residues were induced.

The purpose of constructing a protein scaffold library based on the Kringle domain structure is to isolate variants that specifically bind to different target molecules with high affinity. That is to say, these Kringle domain variants must specifically bind to the target molecules such as biopolymers (protein/nucleic acid/lipid/carbohydrate, etc) and small molecules. For this purpose, a protein scaffold library was designed to be constructed, so that the protein scaffold library includes amino acids Tyr, Ser and Arg that were added upon the somatic hypermutation of an original antibody and amino acids that may form intermolecular non-covalent bonds (hydrogen bonds, ionic bonds, hydrophobic bonds, etc.) may be introduced into each mutation site. For this purpose, amino acids mutated at each residue of the Kringle domain were induced by alternately introducing triplets NMC and VRG The triplet VRG encodes firstly V (V=A, C, or G), secondly R (R=A or G), and thirdly G. Here, the triplet VRG may be substituted with 5 amino acid residues Gln (⅕ insertion probability), Arg (⅖ insertion probability), Lys (⅕ insertion probability), Glu (⅕ insertion probability) and Gly (⅕ insertion probability). The triplet NMC encodes firstly N (N=A, T, C, or G), secondly M (M=A or C), and thirdly C. Here, the triplet NMC may be substituted at the same probability with 8 amino acid residues Ser (⅛ insertion probability), Tyr (⅛ insertion probability), Pro (⅛ insertion probability), H is (⅛ insertion probability), Thr (⅛ insertion probability), Asn (⅛ insertion probability), Ala (⅛ insertion probability), and Asp (⅛ insertion probability). Since such a strategy of constructing an amino acid-substituted library may be used to substitute amino acids having various physicochemical characteristics, it is possible to provide a protein scaffold library based on the Kringle domain structure that may specifically bind to the various target molecules.

Figure 6:
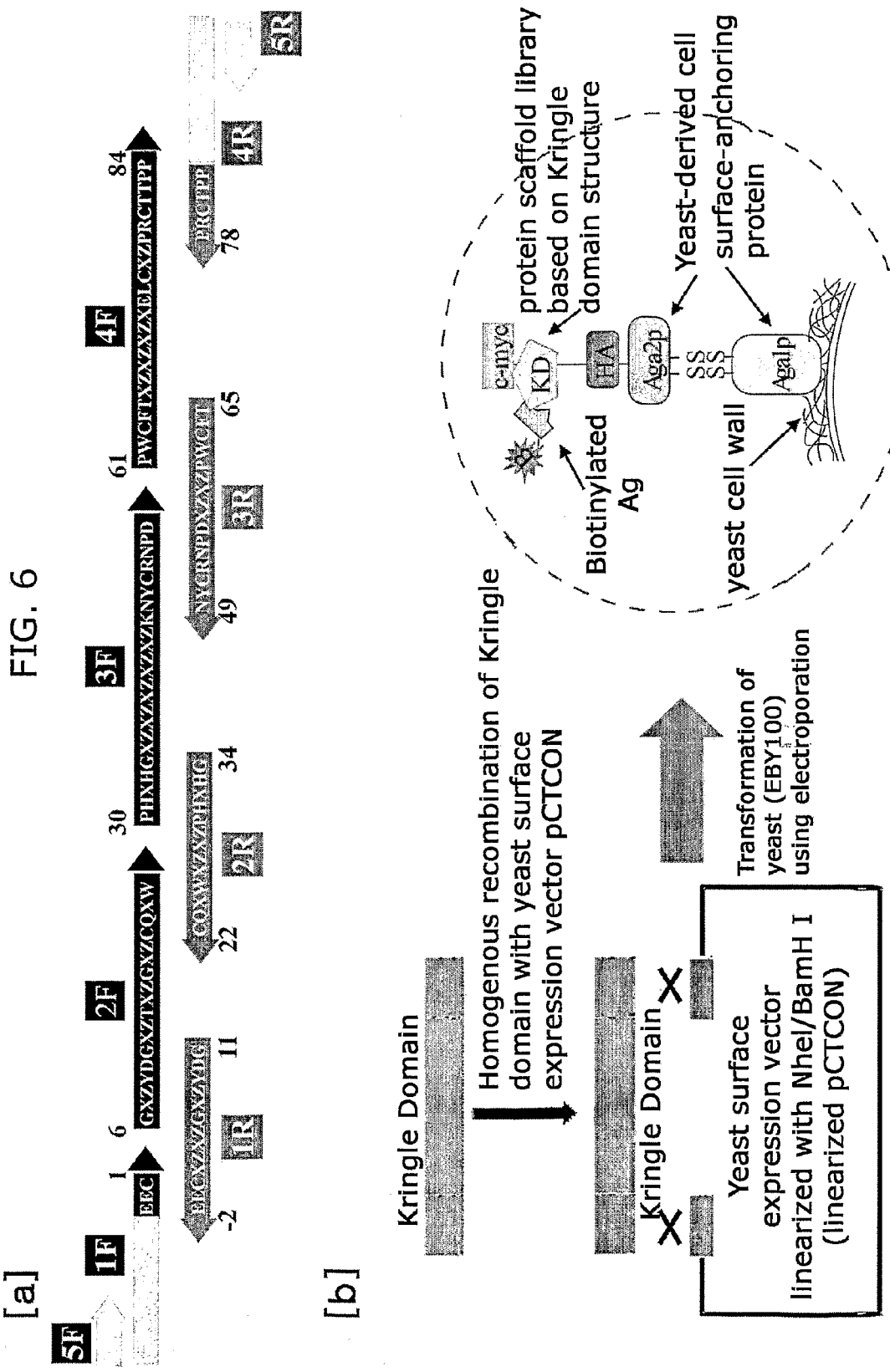
FIG. 6 is a schematic diagram showing procedures of constructing a Kringle domain protein scaffold library.
Figure 7:
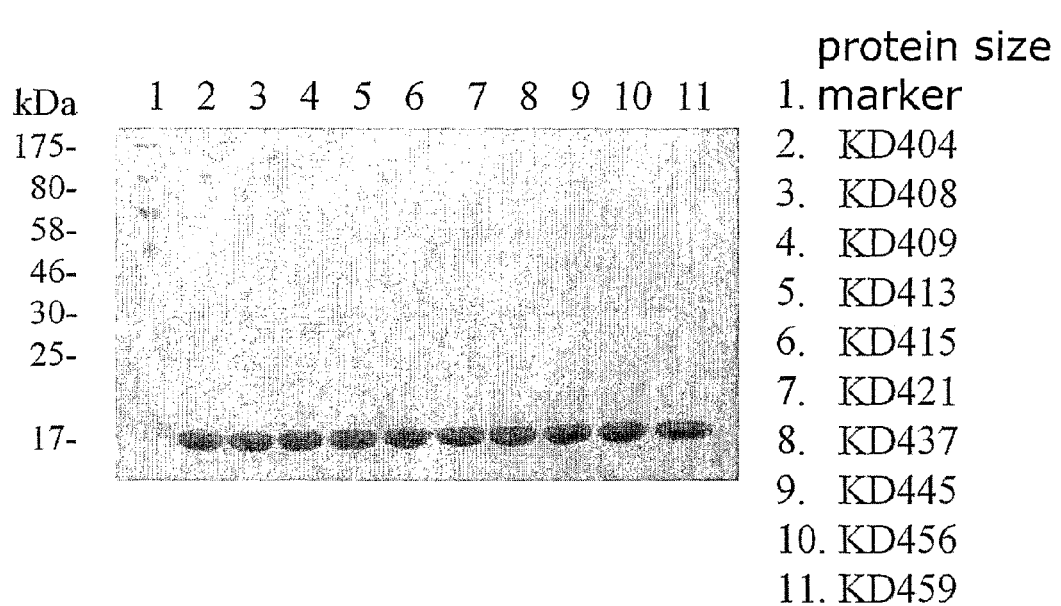
FIGS. 7-12 show the analysis of the screened Kringle variant clones on 15% SDS-PAGE under a reducing (FIGS. 7, 9 and 11) or non-reducing (FIGS. 8, 10 and 12) condition, after purifying screened Kringle variant clones KD404, KD408, KD409, KD413, KD415, KD421, KD437, KD445, KD456 and KD459 with respect to the target molecule DR4; screened Kringle variant clones KD502, KD503, KD505, KD506, KD509, KD537, KD542, KD548, KD555 and KD559 with respect to the target molecule DR5; and screened Kringle variants KDT01, KDT02, KDT08 and KDT26 with respect to the target molecule TNFα.
Figure 8:
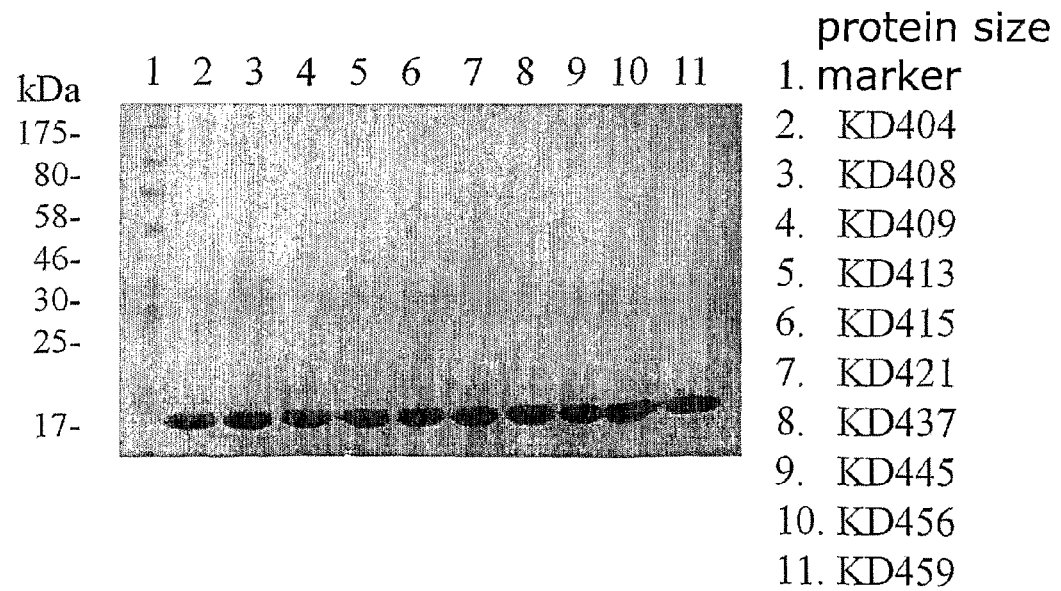
Figure 9:
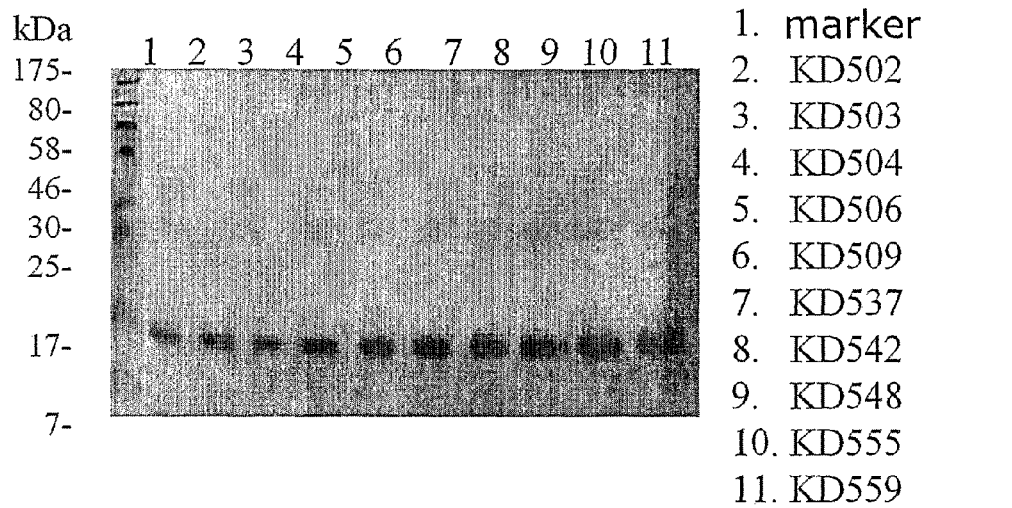
Figure 10:
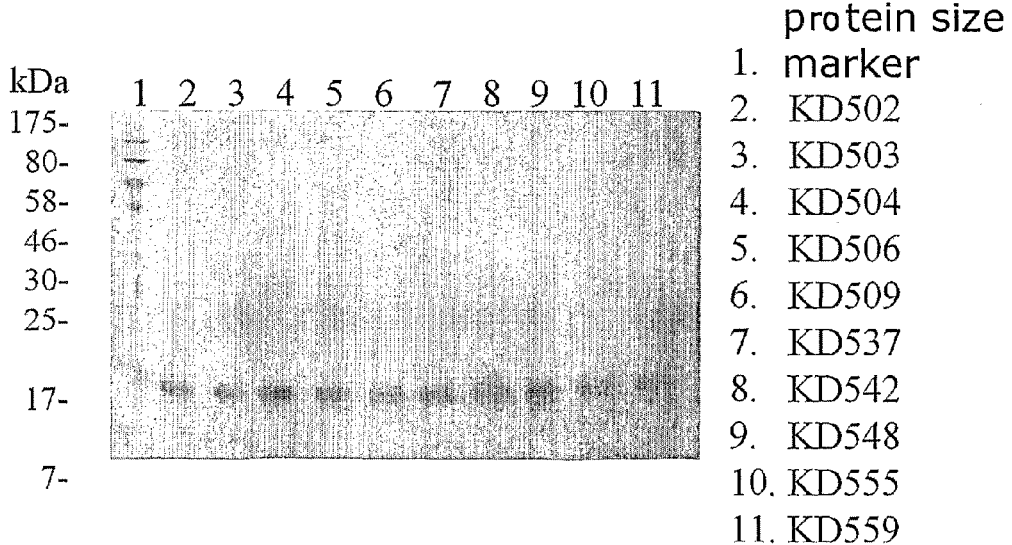
Figure 11:
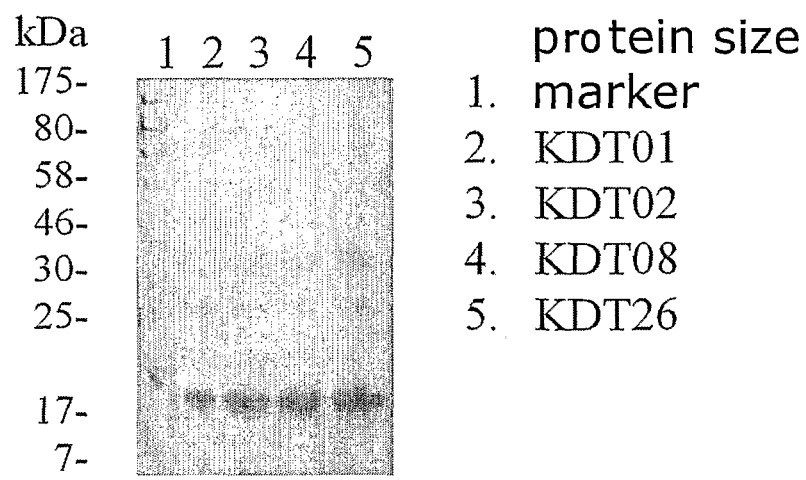
Figure 12:
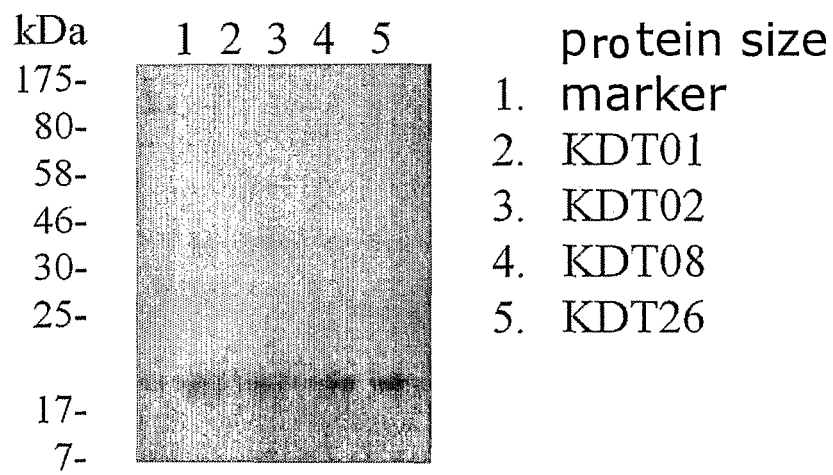

In order to construct the Kringle domain library, 8 primers were designed and used herein (Table 5). The 8 primers have overlapped regions, and all have a melting temperature ($T_m$) of 55° C. or above. The 8 primers (SEQ ID NOs: 1 to 8) were used to perform an overlapping PCR, thereby constructing a Kringle domain library expression vector (FIG. 6) (Lee H W. et al., Biochem Biophys Res Commun, 343:896-903, 2006). In order to amplify genes of the Kringle domain library, a forward primer (SEQ ID NO: 9) and a reverse primer (SEQ ID NO: 10) were used.

In order to transform the human Kringle domain library into yeast using a yeast surface expression vector and homologous recombination mechanism, the amplified human Kringle domain expression vector (10 μg/μl) and the human Kringle domain/yeast surface expression vector (pCTCON, Colby, et al., Methods enzymol, 388:248-258) (1 μg/μl) were mixed together, and electroporated into yeast ten times to construct a library (Lee H W. et al., Biochem Biophys Res Commun, 343:896-903, 2006; Kim Y S. et al., Proteins: structure, function, and bioinformatics, 62:1026-1035, 2006). The size of the Kringle domain library was determined to be $2\times10^6$ cells by serially diluting the library, incubating the library in a selective medium and counting the grown colonies.

TABLE 5

| SEQ ID NOs | Oligonucleotide DNA sequences |
|---|---|
| SEQ ID NO: 1 | 5'-GGT GGT GGT GGT TCT GGT GGT GGT GGT TCT GGT GGT GGT GGT TCT GCT AGC GAG GAA TGT-3' |
| SEQ ID NO: 2 | 5'-GCC GTC ATA CYB GKN TCC CYB GKN CYB GKN ACA TTC CTC GCT AGC AGA AC-3' |
| SEQ ID NO: 3 | 5'-G GGA NMC VRG TAT GAC GGC NMC VRG NMC VRG ACC NMC VRG GGA NMC VRG TGC CAG NWC TGG-3' |
| SEQ ID NO: 4 | 5'-TCC ATG GKN GTG TGG CYB GKN CYB GKN CCA GKN CTG GCA CYB GKN TC-3' |
| SEQ ID NO: 5 | 5'-C VRG CCA CAC NMC CAT GGA NMC VRG NMC VRG NMC VRG NMC VRG NMC VRG NMC VRG AAG AAT TAC TGT CGT AAC CCC GAT-3' |
| SEQ ID NO: 6 | 5'-GGT GAA ACA CCA AGG CYB GKN CYB GKN ATC GGG GTT ACG ACA GTA ATT-3' |
| SEQ ID NO: 7 | 5'-C VRG CCT TGG TGT TTC ACC NMC VRG NMC VRG NMC VRG NMC GAA CTT TGC NMC VRG CCC CGC TGC ACA-3' |
| SEQ ID NO: 8 | 5'-ATC TCG AGC TAT TAC AAG TCC TCT TCA GAA ATA AGC TTT TGT TCG GAT CCT GGA GGT GTT GTG CAG CGG GGC YBG- 3' |
| SEQ ID NO: 9 | 5'-GGT GGT GGT GGT TCT GGT GGT-3' |
| SEQ ID NO: 10 | 5'-ATC TCG AGC TAT TAC AAG TCC TCT TCA G-3' |

The oligonucleotide DNA sequences used to construct a Kringle domain library are listed in Table 5.

Example 4

Analysis of Protein Scaffold Library Based on the Kringle Domain Structure

In order to determine whether the protein scaffold library where as a scaffold, the Kringle domain 2 gene of the plasminogen was constructed is constructed as designed above, the transformed yeast surface expression vector was randomly recovered from the constructed yeast library to analyze a nucleotide sequence of the inserted Kringle domain (Lee H W. et al, Biochem Biophys Res Commun, 343:896-903, 2006; Kim Y S. et al., Proteins: structure, function, and bioinformatics, 62:1026-1035, 2006). The nucleotide sequence was analyzed using a forward primer (SEQ ID NO: 11=5'-GTT CCA GAC TAC GCT CTG CAG G-3') and a reverse primer (SEQ ID NO: 12=5'-GAT TTT GTT ACA TCT ACA CTG TTG-3'), and its amino acid sequence was determined by means of the standard codes. The nucleotide sequence of the Kringle domain library was proven to be SEQ ID NO: 13 as determined in the desired library construction method. DNA sequences of clones that were randomly selected from the Kringle domain library to determine their nucleotide sequences were SEQ ID NOs: 14 to 18. The SEQ ID NOs: 14 to 18 were included in the nucleotide sequence of the Kringle domain library, and it was confirmed that the Kringle domain library was constructed as designed above by analyzing some nucleotide sequence of the Kringle domain library.

TABLE 6

| SEQ ID NOs | DNA sequence |
|---|---|
| SEQ ID NO: 13 | 5'-TGT NMC VRG NMC VRG GGA NMC VRG TAT GAC GGC NMC VRG NMC VRG ACC NMC VRG GGA NMC VRG TGC CAG NMC TGG NMC VRG NMC VRG CCA CAC NMC CAT GGA NMC VRG NMC VRG NMC VRG NMC VRG NMC VRG AAG AAT TAC TGT CGT AAC CCC GAT NMC VRG NMC VRG CCT TGG TGT TTC ACC NMC VRG NMC VRG NMC VRG NMC GAA CTT TGC NMC VRG CCC CGC TGC-3' |
| SEQ ID NO: 14 | 5'-TGT AAC GGG GAC GGG GGA GAC AGG TAT GAC GGC AAC AAG CAC AAG ACC CTC AAG GGA TAC CGG TGC CAG CAC TGG ACC AGG ACC AAG CCA CAC CAC CAT GGA CAC CGG GAC AAG ATC CGG TAC AGG GAC CAG AAG CAT TAC TGT CGT AAC CCC GAT ACC GAG ACC GGG CCT TGG TGT TTC ACC AAC AAG AAC GGG GAC AGG TAC GAA CTT TGC CAC GAG CCC CGC TGC-3' |
| SEQ ID NO: 15 | 5'-TGT AAC CAG CAC AAG GGA TCC AGG TAT GAC GGC CAC AAG AAC CGG ACC GTC AAG GGA AAC CAG TGC CAG GAC TGG TAC AAG CCC CAG CCA CAC TTC CAT GGA CTC AGG GAC AAG TCC AAG AAC AAG TTC AAG TTC AAG AAG AAT TAC TGT CGT AAC CCC GAT GCC AGG ACC AGG CCT TGG TGT TTC ACC CAC GAG GAC AAG GAC GAG TAC GAA CTT TGC GAC GGG CCC CGC TGC-3' |

TABLE 6-continued

| SEQ ID NOs | DNA sequence |
|---|---|
| SEQ ID NO: 16 | 5'-TGT CCC GAG GAC CAG GGA GAC GAG TAT GAC GGC CAC GAG CAC AAG ACC CAC AGG GGA AAC AGG TGC CAG TCC TGG TAC AGG CCC AAG CCA CAC AAC CAT GGA CAC AGG ATC AAG GAC CGG TAC AAG TAC AAG GTC AAG AAG AAT TAC TGT CGT AAC CCC GAT ACC CAG GCC CGG CCT TGG TGT TTT ACC AAC CGG CAC AGG GAC GAG CAC GAA CTT TGC GAC CAG CCC CGC TGC-3' |
| SEQ ID NO: 17 | 5'-TGT ACC AAG CAC CGG GGA ACC AAG TAT GAC GGC CAC AAG AAC AGG ACC TAC CAG GGA AAC AGG TGC CAG AAC TGG TCC CGG AAC AAG CCA CAC CAC CAT GGA GAC AAG TAC GAG AAC AAG TTC CGG GCT CGG CCT CAA GAA GAA TTA CTG TCG TAA CCC CGA TGA CAA GGC CGA GCC TTG GTG TTT ACC GGA CGG GGA CAG GAA CGG GAT CGA ACT TTG CTC AAG CCC CGC TGC-3' |
| SEQ ID NO: 18 | 5'-TGT ACC CAG CCC GAG GGA CCC AGG TAT GAC GGC AAC GGG CAC AAG ACC CAC CGG GGA CAC CAG TGC CAG GCC TGG CCC AAG GCC CGG CCA CAC GAC CAT GGA CTC AAG CAC AGG GAC AGG CTC CAG GTC CGG GAC AAG AAG AAT TAC TGT CGT AAC CCC GAT GCC GAG GAC GGG CCT TGG TGT TTC ACC CAC CGG CAC GGG TAC GGG CAC GAA CTT TGC GAC GGG CCC CGC TGC-3' |

The DNA sequences of the constructed protein scaffold library based on the Kringle domain structure are listed in Table 6.

Example 5

Preparation of Various Target Molecules

It was investigated whether monomers, which specifically bind to various target molecules, from the protein scaffold library based on the Kringle domain structure constructed in Example 4 are isolated and screened. As the model target molecules, a human-derived cell death receptor 5 (TRAIL-receptor 2, hereinafter referred to as 'DR5', a cell death receptor 4 (TRAIL-receptor 1, hereinafter referred to as 'DR4', and TNFα were used.

The expression and purification of the target molecules (DR4, DR5 and TNFα were described in detail in the thesis already published by this applicant (Lee H W et al, Biochem Biophys Res commun, 330:1205-1212; Kim M S. et al., J Mol Biol, 374:1374-1388, 2007). In the case of the target molecule DR4, an extracellular domain (amino acid residues 1-216) of DR4 was cloned in frame into a bacterial expression vector using the restriction enzymes NheI/HindIII (Lee H W. et al., Biochem Biophys Res commun, 330:1205-1212). In this case, the bacterial expression vector was designed to contain a sequence of T7 promotor-DR4-6×His tag (pCRT7NT-TOPO). In the case of the target molecule DR5, an extracellular domain (amino acid residues 1-130) of DR5 was cloned in frame into a bacterial expression vector using the restriction enzymes NheI/XhoI (Lee H W. et al., Biochem Biophys Res commun, 330:1205-1212). In this case, the bacterial expression vector was designed to contain a sequence of T7 promotor-DR5-6×His tag (pET21b, (Invitrogen, USA)). In the case of the target molecule TNFα an extracellular domain (amino acid residue 1-157) of TNFα was cloned in frame into a bacterial expression vector using the restriction enzymes NheI/HindIII (Kim M S. et al., J Mol Biol, 374: 1374-1388, 2007). In this case, the bacterial expression vector was designed to contain a sequence of T7 promotor-TNFα 6×His tag (pET23d, Invitrogen, USA).

All the target substances were expressed using the same method. E. coli cells were cultured at 37° C. until $OD_{600}$ reaches a value of approximately 0.6. Then, 1 mM isopropyl-β-D-thiogalactopyranoside (IPTG SIGMA-ALDRICH Co., USA) was added to the E. coli cells to facilitate the protein expression, and the E. coli cells were then further incubated at 30° C. for 10 hours. The E. coli cells were collected using a centrifuge (Mega 21R, (Hanil, orea)), and homogenized using ultrasonic waves (SONICS, Vibra Cell™, USA). Only an E. coli homogenate-free supernatant was obtained using a centrifuge (Mega 21R, (Hanil, Korea)), and the target substance was purified using Talon resin (Clontech, Inc., USA) that specifically effectively purifies a His-tag protein. When the purified target substance was run on SDS-PAGE, DR4, DR5 and TNFα had molecular weights of approximately 16 kDa, 16 kDa and 17 kDa, respectively, and were purified with a purity of 90% or more.

In order to determine the activities of the purified target substances such as DR4, DR5 and TNFα the activities of the DR4 and DR5 were determined by confirming the affinity to TRAIL using surface plasmon resonance (SPR) technology (Biacore2000, GE Healthcare Co., United Kingdom), and the activity of the TNFα was determined by confirming the affinity to REMICADE (infliximab, Centocor, Inc., USA).

Example 6

Separation of Monomers that Specifically Bind to Various Target Molecules from Protein Scaffold Library Based on the Kringle Domain Structure (Screening of Anti-DR4, -DR5 and TNFα Kringle Domains)

In order to screen Kringle domains having a high specific affinity to the target substances, DR4, DR5 and TNFα from the Kringle domain library, the target substances, DR4, DR5 and TNFα which were purified in Example 5, were biotinylated using an EZ-LINK™ Sulfo-NHS-LC-Biotinylation kit (Pierce Inc., USA), and then reacted at 37 r for 1 hour with the Kringle domain library that was expressed on a yeast cell surface. The Kringle domain library, which was reacted with the biotinylated target substance and expressed on a yeast cell surface, was reacted with Anti-Biotin MACIBead™ (130-091-147, Miltenyi Biotec Inc., Germany) at 4° C. for 20 minutes, and then enriched in yeast expressing the Kringle domain, which had a high affinity to the target substances DR4, DR5 and TNFα on the yeast cell surface using a magnetic activated cell sorting (MACS) method (enrichment). Then, the MACS method was sequentially performed three times, followed by sequentially performing a fluorescence activated cell sorting (FACS) method three times. The FACS method was performed, as follows. Target substances DR4, DR5 and TNFα purified from bacteria were biotinylated using an EZ-LINK™ Sulfo-NHS-LC-Biotinylation kit (Pierce Inc., USA). Then, PE-conjugated streptavidin (streptavidin-R-phycoerythrin conjugate (SA-PE), Molecular Probes (Eugene, USA)) was secondarily attached respectively to the target substances, and the resulting target substances were analyzed using a fluorescence activated cell sorting (FACS) method.

The Kringle domain library was primarily attached to mouse-derived anti-c-myc 9e10 mAb (Ig Therapy, Korea), so that it can be expressed with a c-myc tag on the yeast cell surface, and secondarily stained with FITC-conjugated anti-mouse antibody (mAb, Sigma), thus to measure an expression level of the Kringle domain library.

In order to sequentially subject the Kringle domain variant library to MACS and FACS methods to screen Kringle domain variant clones having a high specific affinity to the target substances DR4, DR5 and TNFα each of the MACS and FACS methods was performed, and the affinity to a 100 nM biotinylated target molecule was analyzed using FACS. Also, as a control, the affinities to the plasminogen Kringle domain 2 and the protein scaffold library prior to the screening were analyzed.

Clones having a high affinity/specificity for each target molecule were enriched by the above-mentioned high-speed screening method, and respective clones were finally obtained (Lee H W et al., Biochem Biophys Res commun, 330:1205-1212; Kim M S. et al., J Mol Biol, 374:1374-1388, 2007).

The Kringle domain variant clones KD404, KD408, KD409, KD413, KD415, KD421, KD437, KD445, KD456 and KD459, which have a high specific affinity to the target molecule DR4, were isolated.

The Kringle domain variant clones KD502, KD503, KD505, KD506, KD537, KD542, KD548, KD555, KD558 and KD559, which have a high specific affinity to the target molecule DR5, were isolated.

The Kringle domain variant clones KRT01, KRT02, KRT08 and KRT26, which have a high specific affinity to the target molecule TNFα were isolated.

Plasmids were recovered from the yeast clones having a high specific affinity to each target molecule to determine DNA sequences and amino acid sequences of the Kringle domain variants. The DNA sequence was analyzed using a forward primer (SEQ ID NO: 11) and a reverse primer (SEQ ID NO: 12), and the amino acid sequence was determined by means of the standard codes.

The amino acid sequences and conserved amino acid sequences of the respective clones screened with respect to each of the target molecules DR4, DR5 and TNFα were listed in Table 6. According to the strategy of constructing a Kringle domain library construct, each amino acid should occur at site X with the probability of 12.5% and occur at site Z with the probability of 16.7% when the amino acids are randomly mutated (FIG. 4). However, the amino acid sites were present, which are not randomly mutated but have a tendency to be mutated with high probability as listed in Table 6.

N-glycosylation of the anti-DR4, -DR5 and -TNFα Kringle domain variants was analyzed based on the amino acid sequence analysis of the Kringle domain variants. As a result, the KD404 Kringle domain variant had one N-glycosylation site. Isoelectric points (pI) of the anti-DR4, -DR5 and -TNFα Kringle domain variants, which were analyzed based on the amino acid sequence analysis of the Kringle domain variants, were in a range of approximately PH 8.0 in all the clones (Expasy assay, Webpage: www.expasy.org).

Example 7

Expression and Purification of Anti-DR4, -DR5 and -TNFα Protein Scaffold Variant Based on Kringle Domain Structure Among the protein scaffold variants based on the Kringle domain structure, anti-DR4 variants (KD404, KD408, KD409, KD413, KD415, KD421, KD437, KD445, KD456, and KD459), anti-DR5 variants (KD502, KD503, KD505, KD506, KD509, KD537, KD542, KD548, KD555, and KD559), and anti-TNFα variants (KDT26, KDT01, KDT02, and KDT08) were cloned in frame into a yeast *Pichia pastoris* expression vector (pPICZaA, Invitrogen, USA), respectively, using the restriction enzymes NheI/BamHI. In this case, the *Pichia* yeast expression vector was designed to contain a sequence of AOX3 promotor-Mfa-secreting targeting sequence-Kringle domain-myc tag-6×His tag (pPICZaA, Invitrogen, USA).

The expression was performed, as follows. yeast (*Pichia pastoris*-GS115, Invitrogen, USA) was incubated at 30° C. in a BMGY medium (buffered complex glycerol, 1% yeast extract (Becton, Dickinson and Company, USA)+2% peptone (Becton, Dickinson and Company, USA)+1.34% yeast nitrogen base (Becton, Dickinson and Company, USA)+100 mM pH 6.0 potassium phosphate (SIGMA-ALDRICH Co., USA)+1% glycerol (BIO BASIC Inc., Canada)) until $OD_{600}$ reaches a value of approximately 15-20, and further incubated for 3 days in a BMMY medium (buffered complex methanol, 1% yeast extract (Becton, Dickinson and Company, USA)+2% peptone (Becton, Dickinson and Company, USA)+1.34% yeast nitrogen base (Becton, Dickinson and Company, USA)+100 mM pH 6.0 potassium phosphate (SIGMA-ALDRICH co., USA)+0.5% Methanol (Merck & Co., Inc. USA)), while adding 0.5% methanol to the medium every 24 hours, for the protein expression. The expressed protein was purified from supernatants, and Talon resin (Clontech, Inc., USA) that specifically effectively purifies 6×His-tag protein was used herein.

FIGS. 7-12 show the purification of screened Kringle variant clones KD404, KD408, KD409, KD413, KD415, KD421, KD437, KD445, KD456 and KD459 with respect to the target molecule DR4, screened Kringle variant clones KD502, KD503, KD505, KD506, KD509, KD537, KD542, KD548, KD555 and KD559 with respect to the target molecule DR5, and screened Kringle variants KDT01, KDT02, KDT08 and KDT26 with respect to the target molecule TNFα and the analysis of the screened Kringle variant clones on 15% SDS-PAGE under a reducing (FIGS. 7, 9 and 11) or non-reducing (FIGS. 8, 10 and 12) condition. The Kringle domains were purified with a purity of 98% or more. All the purified Kringle domains showed a molecular weight of approximately 13 kDa on both reducing and non-reducing SDS-PAGE. This indicates that the expressed and purified Kringle domains are present in the form of monomers in solution state without forming dimers or oligomers by means of artificial disulfide bonds. The concentration and amount of the Kringle domains were quantified using Bradford and BCA methods.

Figure 13:
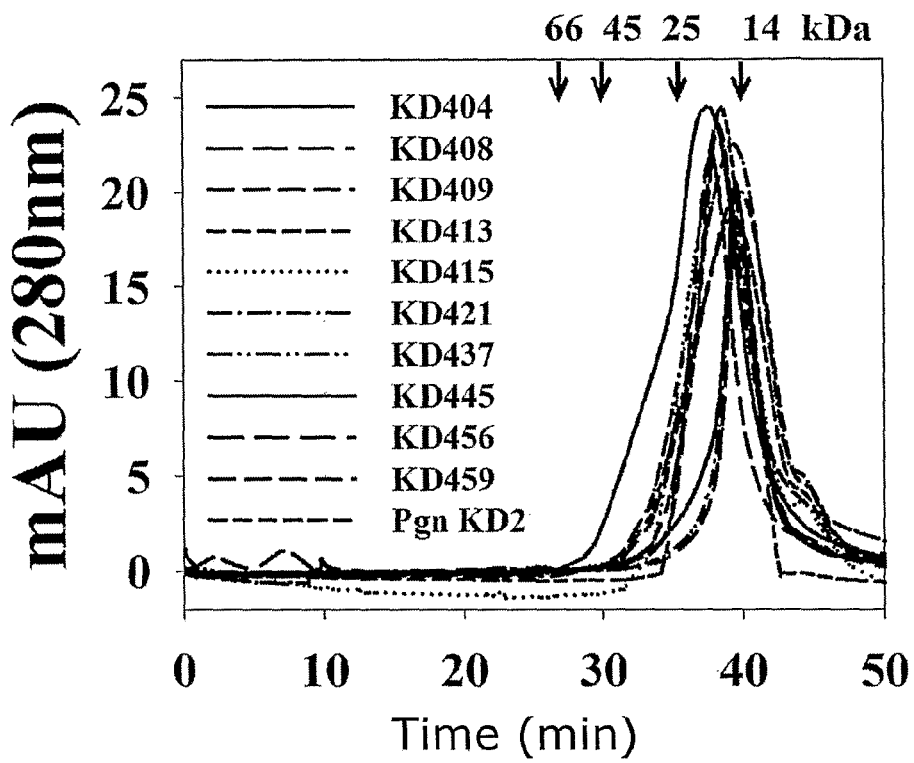
FIGS. 13-15 show the experimental results of size exclusion chromatography column (Superdex™ 200 10/300GC, GE Healthcare, Sweden) in order to confirm whether the anti-DR4, -DR5 and -TNFα Kringle domains are present in the form of monomers using high performance liquid chromatography (HPLC, The Agilent 1200 Series LC Systems and Modules, Agilent, USA).
Figure 14:
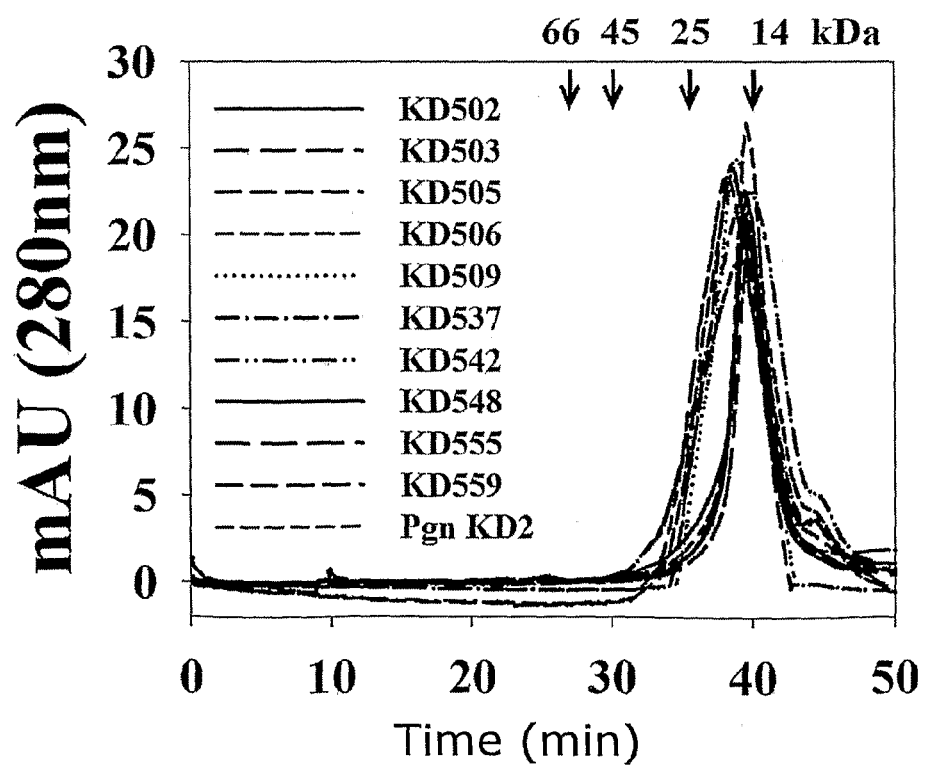
Figure 15:
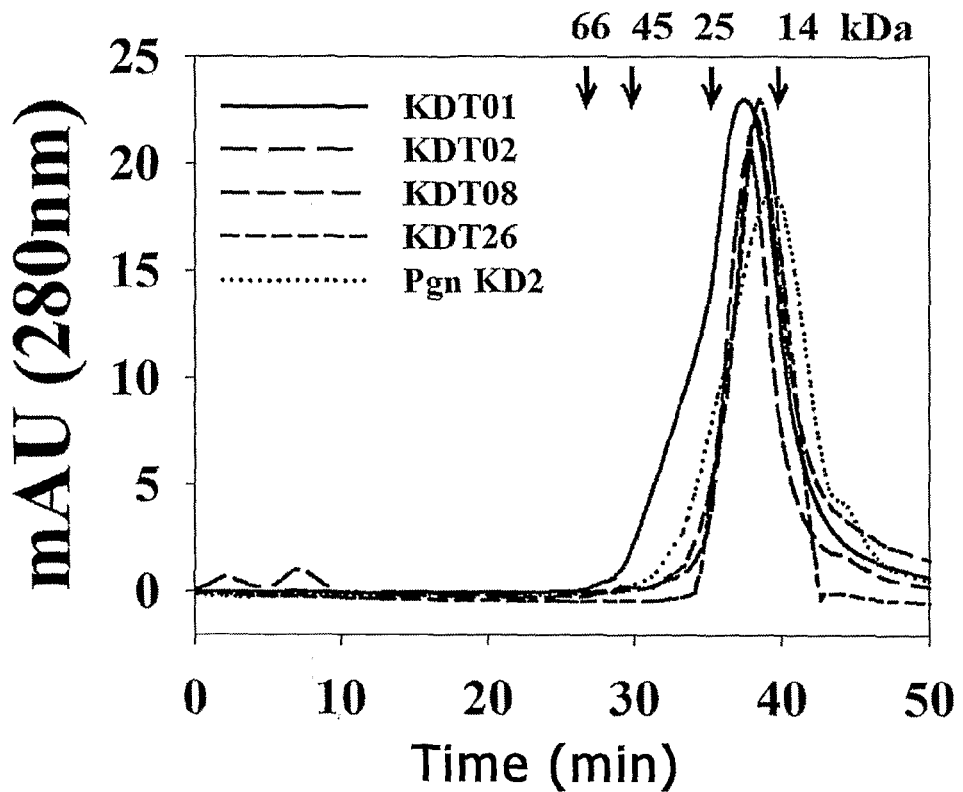

FIGS. 13-15 show the experimental results of size exclusion chromatography column (Superdex™ 200 10/300GC, GE Healthcare, Sweden) in order to confirm whether the anti-DR4, -DR5 and -TNFα Kringle domains are present in the form of monomers, using high performance liquid chromatography (HPLC, The Agilent 1200 Series LC Systems and Modules, Agilent, USA). PBS (pH7.4, 137 mM NaCl, 10 mM Phosphate, 2.7 mM KCl, SIGMA-ALDRICH co., USA) was used as an elution buffer, and its flow rate was 0.5 ml/min. Albumin (66 kDa), ovalbumin (45 kDa), chymotrypsinogen (25 kDa) and ribonuclease A (13.7 kDa) were used as the protein size marker. Since one heights was observed in all the Kringle variant clones, it was revealed that the anti-DR4, -DR5 and -TNFα Kringle domains were present in the form of monomers.

Example 8

Measurement of Affinity, Cross Reactivity and Analysis of Binding Sites of Protein Scaffold Variants Based on the Kringle Domain Structure to Anti-DR4, -DR5 and TNFα

In order to measure the affinity and cross reactivity of the anti-DR4, -DR5 and -TNFα protein scaffold variants based on the Kringle domain structure to the target molecules, an enzyme-linked immunosorbent assay (ELISA) was performed. The target molecules DR4, DR5, TNFα and DcR1, DcR2 were attached to a 96 well EIA/RIA plate (COSTARCorning In., USA) by its reaction at 37° C. for 1 hour, and washed three times with 0.1% PBST (0.1% Tween20, pH 7.4, 137 mM NaCl, 10 mM Phosphate, 2.7 mM KCl, SIGMA-ALDRICH Co., USA) for 10 minutes. The target molecules were attached for 1 hour to a 96 well EIA/RIA plate in 1% PBSB (1% BSA, pH 7.4, 137 mM NaCl, 10 mM Phosphate, 2.7 mM KCl, SIGMA-ALDRICH Co., USA), and then washed three times with 0.1% PBST (0.1% Tween 20, pH 7.4, 137 mM NaCl, 10 mM Phosphate, 2.7 mM KCl, SIGMA-ALDRICH Co., USA) for 10 minutes. Then, the anti-DR4, -DR5 and -TNFα Kringle domain variants were bound, and washed three times with 0.1% PBST for 10 minutes. The anti-DR4, -DR5 and -TNFα Kringle domain variants were primarily bound to mouse-derived anti-c-myc 9e10 mAb (Ig Therapy, Korea), and secondarily bound to alkaline phosphatase (AP)-conjugated anti-mouse mAb (Sigma). Each of the Kringle domain variants was reacted with p-Nitrophenyl palmitate (pNPP, Sigma-aldrich Co., USA) and quantified at an absorbance of 405 nm.

Figure 16:
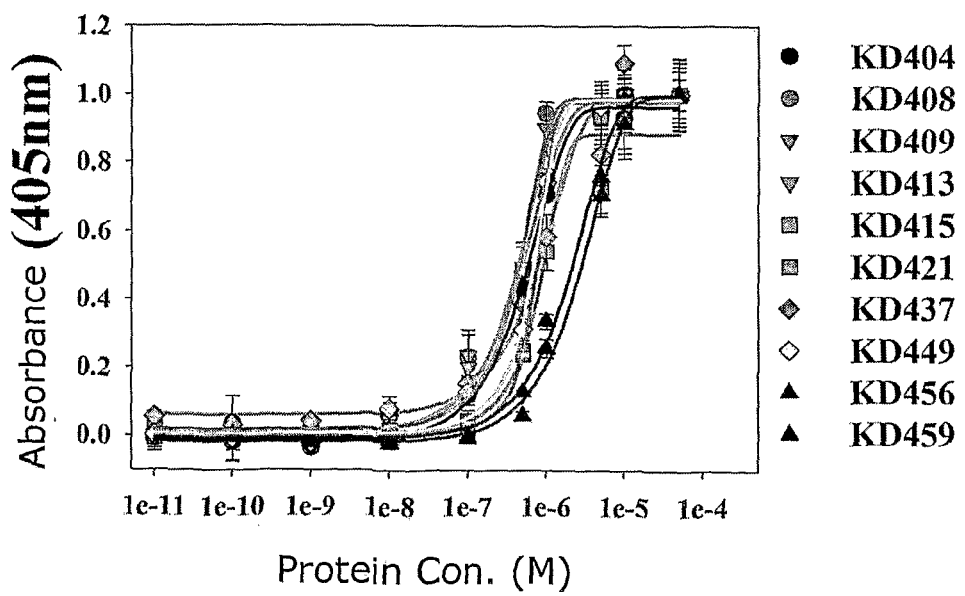
FIGS. 16-18 show the quantitative analysis of affinities of the screened KD404, KD408, KD409, KD413, KD415, KD421, KD437, KD445, KD456, KD459 Kringle domain variant clones to the target molecule DR4, the screened KD502, KD503, KD505, KD506, KD509, KD537, KD542, KD548, KD555, KD559 Kringle domain variant to the target molecule DR5, and the screened KDT01, KDT02, KDT08, KDT26 Kringle domain variants to the target molecule TNFα by using ELISA.
Figure 17:
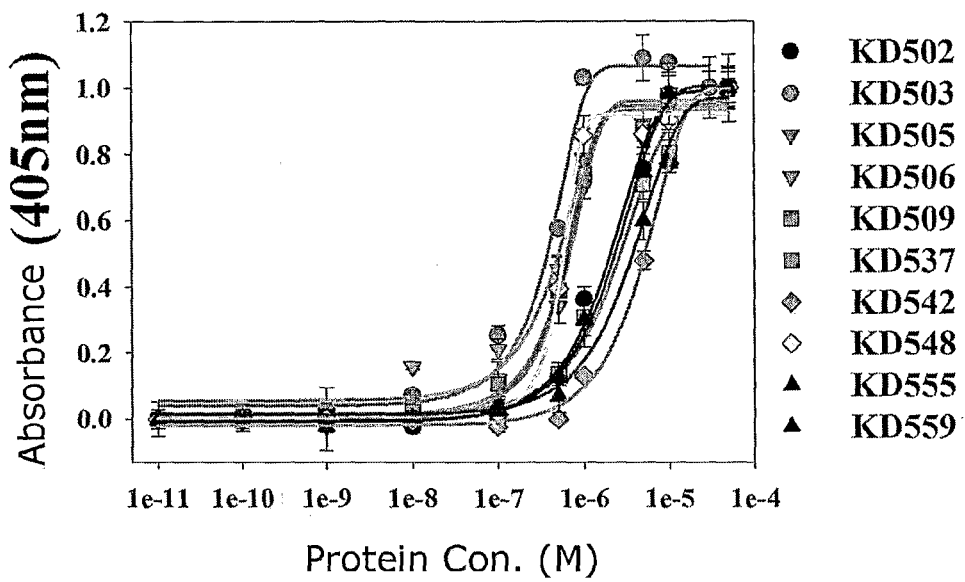
Figure 18:
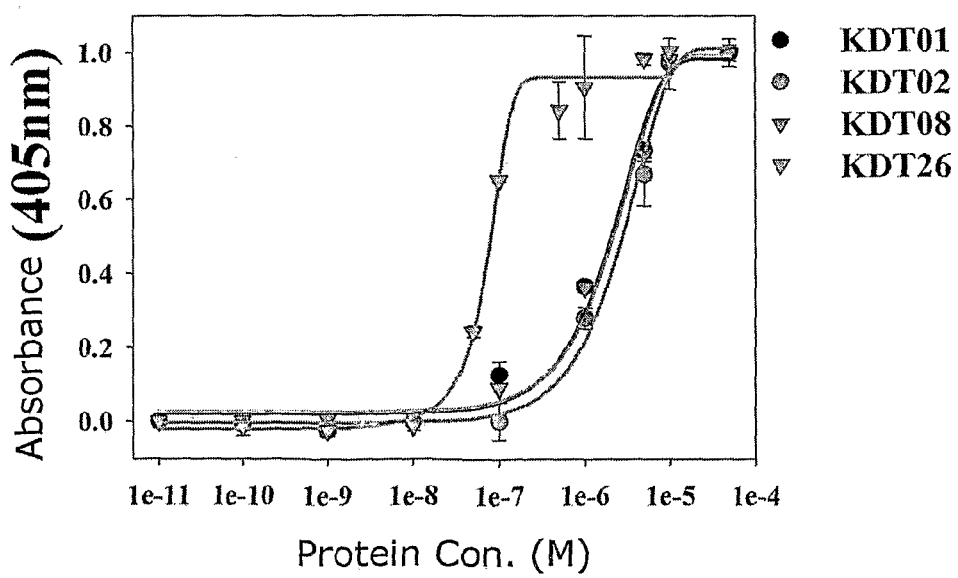

FIGS. 16-18 show the quantitative analysis of affinities of the KD404, KD408, KD409, KD413, KD415, KD421, KD437, KD445, KD456, KD459 Kringle variant clones screened to the target molecule DR4, the KD502, KD503, KD505, KD506, KD509, KD537, KD542, KD548, KD555, KD559 Kringle variant clones screened to the target molecule DR5, and the KDT01, KDT02, KDT08, KDT26 Kringle variants screened to the target molecule TNFα by using ELISA. FIG. 16 shows the quantitative analysis of the affinities of the screened clones to the target molecule DR4, by using ELISA. Affinity was measured at a level of 292 nM to 3794 nM. FIG. 17 shows the quantitative analysis of the affinities of the screened clones to the target molecule DR5, by using ELISA. Affinity was measured at a level of 294 nM to 5396 nM. FIG. 18 shows the quantitative analysis of the affinities of the screened clones to the target molecule TNFα by using ELISA. Affinity was measured at a level of 29 nM to 3829 nM.

Figure 19:
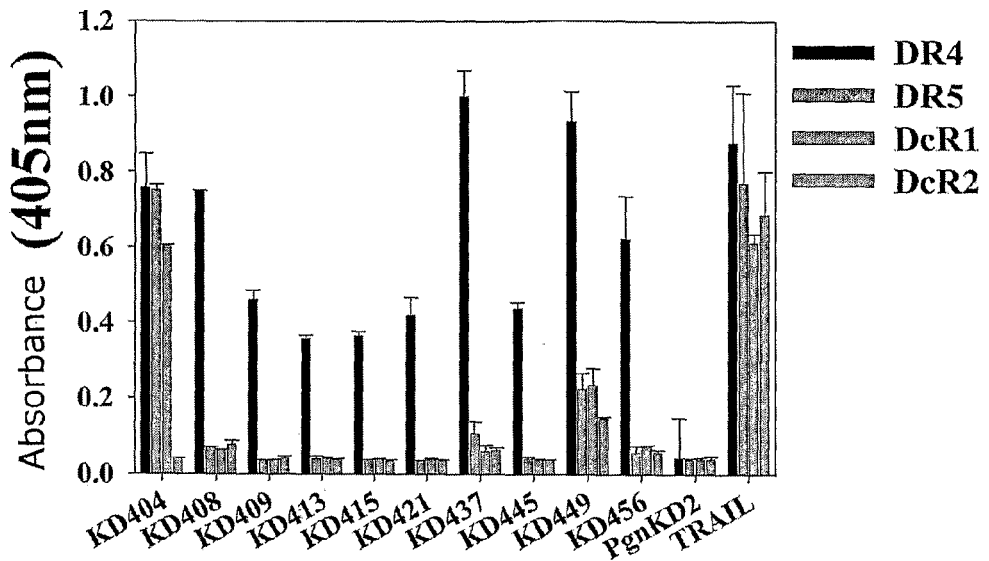
FIGS. 19-21 show the quantitative analysis of cross reactivity of the screened KD404, KD408, KD409, KD413, KD415, KD421, KD437, KD445, KD456, KD459 Kringle domain variants with the target molecule DR4, the screened KD502, KD503, KD505, KD506, KD509, KD537, KD542, KD548, KD555, KD559 Kringle domain variants with the target molecule DR5, and the screened KDT01, KDT02, KDT08, KDT26 Kringle domain variants with the target molecule TNFα by using ELISA.
Figure 20:
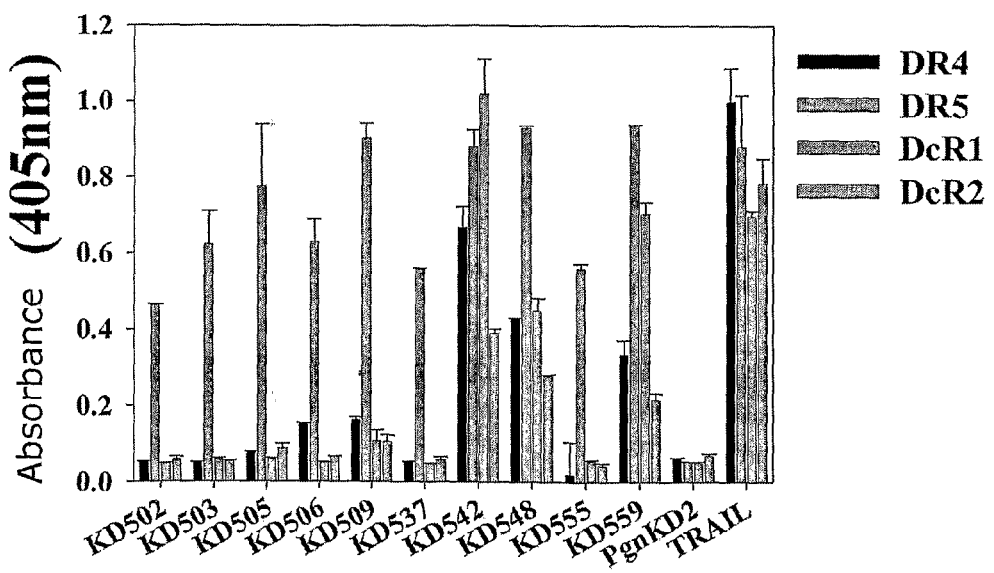
Figure 21:
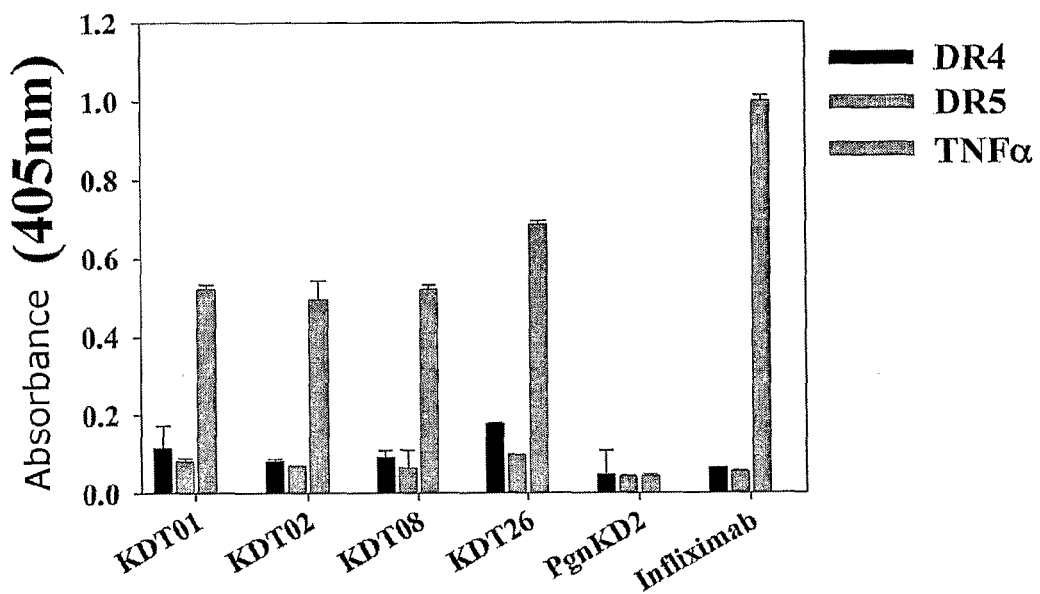

FIGS. 19-21 shows the quantitative analysis of cross reactivity of the KD404, KD408, KD409, KD413, KD415, KD421, KD437, KD445, KD456, KD459 Kringle domain variants screened to the target molecule DR4, the KD502, KD503, KD505, KD506, KD509, KD537, KD542, KD548, KD555, KD559 Kringle domain variants screened to the target molecule DR5, and the KDT01, KDT02, KDT08, KDT26 Kringle domain variants to the target molecule TNFα by using ELISA. FIG. 19 shows the quantitative analysis of the cross reactivity on the DcR1, DcR2, DR4 and DR5 of the screened clones against the target molecule DR4 using ELISA. Most of the clones specifically bound to the target molecule DR4. The KD404 Kringle variant clone had a strong cross reactivity with DcR1 and DR5, and the KD449 Kringle variant clone had a weak cross reactivity with other target molecules. This indicates that since most of the Kringle domain variants screened with respect to DR4 bind only to the target molecule but have no binding affinity to the other molecules or weakly bind to the other molecules, they have no cross reactivity. FIG. 20 shows the quantitative analysis of the reactivity on the DcR1, DcR2, DR4 and DR5 of the screened clones against the target molecule DR5, by using ELISA. Most of the clones specifically bound to the target molecule DR5. The KD542, KD548 and KD559 Kringle variant clones had the cross reactivity with other target molecules. This indicates that since most of the Kringle domain variants screened with respect to DR5 bind only to the target molecule but have no binding affinity to the other molecules or very weakly bind to the other molecules, they have no cross reactivity. FIG. 21 shows the quantitative analysis of the reactivity on TNFα, DR4 and DR5 of the clones, KDT01, KDT02, KDT08, and KDT26, screened against the target molecule TNFα by using ELISA. All the anti-TNFα Kringle domain variants specifically bound to the target molecule TNFα This indicates that since most of the Kringle domain variants screened with respect to TNFα bind only to the target molecule but have no binding affinity to the other molecules or very weakly bind to the other molecules, they have no cross reactivity.

Figure 22:
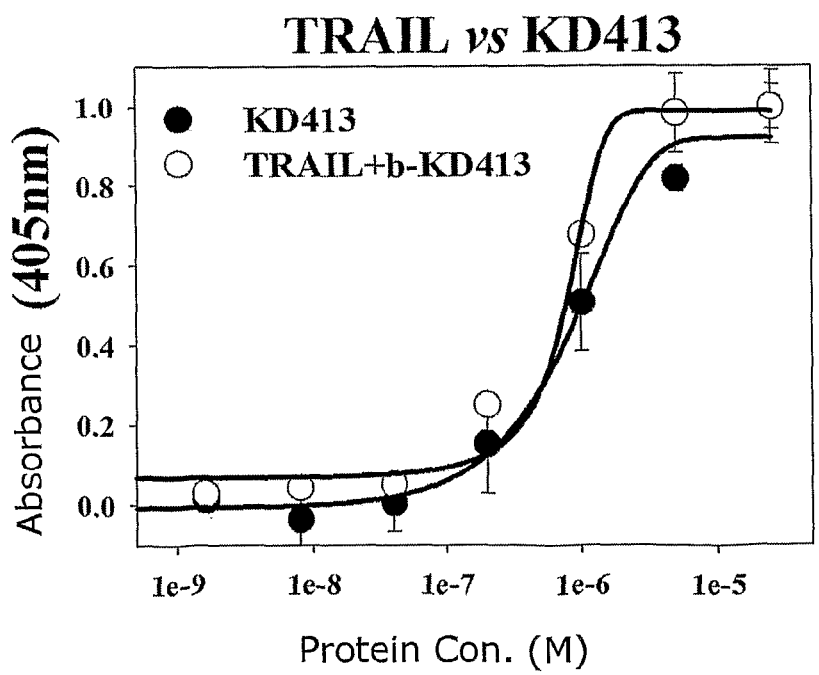
FIGS. 22-27 show the analysis of each binding site of the screened anti-DR4 and -DR5 Kringle domain variants to target molecules such as TRAIL in order to compare the binding sites of the anti-DR4 and -DR5 Kringle domain variants, by using competitive ELISA.
Figure 23:
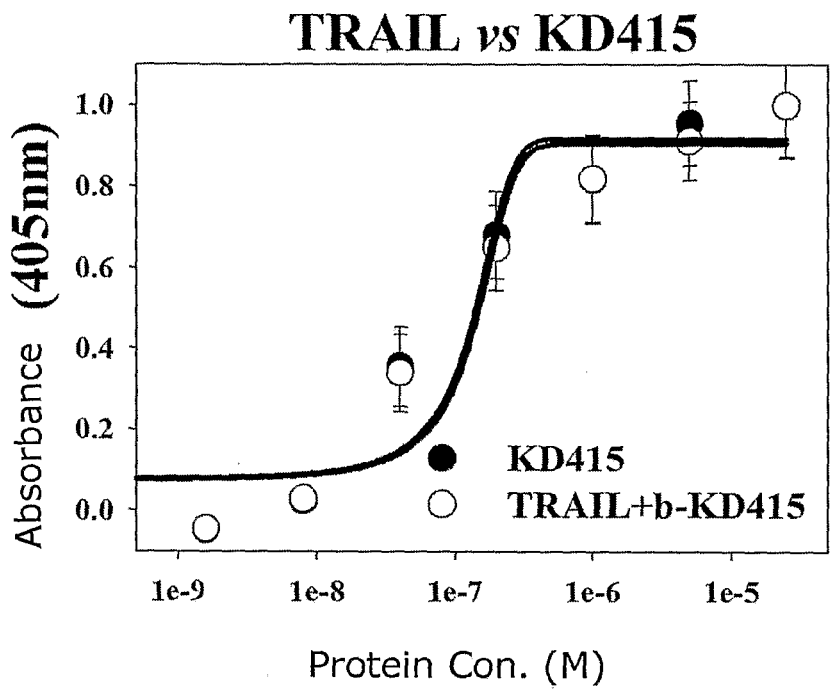
Figure 24:
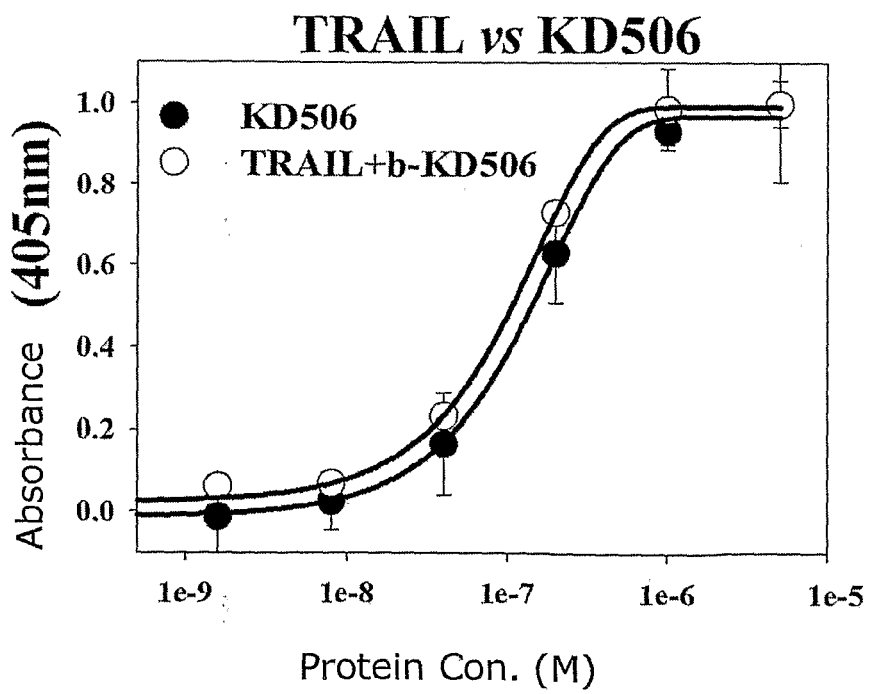
Figure 25:
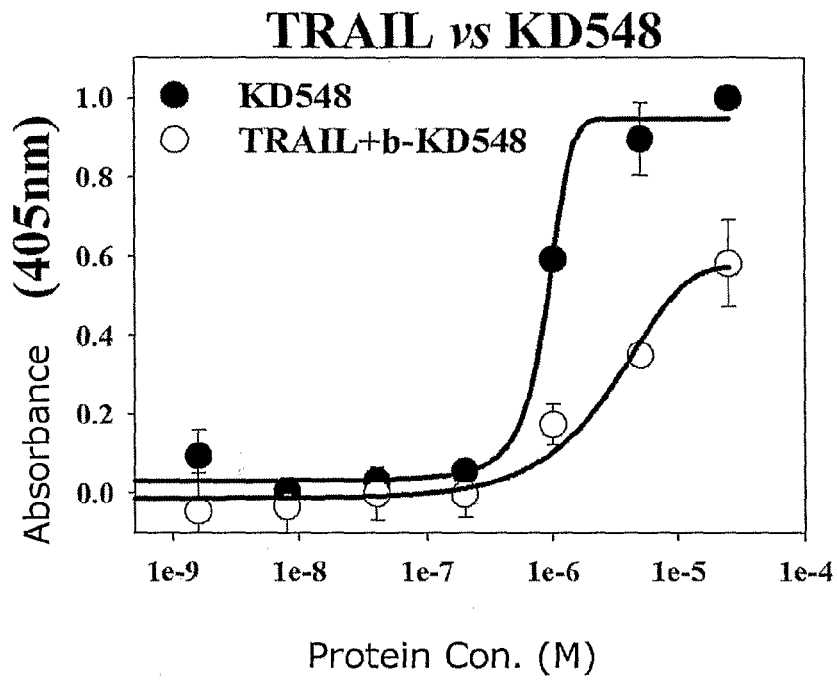
Figure 26:
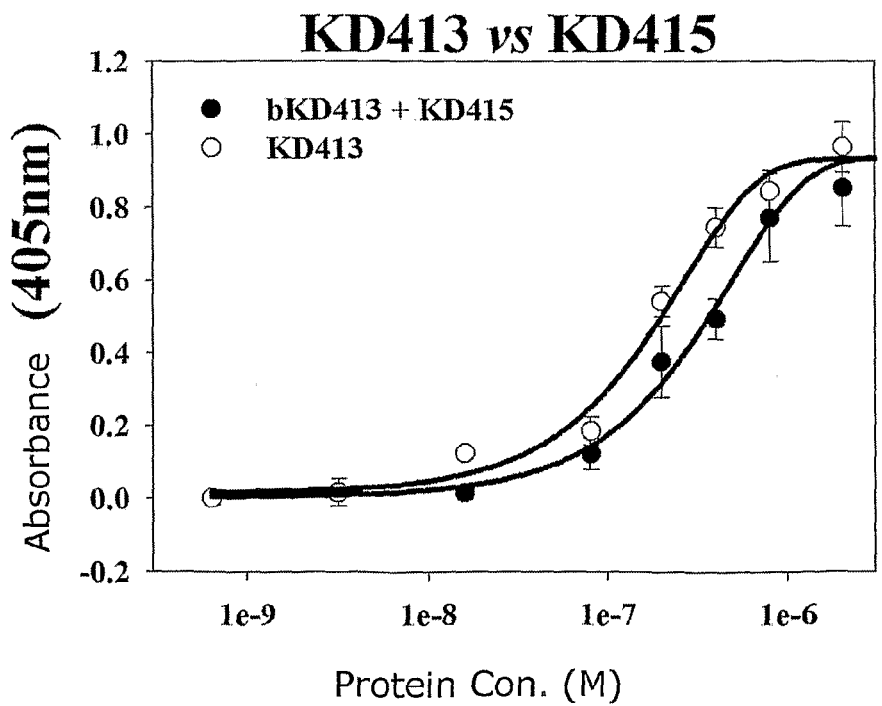
Figure 27:
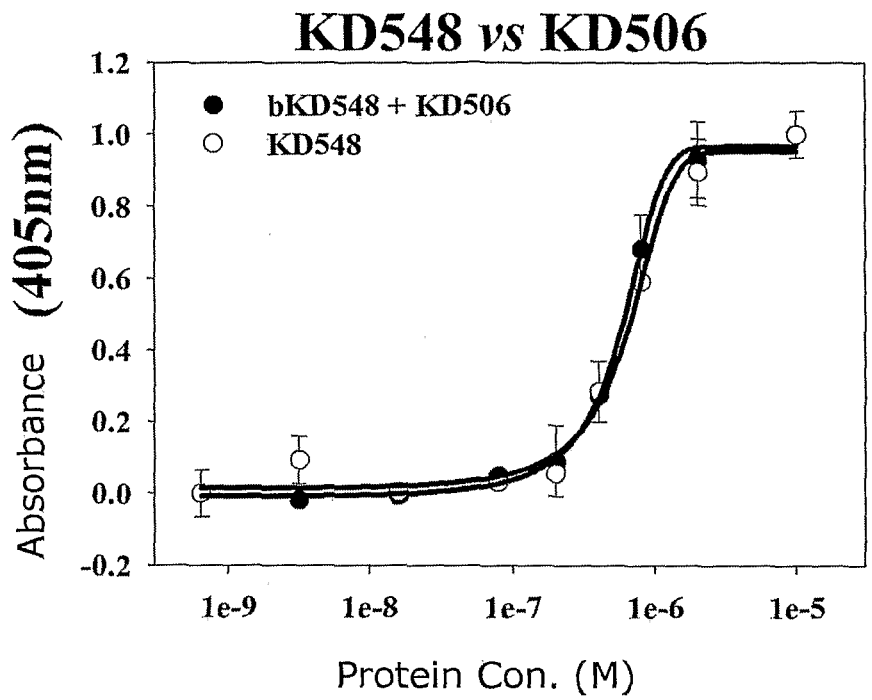

FIGS. 22-27 show the analysis of each binding site of Kringle domain variants screened to target molecules such as TRAIL in order to compare the binding sites of the anti-DR4 and -DR5 Kringle domain variants, by using competitive ELISA. FIGS. 22, 23, 24 and 25 show the results compared with binding sites of TRAIL, the anti-DR4, and -DR5 Kringle domain variants using competitive ELISA. FIG. 22 shows that the anti-DR4 Kringle domain variant KD413 has a different binding site from TRAIL. FIG. 23 shows that the anti-DR4 Kringle domain variant KD415 has a different binding site from TRAIL. FIG. 24 shows that the anti-DR5 Kringle domain variant KD506 has a different binding site from TRAIL. FIG. 25 shows that the anti-DR5 Kringle domain variant KD548 has a different binding site from TRAIL. FIG. 26 shows that the anti-DR4 Kringle domain variants KD413 and KD415 do not share a binding site to the same target molecule. FIG. 27 shows that the anti-DR5 Kringle domain variants KD506 and KD548 do not share a binding site to the same target molecule.

Example 9

Analysis of Secondary Structures of Anti-DR4, Anti-DR5 and Anti-TNFα Protein Scaffold Variants Based on the Kringle Domain Structure and Evaluation of their Thermodynamic Stabilities Far-UV CD spectra (190-260 nm) were used to analyze the secondary structures of the anti-DR4, -DR5 and -TNFα protein scaffold variants based on the Kringle domain structure with respect to the target molecules. Each of the anti-DR4, -DR5 and -TNFα protein scaffold variants based on the Kringle domain structure was put at a concentration of 100 μg/ml into a 0.1 cm-long quartz cuvette in PBS (pH 7.4), and measured at a distance of 0.5 nm in a wavelength range from 190 nm to 260 nm, by using a J-715 spectropolarimeter (Jasco Inc., Japan). PBS buffer (pH7.4) was used as the control to correct a graph, and the measurements were performed four times to obtain an average graph.

Figure 28:
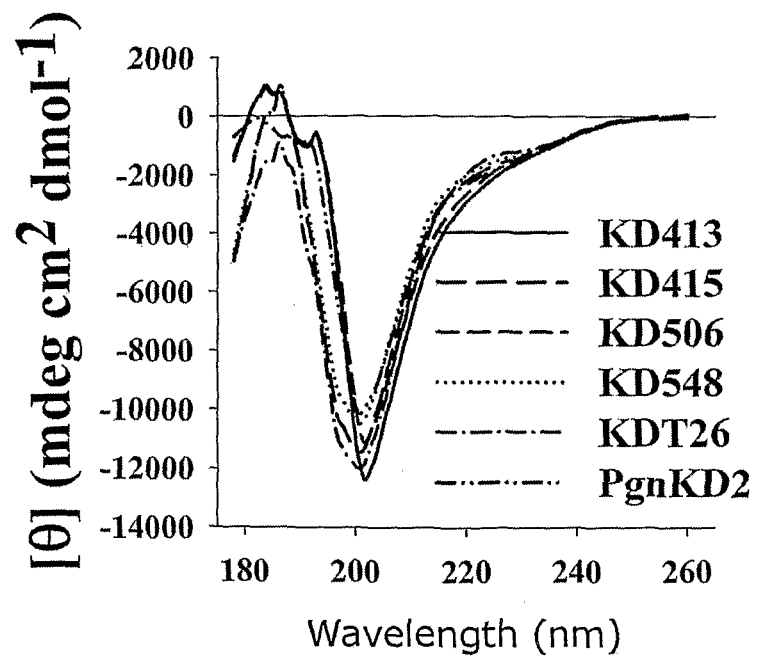
FIG. 28 shows the analytic results of the secondary structures of the wild-type plasminogen Kringle domain 2, the anti-DR4 Kringle domain variants, KD413 and KD415, the anti-DR5 Kringle domain variants, KD506 and KD548, and the anti-TNFα Kringle domain variant KDT26, by using circular dichroism (CD).

FIG. 28 shows the analytic results of the secondary structures of the wild-type plasminogen Kringle domain 2, the anti-DR4 Kringle domain variants KD413 and KD415, the anti-DR5 Kringle domain variants KD506 and KD548, and the anti-TNFα Kringle domain variant KDT26, by using circular dichroism (CD). The screened Kringle domain variants showed spectra similar to that of the wild-type plasminogen Kringle domain 2, and had a negative maximum peak at a wavelength range of 202 to 205 nm and a weak negative inflection point at 220 nm. These CD spectra revealed that the screened Kringle domain variants had a typical random structure and a weakly pleated structure. Also, the CD spectra revealed that, although many mutations were induced in wide loop regions of the Kringle domain variants, the Kringle domain variants maintained their secondary structures that are similar to that of the wild-type plasminogen Kringle domain 2.

Figure 29:
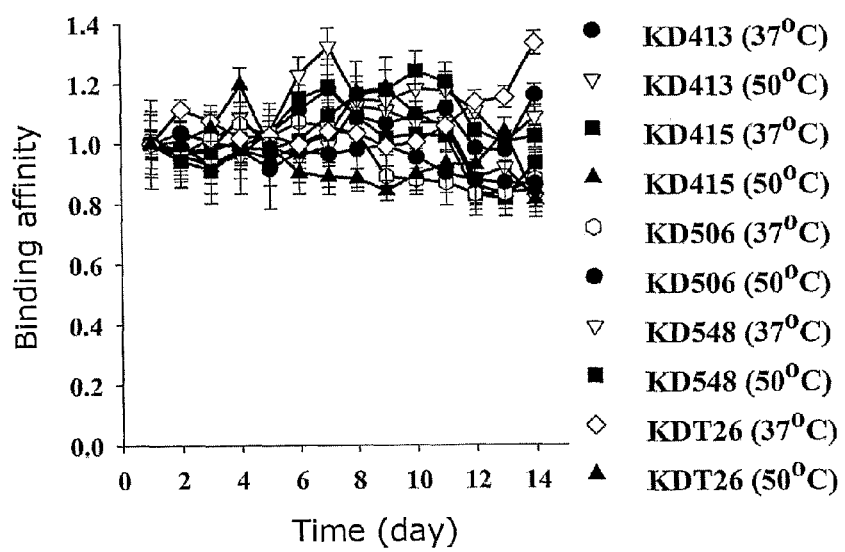
FIG. 29 shows the measurement results of binding activities of the anti-DR4, -DR5, and -TNFα protein scaffold variants based on the Kringle domain structure under a thermodynamic stress, by using ELISA.

ELISA and a differential scanning calorimeter (DSC) were used to evaluate the thermodynamic stability of the anti-DR4, -DR5 and -TNFα protein scaffold variants based on the Kringle domain structure with respect to target molecules. In order to evaluate the effect of thermodynamic stresses on the binding activity of the anti-DR4, -DR5 and -TNFα protein scaffold variants based on the Kringle domain structure to the target molecule, the thermodynamic stress was alternately applied to the anti-DR4, -DR5 and -TNFα protein scaffold variants based on the Kringle domain structure at 37° C. and 50° C. everyday for 14 days. The anti-DR4, -DR5 and -TNFα protein scaffold variants based on the Kringle domain structure undergoing the thermodynamic stress were measured for binding activity, using ELISA, in the same manner as described in Example 8. FIG. 29 shows the measurement results of binding activities of the anti-DR4, -DR5, and -TNFα protein scaffold variants based on the Kringle domain structure under a thermodynamic stress, using ELISA. As a result, it was revealed that the anti-DR4, -DR5 and -TNFα protein scaffold variants have a binding activity of 84% or more, compared to their original binding activities.

In order to confirm the fact that the anti-DR4, -DR5 and -TNFα protein scaffold variants based on the Kringle domain structure maintain their binding activities under the thermodynamic stress, the maximum heat-capacity temperatures ($T_m$) of the anti-DR4, -DR5 and -TNFα protein scaffold variants were analyzed using differential scanning calorimetry (DSC). The thermodynamic denaturation of the protein scaffold variants was measured at a rate of 1° C./min in a temperature range of 4° C. to 90° C. Measured values were corrected using the same compositions of a buffer, except the buffer does not comprise the Kringle domain variants. The maximum heat-capacity temperatures of the anti-DR4, -DR5 and -TNFα protein scaffold variants based on the Kringle domain structure were measured and converted as the functions of specific heat (the maximal heat capacity at constant pressure, $C_p$) temperature (Chang Y. et al., Biochemistry 36(25):7652-7663).

Figure 30:
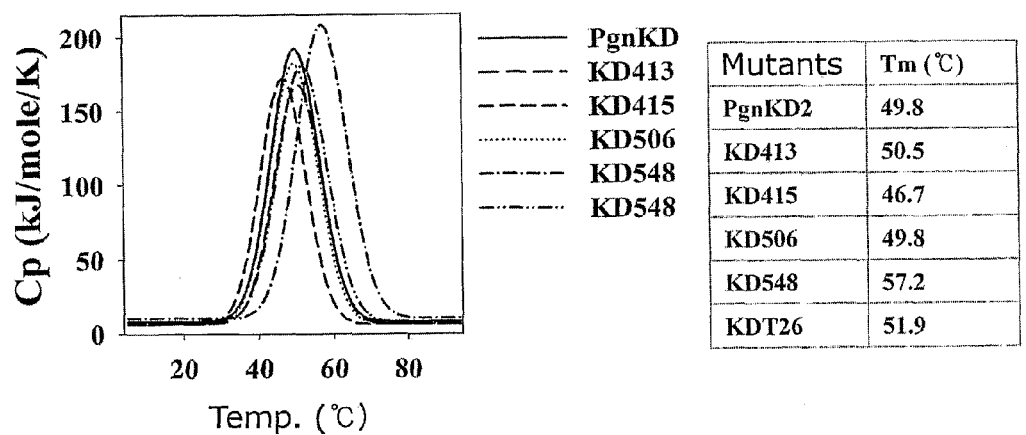
FIG. 30 shows the differential scanning calorimetric results and maximum heat-capacity temperatures of the wild-type plasminogen Kringle domain 2 and the anti-DR4, -DR5, and -TNFα protein scaffold variants based on the Kringle domain structure.

FIG. 30 shows the differential scanning calorimetric results of the wild-type plasminogen Kringle domain 2 and the anti-DR4, -DR5 and -TNFαprotein scaffold variants based on the Kringle domain structure, and their maximum heat-capacity temperatures. The maximum heat-capacity temperatures of the wild-type plasminogen Kringle domain 2, the anti-DR4 Kringle domain variant KD413, KD415, the anti-DR5 Kringle domain variant KD506, KD548 and the anti-TNFα Kringle domain variant KDT26 were as follows: wild-type plasminogen Kringle domain 2(49.8° C.), the anti-DR4 Kringle domain variant KD413(50.5° C.), KD415(46.7° C.), the anti-DR5 Kringle domain variant KD506(49.8° C.), KD548(57.2° C.) and the anti-TNFα Kringle domain variant KDT26(51.9° C.) respectively. FIG. 30 shows that, although many mutations were induced in the wide range of loop regions of the Kringle domain variants, the Kringle domain variants had thermodynamic stabilities that are similar to that of the wild-type plasminogen Kringle domain 2.

Example 10

Expression and Purification of Fc-Fused Anti-DR4, -DR5 and -TNFα Kringle Domains Among the protein scaffold variants based on the Kringle domain structure as described in Example 7, an Fc domain region from a hinge of human immunoglobulin G1 was cloned in frame into a yeast *Pichia pastoris* expression vector (pPICZaA, Invitrogen, USA) including the anti-DR4 variants (KD413 and KD415), the anti-DR5 variant (KD506 and KD548) and the anti-TNFα α variant (KDT26), by using the restriction enzymes AflII/XbaI.

The expression was performed in the same manner as described in Example 7. The target protein was purified from a supernatant, and a protein A-Sepharose FF column (rProtein A-Sepharose FF column, GE Healthcare, USA) that specifically effectively purifies an Fc protein was used.

Figure 31:
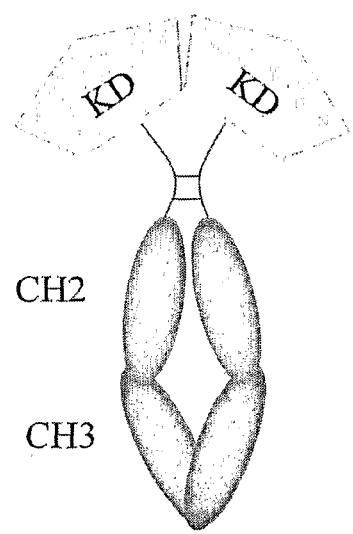
FIGS. 31-34 are schematic diagrams showing a fused structure of a Kringle domain variant and Fc domain of human antibody IgG1, and show the SDS-PAGE and HPLC results indicating that the fused structure is present in the form of dimers.
Figure 32:
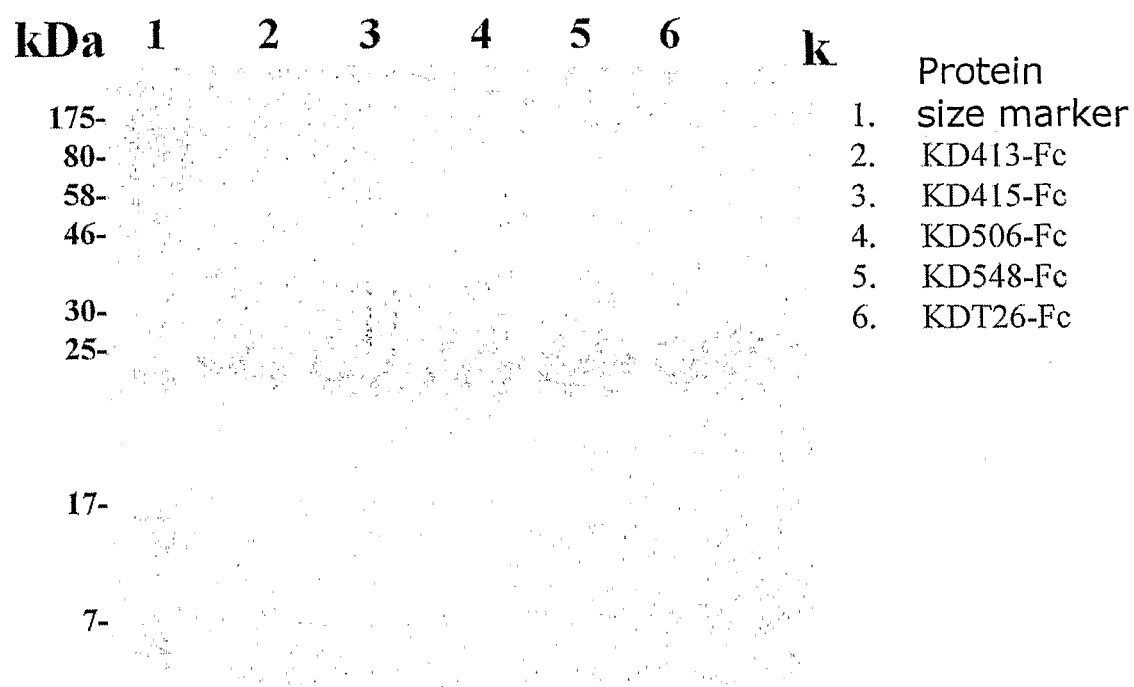
Figure 33:
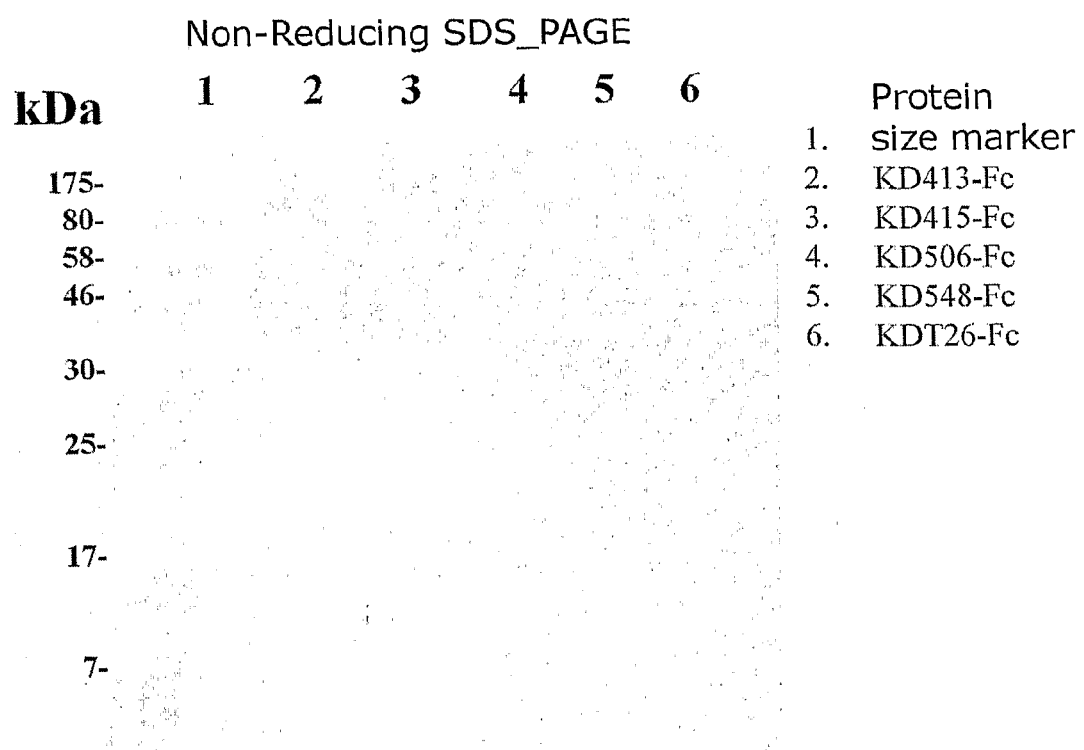

FIGS. 31-34 are a schematic diagram showing the fusion of a Kringle domain variant and Fc domain of human antibody IgG1, and show the SDS-PAGE and HPLC results indicating that the fusion structure is present in the form of dimers. FIG. 31 is a schematic diagram showing the Fc-fused Kringle domain variant, and shows that the Fc-fused Kringle domain variant acts as bivalent. FIGS. 32 and 33 show the analytic results of the anti-DR4, -DR5 and -TNFα Fc-fused Kringle variants using 15% SDS-PAGE at a reducing (FIG. 32) or a non-reducing (FIG. 33) condition after their purification. The Fc-fused Kringle domains were purified with a purity of 98% or more. All the purified Kringle domains showed a molecular weight of approximately 38 kDa on the reducing SDS-PAGE and a molecular weight of approximately 76 kDa on the non-reducing SDS-PAGE. This indicates that the expressed and purified Fc-fused Kringle domains are present in the form of dimers in a liquid phase, and the dimers are easy to be formed by the disulfide bonds in hinge regions. The concentration and amount of the Fc-fused Kringle domains are quantified using Bradford and BCA methods.

Figure 34:
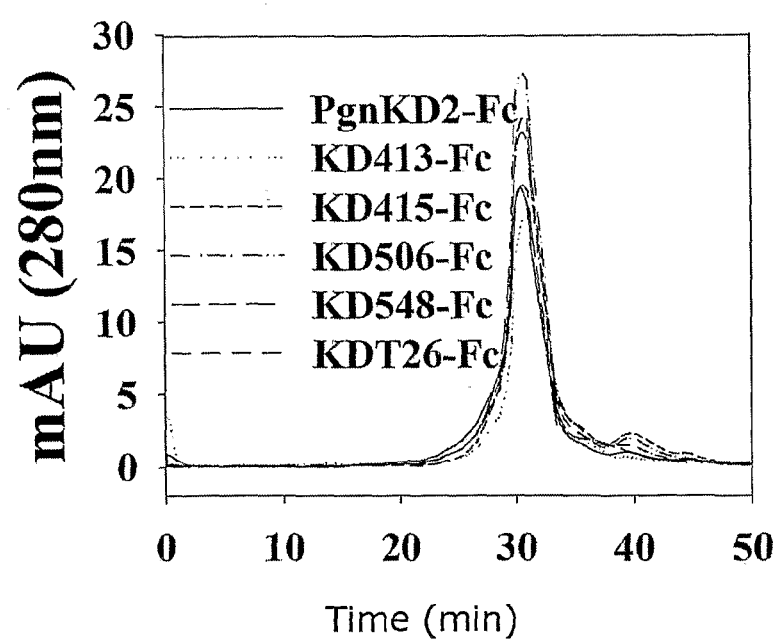
Figure 35:
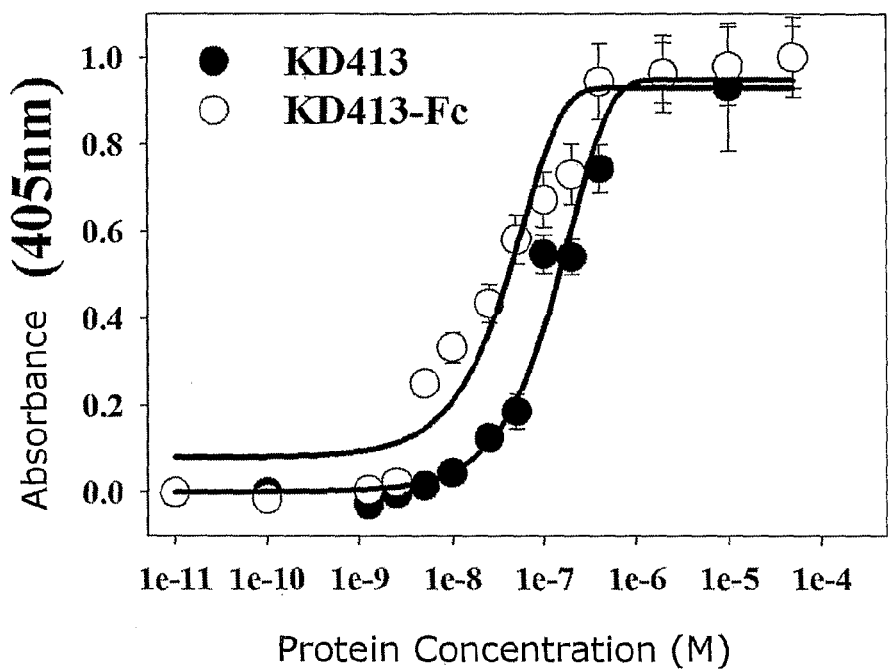
FIGS. 35-39 show the measurement results of binding affinities of the anti-DR4, -DR5 and -TNFα Kringle domain variants and the Fc-fused anti-DR4, -DR5 and -TNFα Kringle domain variants, by using affinity ELISA.
Figure 36:
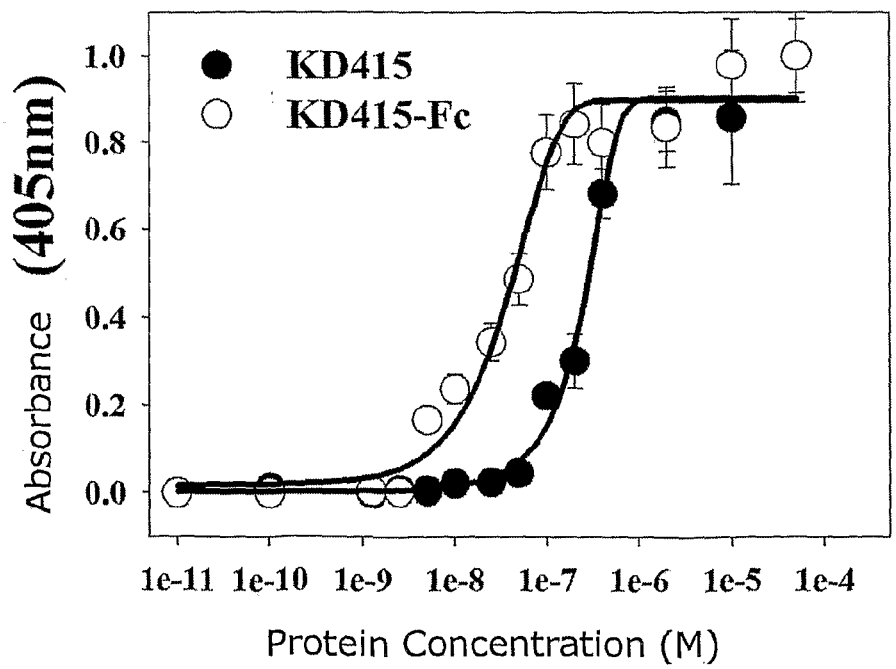
Figure 37:
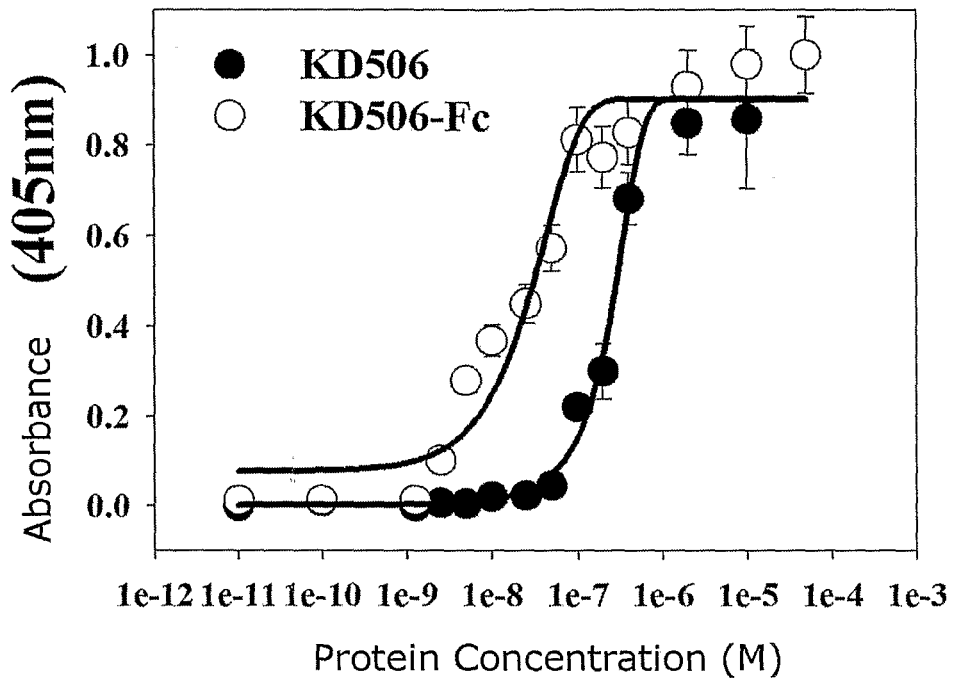
Figure 38:
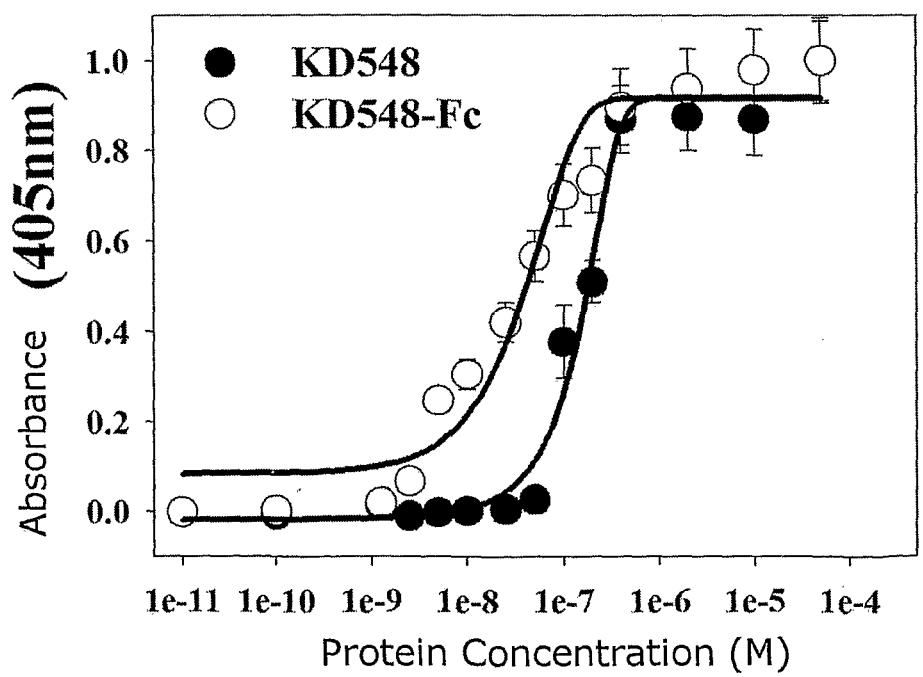
Figure 39:
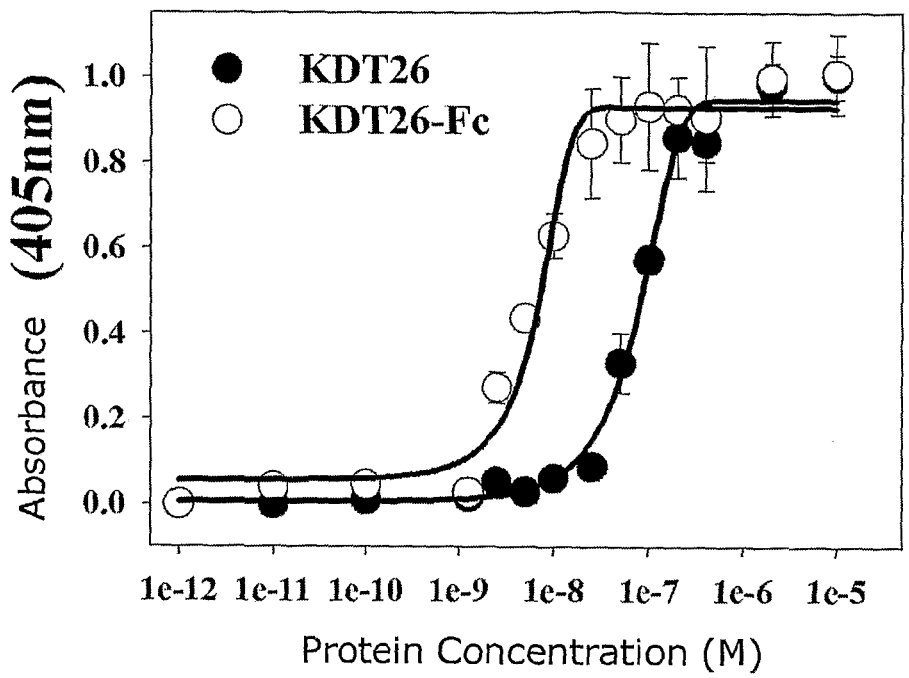
Figure 40:
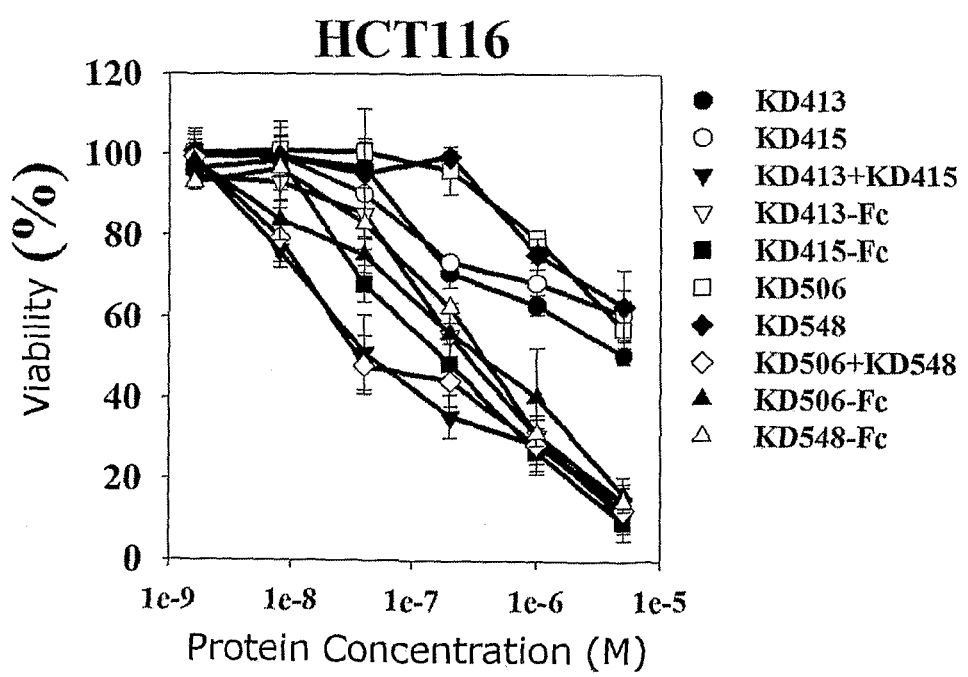
FIGS. 40-46 show the analytic results, using MTT assay, indicating that the cell death is induced in a concentration-dependent manner in cell lines HCT116 (FIG. 40), H460 (FIG. 41), U87MG (FIG. 42), HepG2 (FIG. 43), Jurkat (FIG. 44), and HL60 (FIG. 45) by the anti-DR4 KD413, KD415, KD413-Fc and KD415-Fc Kringle domain variants (0.001~5 μM), and the anti-DR5 KR506, KD548, KD506-Fc and KD548-Fc Kringle domain variants (0.001~5 μM), all of which have biological activities, among the anti-DR4 and -DR5 protein scaffold variants based on the Kringle domain structure, after the 60-hour incubation of the Fc Kringle domain variants. As the control, the wild-type plasminogen Kringle domain 2 and TRAIL are used (FIG. 46).
Figure 41:
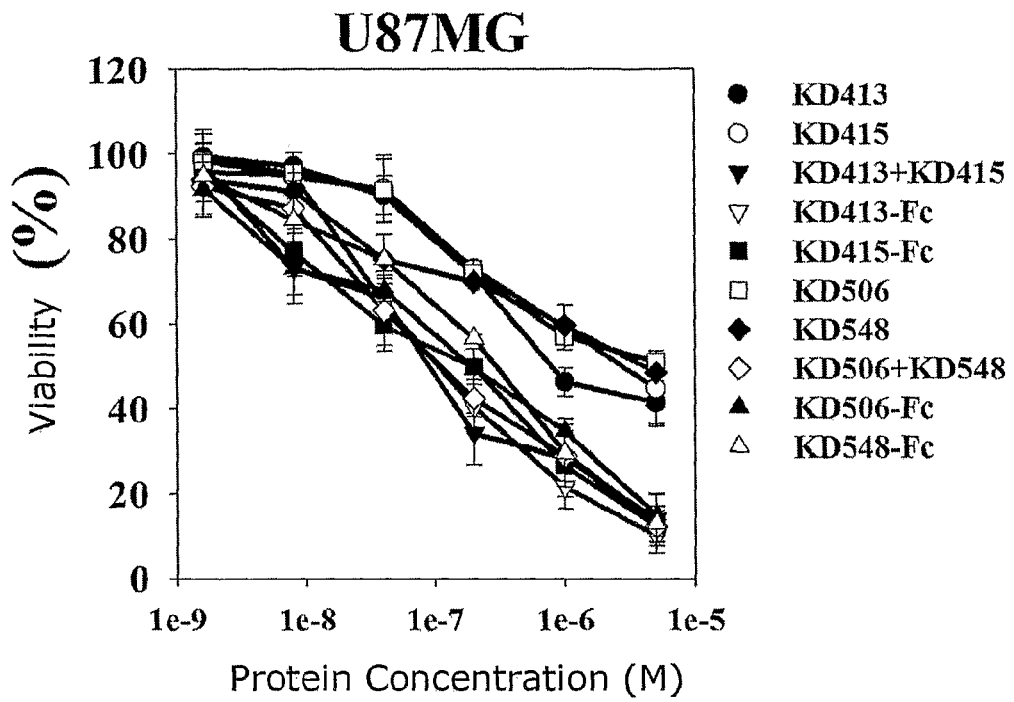
Figure 42:
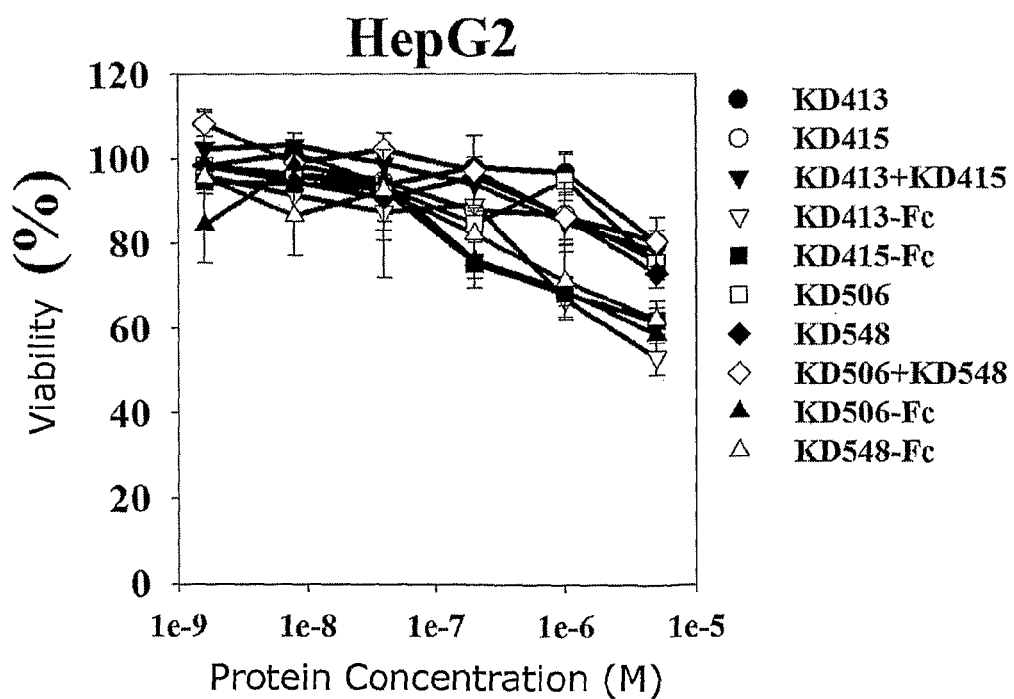
Figure 43:
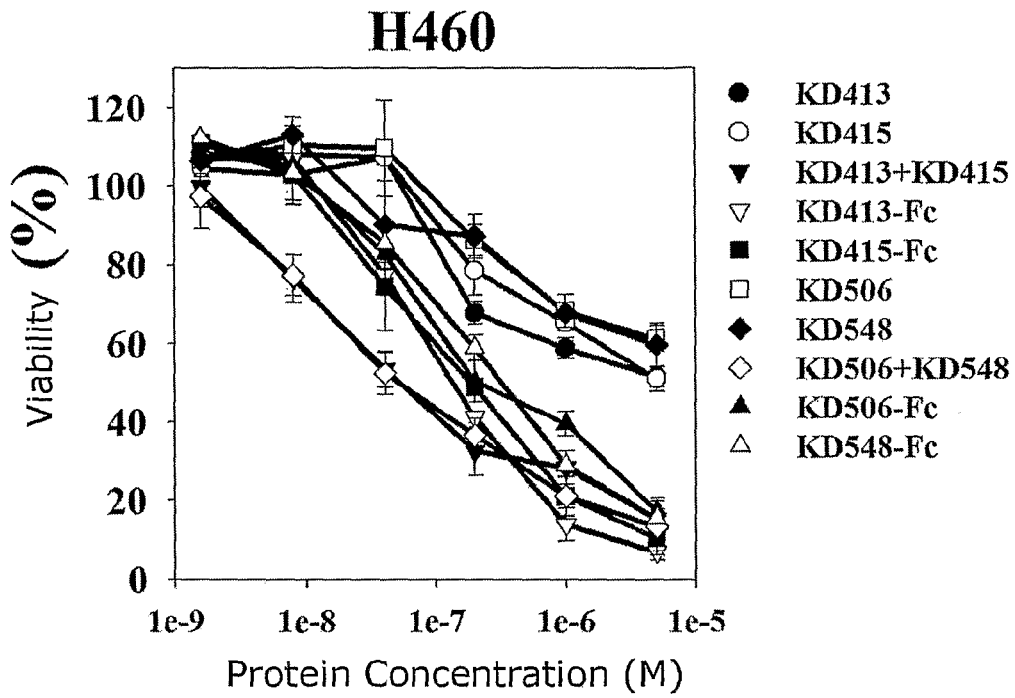
Figure 44:
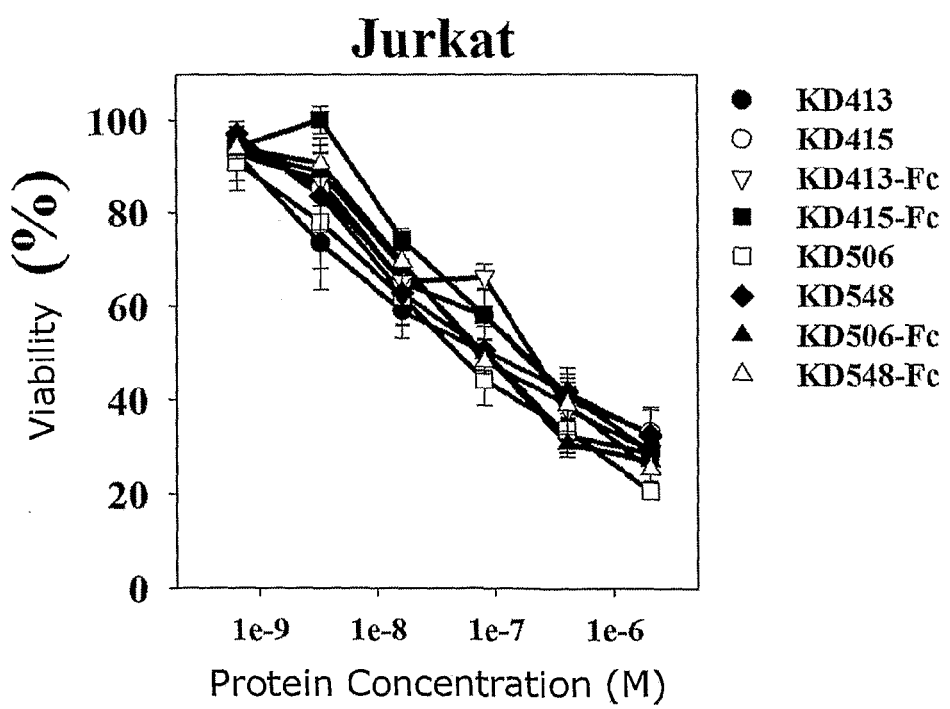
Figure 45:
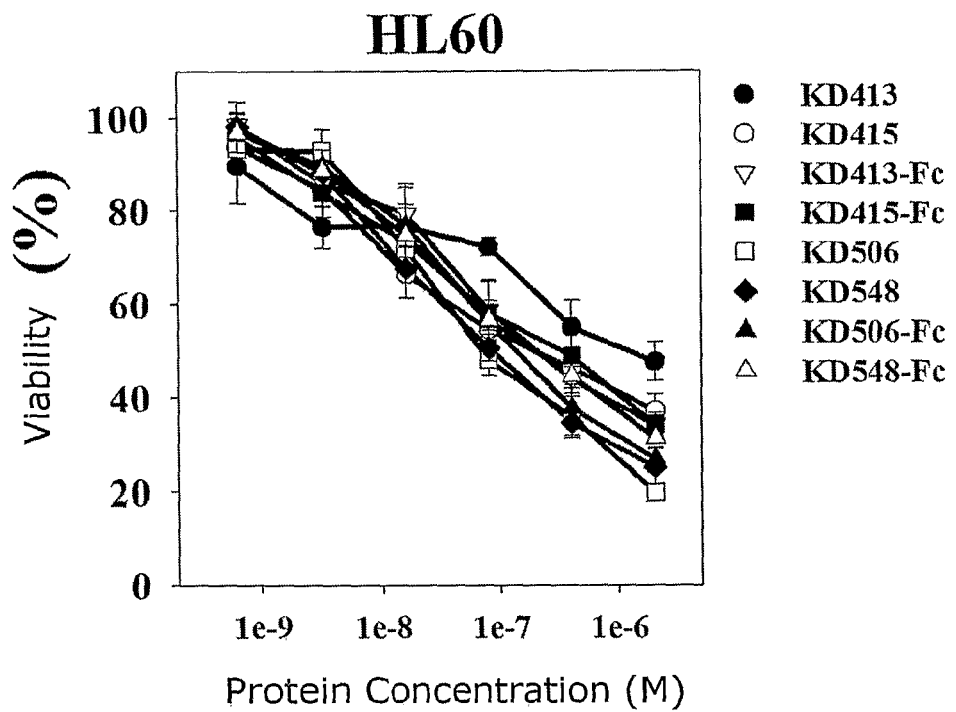

FIG. 34 shows the experimental results on the anti-DR4, -DR5 and -TNFα a Fc-fused Kringle domains using a size exclusion chromatography column (Superdex™200 10/300GC, GE Healthcare, Sweden) in order to confirm whether the anti-DR4, -DR5 and -TNFα Fc-fused Kringle domains are present in the form of dimers by using high performance liquid chromatography (HPLC, the Agilent 1200 Series LC Systems and Modules, Agilent, USA). Here, the experimental conditions were identical to those described in Example 7. As protein size markers, alcohol dehydrogenase (150 kDa), ovalbumin (45 kDa), chymotrypsinogen (25 kDa) and ribonuclease A (13.7 kDa) were used. One heights was measured in all of the clones of the Fc-fused Kringle variants, which indicates that the Fc-fused anti-DR4, -DR5 and -TNFα Kringle domains are present in the form of dimers.

Example 11

Analysis of Affinity of Fc-Fused Anti-DR4, -DR5 and -TNFα Kringle Domains

In order to analyze the affinities of the Fc-fused anti-DR4, -DR5 and -TNFα Kringle domains to target molecules, the affinities of the Fc-fused anti-DR4, -DR5 and -TNFα Kringle domains to the target molecules were analyzed using ELISA, as described in Example 8.

FIGS. 35-39 show the measurement results of binding affinities of the anti-DR4, -DR5 and -TNFα Kringle domain variants and the Fc-fused anti-DR4, -DR5 and -TNFα Kringle domain variants, by using affinity ELISA. From the ELISA results of FIGS. 35-39, the measured affinities of the Fc-fused anti-DR4, -DR5 and -TNFα Kringle domains were 60±8 nM in the case of the KD413-Fc, 53±6 nM in the case of the KD415-Fc, 43±6 nM in the case of the KD 506-Fc, 58±5 nM in the case of the KD548-Fc, and 3.8±0.4 nM in the case of the KDT26-Fc.

Example 12

Identification of In Vitro Biological Activities of Anti-DR4 and -DR5 Protein Scaffold Variants Based on the Kringle Domain Structure In order to evaluate the cell death of the purified anti-DR4, -DR5 Kringle domain variants, among the cancer cell lines, TRAIL-sensitive cell lines HCT116 (human colorectal carcinoma cell line (i.e. colorectal cancer cell), American Type Culture Collection (ATCC) CCL-247), H460 (Human NSCLC cell lines (i.e. lung cancer cell), American Type Culture Collection (ATCC HTB-177)), Jurkat (human acute T cell leukemia cell line (i.e. blood cancer cell), ATCC TIB-152) and HL60 (human acute promyelocytic leukemia cell line (i.e. blood cancer cell), ATCC CCL-240), and TRAIL-resistant cell lines U87MG (human glioblastoma cell line (i.e. brain cancer cell), ATCC HTB-14) and HepG2 (human carcinoma hepatocell line (i.e. liver cancer cell), ATCC HB-8065) were used as the model cell lines. The anti-DR4 and -DR5 Kringle domain variants (0.001-5 µM) were treated with the model cell lines, and their cell death was evaluated using an MTT assay (Park K J. et al., Cancer Research, 67:7327-7334, 2007, Orogen N. et al., Cancer Research, 60(22):6259-6265, 2000).

In order to separate adhesive cell lines HCT116, H460, U87MG and HepG2 from their culture vessels (T-flask), the adhesive cell lines treated with 1 ml of a TE (trypsin-EDTA) buffer, and a TE reaction was then stopped using 5 ml of Dulbecco's modified eagle medium (DMEM, GIBCO Invitrogen Co., USA) supplemented with 10% fatal bovine serum albumin (FBS, GIBCO Invitrogen Co., USA). Then, each of the cultured adhesive cell lines was centrifuged at a rotary speed of 1000 rpm for 5 minutes. The harvested adhesive cell lines were re-suspended with DMEM (GIBCO Invitrogen co., USA) supplemented with 10% fatal bovine serum albumin (FBS, GIBCO Invitrogen Co., USA), divided into a 96-well plate at $1 \times 10^4$ cells per well, incubated for 24 hours in a 5% $CO_2$ incubator at 37° C., and then used for the MTT analysis. Enriched cell lines Jurkat and HL60 were re-suspended with RPMI1640 (Dulbecco's Modified Eagle Medium (Welgene, USA)) supplemented with 10% fatal bovine serum albumin (FBS, GIBCO Invitrogen Co., USA), divided into a 96-well plate at $1 \times 10^4$ cells per well, incubated for 24 hours in a 5% $CO_2$ incubator at 37° C., and then used for the MTT analysis.

Figure 46:
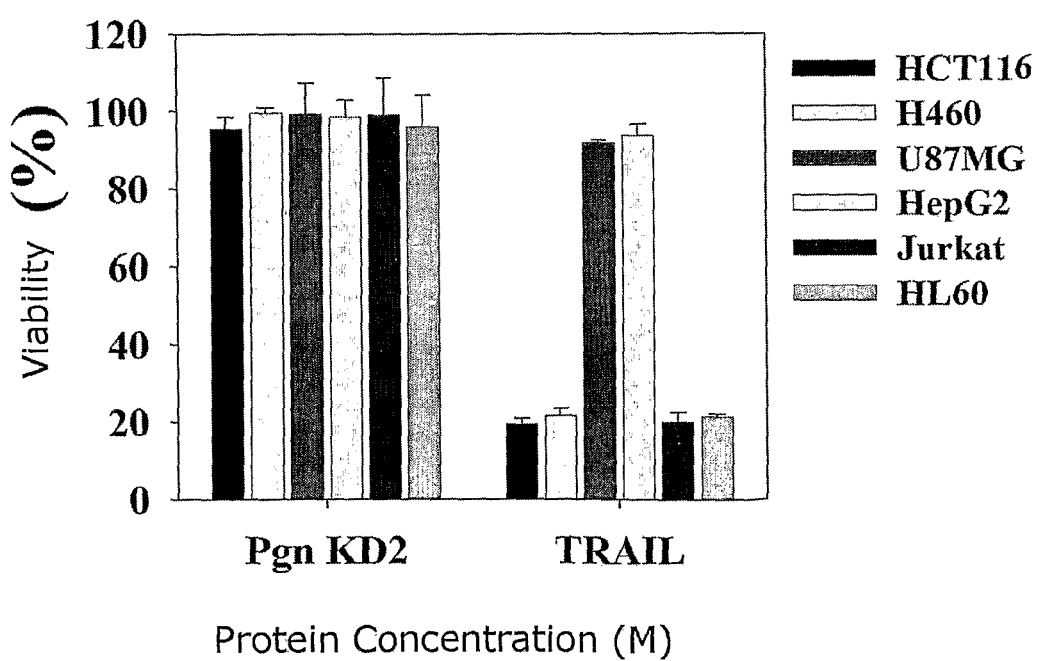

FIGS. 40-46 show the analytic results, using MTT assay, indicating that the cell death is induced in a concentration-dependent manner in cell lines HCT116 (FIG. 40), H460 (FIG. 41), U87MG (FIG. 42), HepG2 (FIG. 43), Jurkat (FIG. 44), and HL60 (FIG. 45) by the anti-DR4 KD413, KD415, KD413-Fc and KD415-Fc Kringle domain variants (0.001~5 µM), and the anti-DR5 KR506, KD548, KD506-Fc and KD548-Fc Kringle domain variants (0.001~5 µM), which have biological activities among the anti-DR4 and -DR5 protein scaffold variants based on the Kringle domain structure, after the 60-hour incubation of the Fc Kringle domain variants. When the wild-type plasminogen Kringle domain 2 (PgnKD2)-treated control was incubated for the same time, the cell death was not observed in the control (FIG. 46). When the TRAIL-treated control was incubated for the same time, the cell death was observed only in the TRAIL-sensitive cell lines HCT116, H460, Jurkat and HL60 (FIG. 46). EC50 (a concentration of protein causing a 50% cell death) of each cell line was measured, as follows. Here, the cell lines were presented in order of HCT116, H460, U87MG; Jurkat and HL60. KD413 had EC50 values of 5.3±0.2 5.9±0.5 µM, 0.9±0.2 µM, 0.09±0.03 µM, and 1.4±0.2 µM, KD415 had EC50 values of 11.0±0.9 µM, 5.3±0.4 µM, 4.9±0.6 µM, 0.2±0.1 µM, and 0.13±0.02 µM, KD413-Fc had EC50 values of 0.38±0.08 µM, 0.22±0.06 µM, 0.14±0.04 µM, 0.06±0.01 µM, and 0.02±0.01 µM, KD415-Fc had EC50 values of 0.18±0.04 µM, 0.20±0.08 µM, 0.20±0.05 µM, 0.08±0.01 µM, and 0.06±0.01 µM, KD506 had EC50 values of 6.3.±0.5 µM, 10.4±1.4 µM, 5.8±0.6 µM, 0.2±0.1 µM, and 0.21±0.01 µM, KD548 had EC50 values of 9.3±0.8 µM, 9.9±0.7 µM, 4.6±0.4 µM, 0.3±0.1 µM, and 0.26±0.02 µM, KD506-Fc had EC50 values of 0.08±0.03 µM, 0.23±0.05 µM, 0.20±0.06 µM, 0.08±0.01 µM, and 0.23±0.04 µM, and KD548-Fc had EC50 values of 0.52±0.06 µM, 0.45±0.04 µM, 0.40±0.06 µM, 0.07±0.01 µM, and 0.22±0.04 µM. These results indicate that the specifically screened Kringle domain variants may specifically bind to the target molecules to show their biological activities. Since the Kringle domain variants had different binding sites against antigens as described above in Example 8, the Kringle domain variants having different binding sites might also have synergic effects when they were treated together. As shown in FIGS. 40-46, it was revealed that when the anti-DR4 Kringle domain variants KD413 and KD415 were treated together, they have an EC50 value that is 10~100 times higher due to the synergic effects. EC50 values in the 3 cell lines HCT116, H460 and U87MG were 0.053±0.005 µM, 0.066±0.004 µM, and 0.121±0.008 µM. When the anti-DR5 Kringle domain variants KD506 and KD548 were treated together, they have an EC50 value that is 10~100 times higher due to the synergic effects. EC50 values in the 3 cell lines HCT116, H460 and U87MG were 0.021±0.002 µM, 0.064±0.005 µM, and 0.142±0.012 µM.

Figure 47:
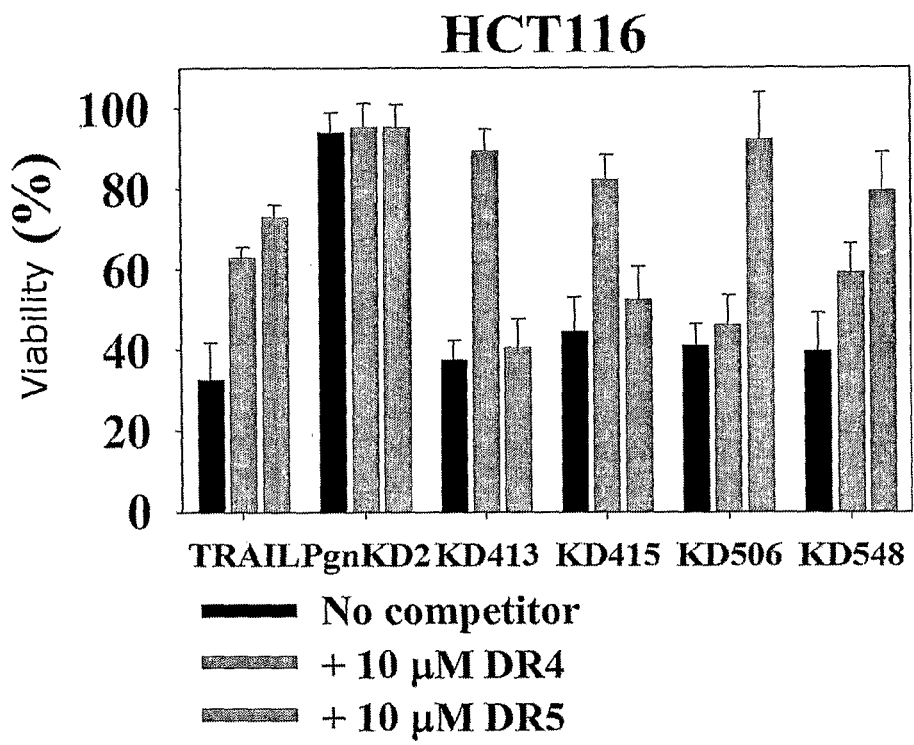
FIGS. 47-48 show the results, using MTT assay, indicating that the cell death by the anti-DR4 and -DR5 protein scaffold variants based on the Kringle domain structure is inhibited by the purified DR4 and DR5.
Figure 48:
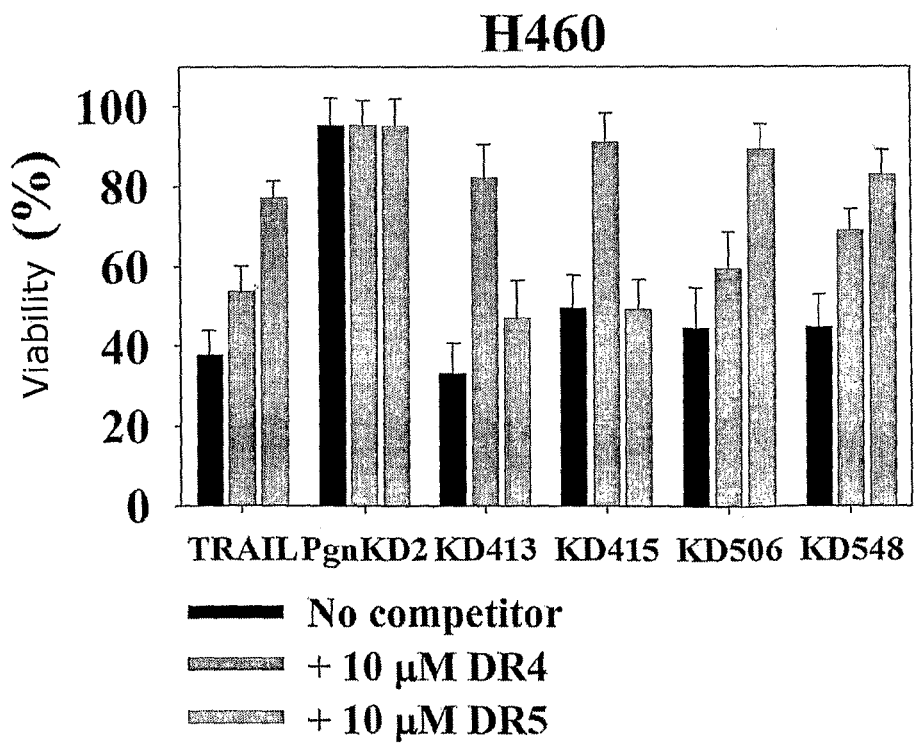

FIGS. 47 and 48 show the evaluation results, using MTT assay, indicating that the cell death by the anti-DR4 and -DR5 protein scaffold variants based on the Kringle domain structure is inhibited by purified DR4 and DR5. This indicates that the cell death by the anti-DR4 and -DR5 protein scaffold variants based on the Kringle domain structure was induced by DR4 and DR5 on cell surfaces. 1 µM of the anti-DR4 and -DR5 Kringle domain variants, KD413, KD415, KD506 and KD548, were reacted for 1 hour with DR4 and DR5, both of which were purified from 10 µM *E. coli*. Then, the above-mentioned HCT116 and H460 cell lines were treated with each of the anti-DR4 and -DR5 Kringle domain variants, and analyzed 40 hours after the treatment using an MTT assay. The wild-type plasminogen Kringle domain 2 and TRAIL were used as the controls. The wild-type plasminogen Kringle domain 2 did not induce the cell death regardless of the DR4 and DR5, and the TRAIL partially inhibited the cell death at the presence of the DR4 and DR5. The cell death by the anti-DR4 Kringle domain variants KD413 and KD415 was inhibited only by the DR4. The cell death by the anti-DR5 Kringle domain variant KD506 was inhibited only by the DR5. However, since the anti-DR5 Kringle domain variant KD548 has a binding activity to both of the DR4 and DR5 (FIG. 20), its cell death was partially inhibited by both of the DR4 and DR5 when the DR4 and DR5 are present like TRAIL.

Figure 49:
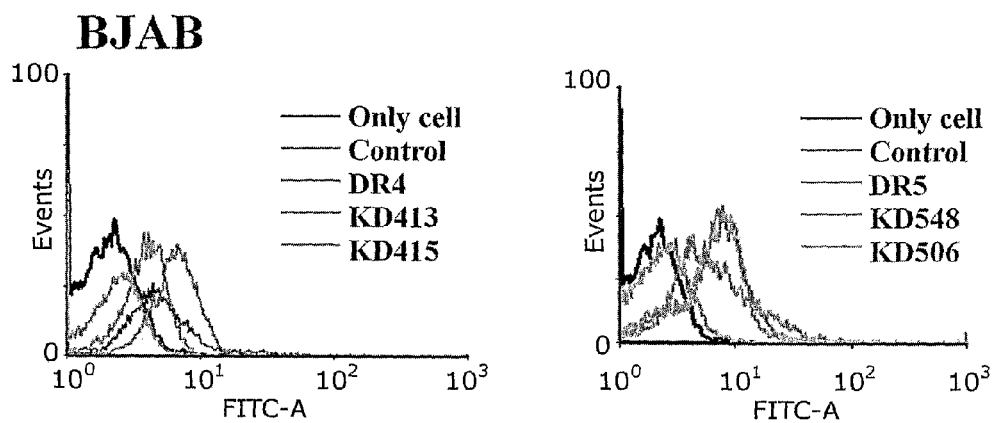
FIGS. 49-54 show the results obtained by measuring binding levels of the anti-DR4 and -DR5 Kringle domain variants KD413, KD415, KD506 and KD548 with cell surface DR4 and DR5 in a cell line BJAB (Human B lymphocyte, B cell lymphoma), a BJAB DR5−/− cell line in which the DR5 is completely inactivated, an H460 cell line, and an H460 cell line which the DR4 is over-expressed, by using FACS in the method described in Example 6.
Figure 50:
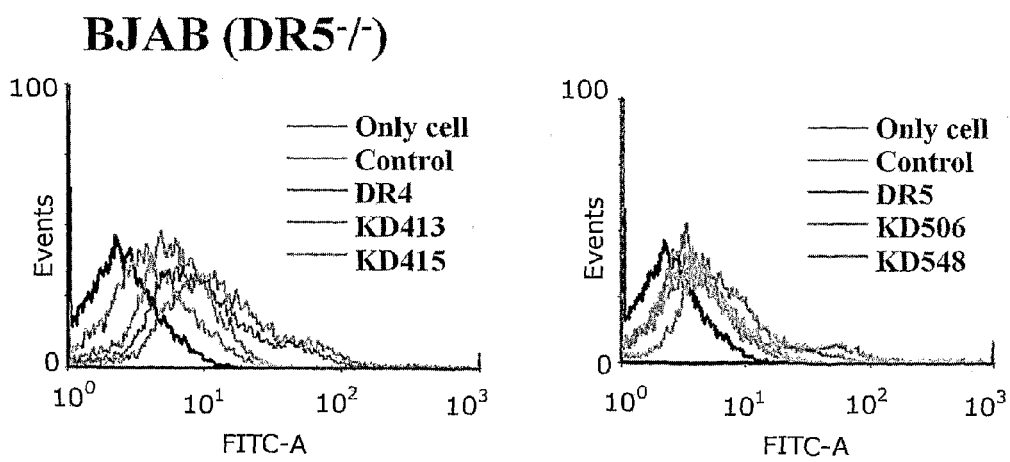
Figure 51:
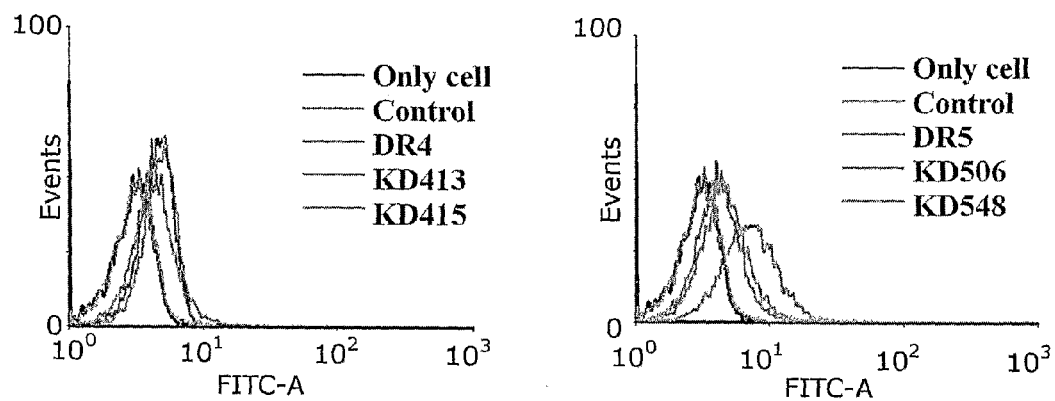
Figure 52:
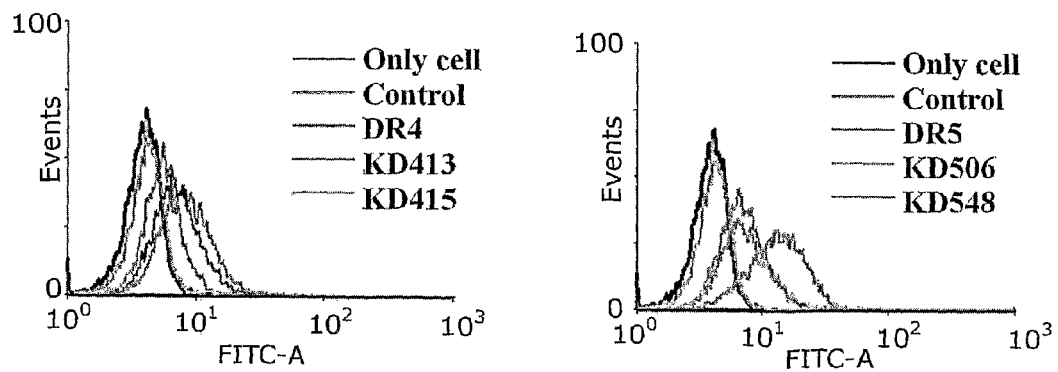
Figure 53:
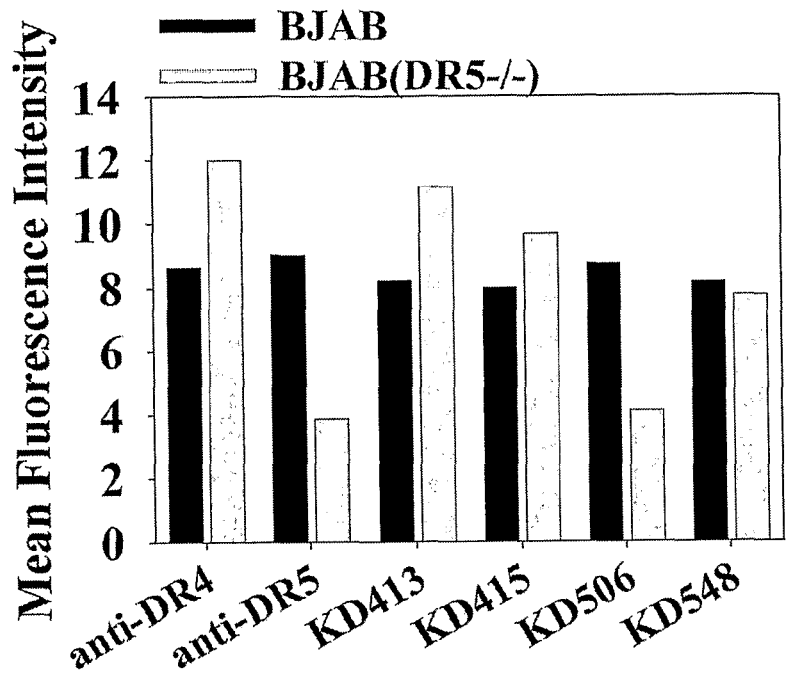
Figure 54:
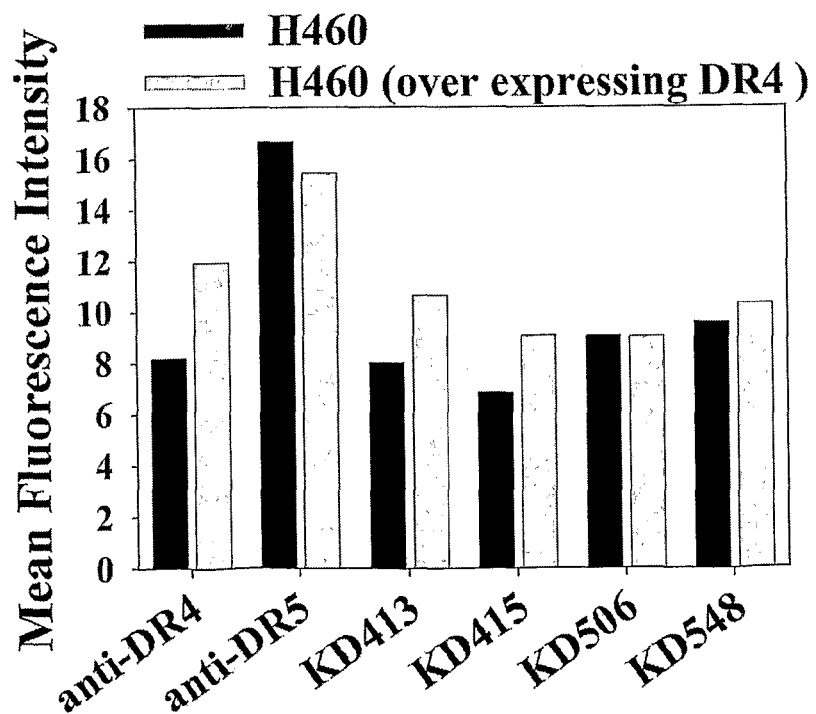

FIGS. 49-54 show the results obtained by measuring binding levels of the anti-DR4 and -DR5 Kringle domain variants, KD413, KD415, KD506 and KD548, to cell surface of DR4 and DR5 in an enriched cell line BJAB (Human B lymphocyte, B cell lymphoma), a BJAB DR5−/− cell line in which DR5 is completely inactivated, an H460 cell line, and an H460 cell line over-expressing DR4, using FACS in the method described in Example 6. FIGS. 49 and 50 show that when DR5 is completely inactivated, the anti-DR4 Kringle domain variants, KD413 and KD415, maintain the binding level in respect to cell surfaces, but the anti-DR5 Kringle domain variants, KD506 and KD548, specifically bind to the cell surface DR5 since they have a decreased binding level in respect to cell surface. FIGS. 51 and 52 show that when the DR4 is over-expressed, the anti-DR4 Kringle domain variants KD413 and KD415 have an increased binding level in respect to cell surfaces, but the anti-DR4 Kringle domain variants KD413 and KD415 specifically bind to the cell surface DR4 since the anti-DR5 Kringle domain variants KD506 and KD548 retain a constant binding level in respect to cell surfaces. FIG. 53 shows a graph plotting the data shown in FIGS. 49 and 50, and FIG. 54 shows a graph plotting the data shown in FIGS. 51 and 52.

Example 13

Analysis of Cell Death Mechanism of Anti-DR4 and -DR5 Protein Scaffold Variants Based on the Kringle Domain Structure In order to analyze whether the cell death of the anti-DR4 and -DR5 protein scaffold variants based on the Kringle domain structure is an apoptosis mechanism, the enriched cell lines Jurkat and HL60 were treated with the anti-DR4 and DR5 Kringle domains for 35 hours, as described in Example 11, and stained with annexin V-FITC and propidium iodide (PI), respectively, and then measured using FACS as described in Example 6. Also, the enriched cell lines were treated with 0.5 μg/ml of (~30 nM) TRAIL as the control for 4 hours, and then analyzed using FACS.

Figure 55:
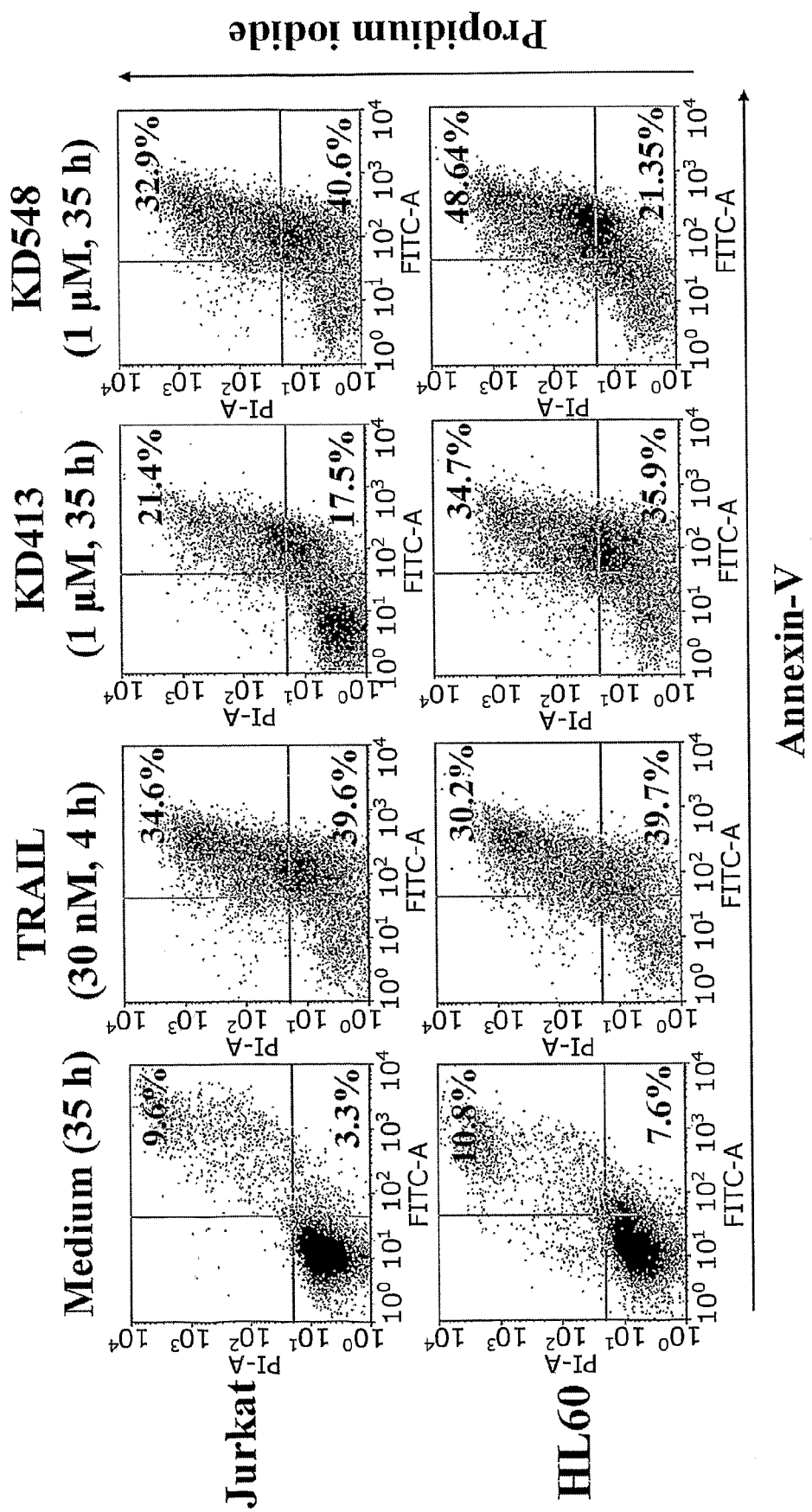
FIG. 55 shows the results obtained by staining Jurkat and HL60 cell lines with annexin V-FITC and PI dye and analyzing the Jurkat and HL60 cell using FACS.

FIG. 55 shows the results obtained by staining Jurkat and HL60 cell lines with annexin V-FITC and PI dye and analyzing the Jurkat and HL60 cell using FACS. When treated with the TRAIL as the control, which is characteristic of the initial apoptosis, the annexin V-FITC+/PI− cells were distributed at a rate of 39.6%, in the Jurkat cell line and distributed at a rate of 39.7% in the HL60 cell line, and the anti-DR4 Kringle domain variant KD413 was distributed at a rate of 17.5% in the Jurkat cell line and distributed at a rate of 35.9% in the HL60 cell line. Also, the anti-DR5 Kringle domain variant KD548 was distributed at a rate of 40.6% in the Jurkat cell line and distributed at a rate of 21.35% in the HL60 cell line, which indicates that the apoptosis is a cell death mechanism.

Example 14

In Vivo Biological Identification Anti-DR4 and -DR5 Protein Scaffold Variants Based on the Kringle Domain Structure For the purpose of in vivo biological identification of the anti-DR4 and -DR5 Kringle domain variant, each of HCT116 and U87MG cell lines was injected at a concentration of $5 \times 10^6$ cells per mouse into right legs of the 4-weeks-old female BALB/c athymic nude mice (CAnN.Cg-Foxn1nu/Crl, 15-20 g, Orientbio Inc. (Korea)), respectively. After approximately 7 days, 7 mice were treated with the anti-DR4 and -DR5 Kringle domain variants KD413 and KD548 respectively when the size of the tumor grown into approximately 50 mm³. Here, the wild-type plasminogen Kringle domain 2 and TRAIL were used as controls. The treatment was performed 7 times in total every 2 days, and the anti-DR4 and DR5 Kringle domain variants KD413 and KD548 and the wild-type plasminogen Kringle domain 2 were directly injected at a dose of 20 mg/kg into the mice's tumors, and the TRAIL was directly injected at a dose of 15 mg/kg into the mice's tumors (Ashkenazi A & Herbst R S J Clin Invest, 118(6): 1979-1990, 2008, Ashkenazi A. et al., J Clin Invest 104(2): 155-162, 1999). The size of the tumor was calculated according to the Equation: $0.5 \times (\text{length})^2 \times (\text{width})^2$ by using values obtained by measuring the length and width of the tumor (van der Sloot A M. et al., Proc Natl Acd Sci USA, 103(23):8634-8639, 2006, Pukac L. et al., Br J Cancer 92(*)1430-1441, 2005). The mice into which the wild-type plasminogen Kringle domain 2, the anti-DR4 and -DR5 Kringle domain variants KD413 and KD548 and the TRAIL were injected showed no particular changes in behaviors, appearances and body weights, and sacrificed after 23 days of the injection of the tumor. Then, the tumors were extracted and weighed.

Figure 56:
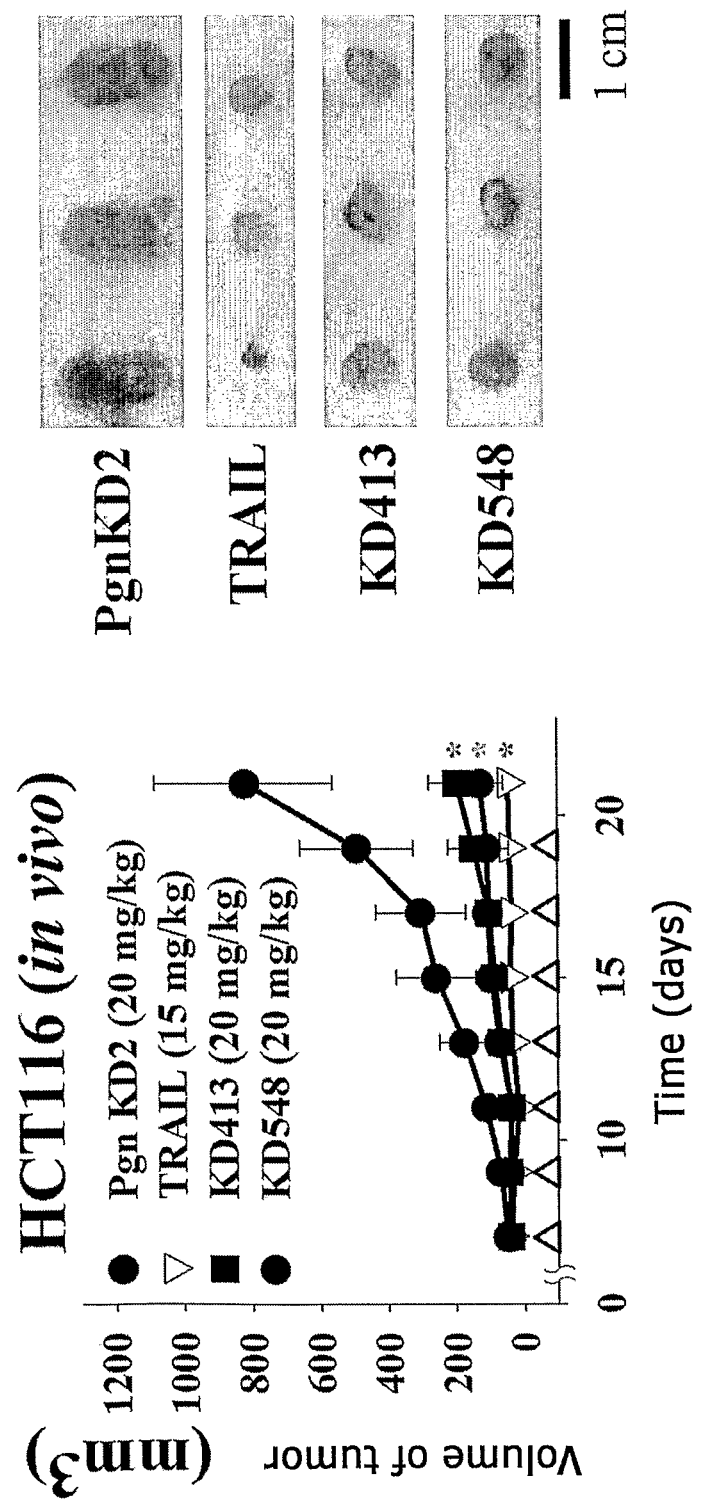
FIGS. 56-57 show data obtained by measuring volumes of tumors every 2 days and data on extracted tumors when, after the tumor inoculation, wild-type plasminogen Kringle domain 2, anti-DR4 and -DR5 Kringle domain variants KD413 and KD548, and TRAIL are directly injected into the tumors.
Figure 57:
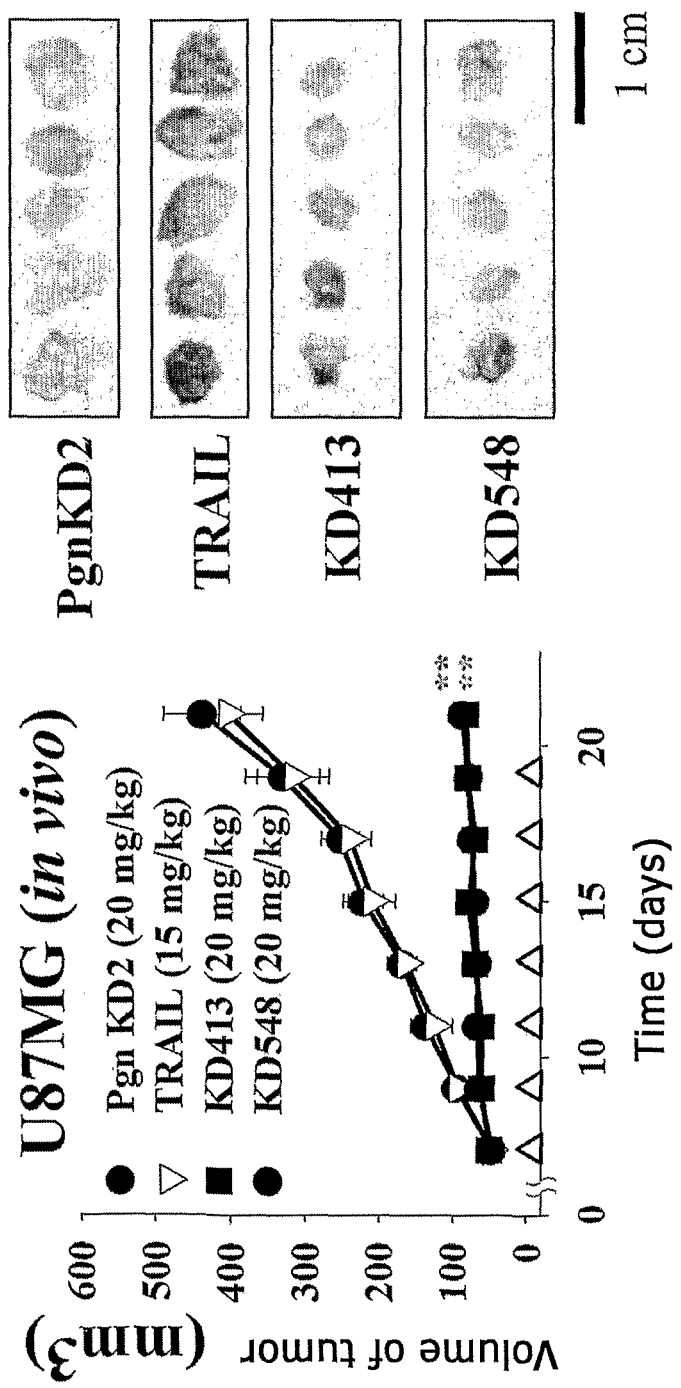

FIGS. 56 and 57 show data obtained by measuring volumes of tumors every 2 days and data on extracted tumors when, after the tumor inoculation, wild-type plasminogen Kringle domain 2, anti-DR4 and -DR5 Kringle domain variants KD413 and KD548, and TRAIL are directly injected into the tumors. FIG. 56 shows the results obtained from an HCT116 cell line, and FIG. 57 shows the results obtained from a TRAIL-resistant cell line, U87MG These animal experiment results indicate that the anti-DR4 and -DR5 Kringle domain variants, KD413 and KD548, effectively inhibit the tumor growth in vivo in a TRAIL-sensitive cell line, HCT116 and a resistant cell line, U87MG Example 15

Evaluation of Biological Activity of Anti-TNF α Protein Scaffold Variants Based on the Kringle Domain Structure The wild-type plasminogen Kringle domain 2 and infliximab (Remicade® Johnson & Johnson) were used as the control. Then, the cytotoxicity of the anti-TNFα Kringle domain variants KDT26 and a KDT26-Fc, which is an Fc-fused form of the anti-TNFα Kringle domain variants KDT26, against human TNFα was identified in a WEHI 164 cell line (mouse fibrosarcoma, ATCC CRL-1751) (MinSoo, Kim, et al., *J Mol Biol* 374(5):1374-1388, 2007, MooYoung, Song, et al., *Exp Mol Med* 40(1):35-42, 2008). The WHEI 164 cell line was inoculated threefold into a 96-well plate at a concentration of $1 \times 10^4$ cells/well and incubated in 10% (v/v) FBS-supplemented RPMI 1640 for 20 hours. Then, 2 μg/ml actinomycin D was added to the culture medium, and the culture medium was treated with 1 ng/ml human TNFα and then treated with 0.1 nM to 2 μM wild-type plasminogen Kringle domain 2, anti-TNFα Kringle domain variants KDT26 and KDT26-Fc, and infliximab, and incubated for 20 hours to evaluate the cell death using an MTT assay. $IC_{50}$ (50% inhibiting concentration) was determined using a Sigma plot software (Sigma plot, SPSS Inc.).

Figure 58:
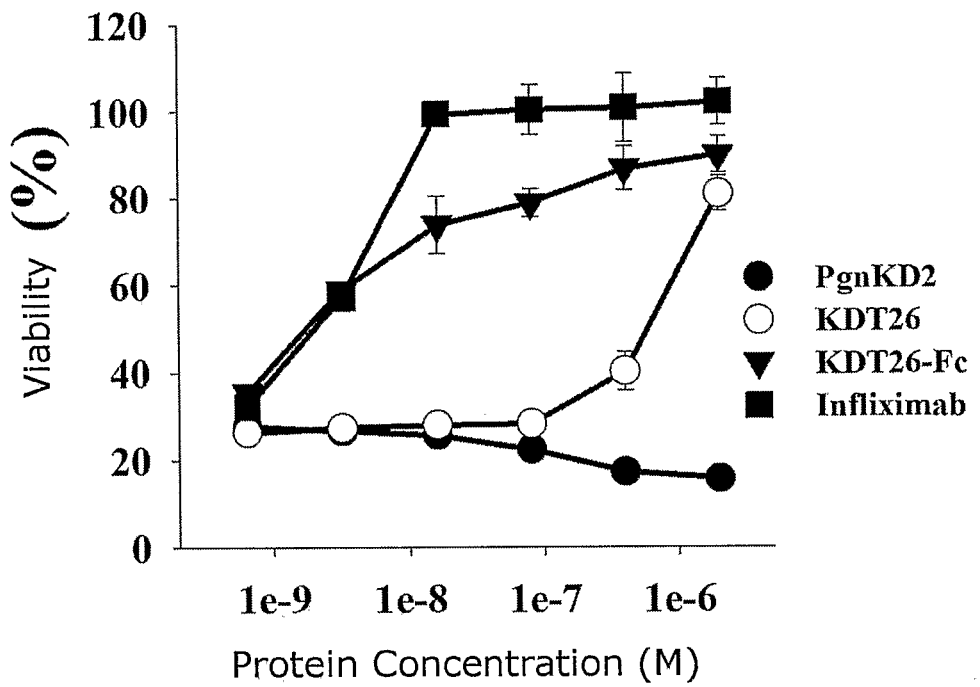
FIGS. 58-59 show the results obtained by identifying biological activities of the anti-TNFα Kringle domain variants in vitro and in vivo.

FIG. 58 shows the results obtained by evaluating the cell death inhibition of wild-type plasminogen Kringle domain 2, anti-TNFα Kringle domain variants KDT26 and KDT26-Fc and infliximab by TNFα in a WEHI 164 cell line. $IC_{50}$ of the infliximab, the KDT26 and the KDT26-Fc were measured to be approximately 2 nM, 0.78±0.03 μM, and 5.2±0.7 nM, respectively.

In order to perform a cytotoxicity-neutralizing test of TNFα in vivo, the KRT26-Fc (5 and 25 μg/mouse), the infliximab (5 and 25 μg/mouse) and a human antibody control IgG1 (Sigma) (5 μg/mouse) were intraperitoneally injected into 13 6-week-old C57BL/6 mice (Orientbio) under a germ-free condition. One hour after the intraperitoneal injections, 0.4 μg of human TNFα and 7 mg of D-galactosamine (GalN, Sigma), doses of which were confirmed to have a lethality rate of 90% at 12 hours after the administration, were intraperitoneally injected per mouse into the mice (MooYoung, Song, et al., *Exp Mol Med* 40(1):35-42, 2008). The viability rate of mice was recorded every 6 hours, and analyzed using a log-rank test.

Figure 59:
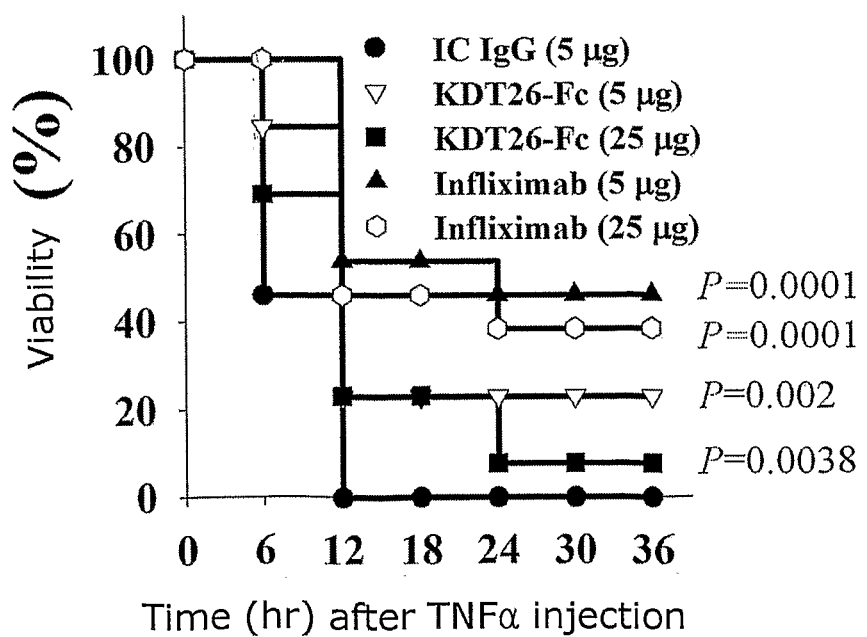

FIG. 59 shows log-rank (Mantel-Cox) test illustrating the in vivo inhibition of TNFα mediated toxicity of human IgG1 infliximab and KDT26-Fc as the control. The P-values are indicated at the right. Here p-Values were measured to be 0.0001 in a mouse into which the infliximab was injected at a dose of 5 μg/mouse, 0.0001 in a mouse into which the infliximab was injected at a dose of 25 μg/mouse, 0.002 in a mouse into which the KDT26-Fc was injected at a dose of 5 μg/mouse, and 0.0038 in a mouse into which the KDT26-Fc was injected at a dose of 25 μg/mouse. This indicates that the anti-TNFα Kringle domain variant KDT26-Fc effectively acts as an animal model.

Example 16

A Method for Preparing Homo-Oligomers Using the Monomers of the Kringle Domain Scaffold Variant which Binds to a Same Target Molecule The advantages of the homo-oligomers as described in example 2 are as follows: the affinity for target molecules is increased due to avidity effect, the biological activities of the target molecule are effectively able to be controlled by the combination of monomers which bind various sites of the target molecules and they are advantageous in the pharmacokinetics aspect since the size of homo-oligomers is larger than that of monomer.

The homo-dimers were constructed by linking the monomers of anti-DR4 Kringle domain variants, KD413 and KD415; anti-DR5 Kringle domain variants, KD506 and KD548; and an anti-TNFα Kringle domain variant, KDT26, using a linker of $(Gly-Gly-Gly-Gly-Ser)_4[(G_4S)_4]$ between the Kringle domains.

Figure 60:
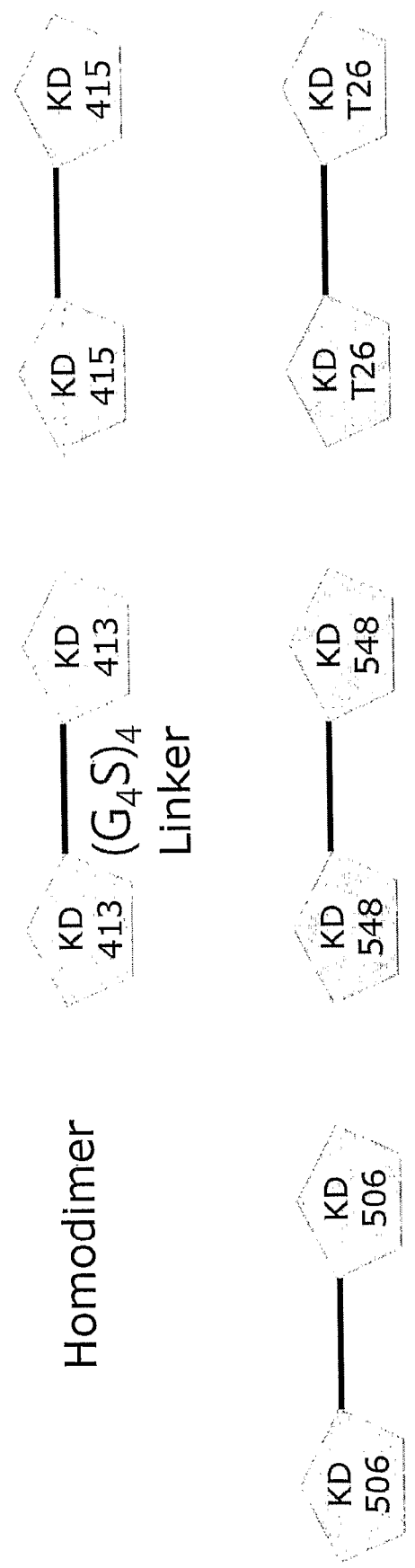
FIGS. 60-64 show schematic pictures of homo-dimers that constructed by linking anti-DR4 Kringle domain variants, KD413, and KD415, anti-DR5 Kringle domain variants, KD506, and KD548, and anti-TNFα Kringle domain variant KDT 26 with using the $(G_4S)_4$ linker, and also represents the affinity of the homo-dimers against the target molecules which is assayed by ELISA.

In other words, the Kringle domain homo-dimers which have $(G_4S)_4$ linker was cloned in frame into a yeast *Pichia pastoris* expression vector (pPICZaA, Invitrogen, USA), in which KD413, KD415, KD506, KD548, and KDT26 had been cloned, using the restriction enzymes BamHI/AflII (FIG. 60). In this case, the *Pichia* yeast expression vector was designed to contain a sequence of AOX3 promotor-MFa-secreting signal sequence-Kringle domain-myc tag-6×His tag (pPICZaA, Invitrogen, USA).

The expression and purification of the constructed Kringle domain homo-dimers were performed with the same method as described in example 8.

Figure 61:
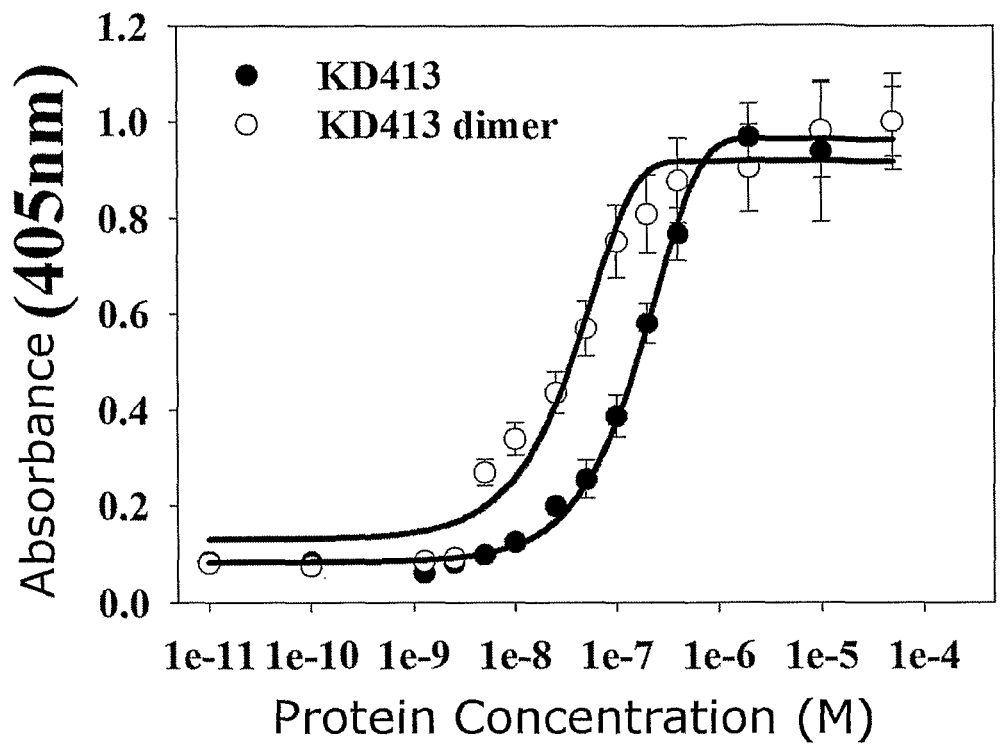
Figure 61:
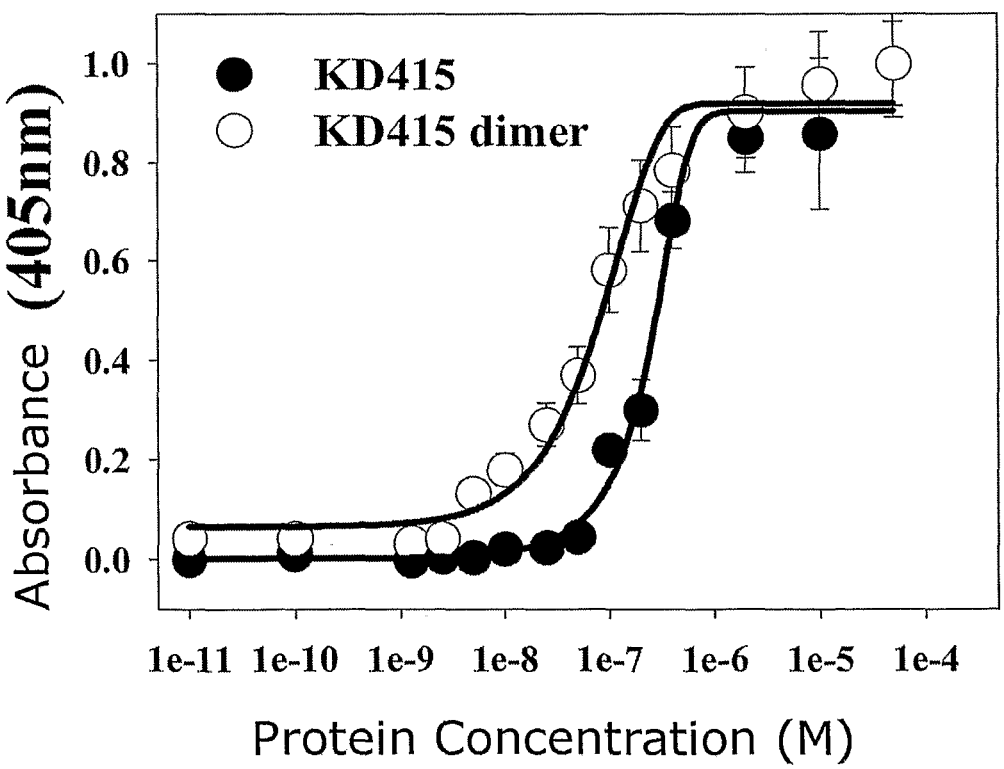
Figure 62:
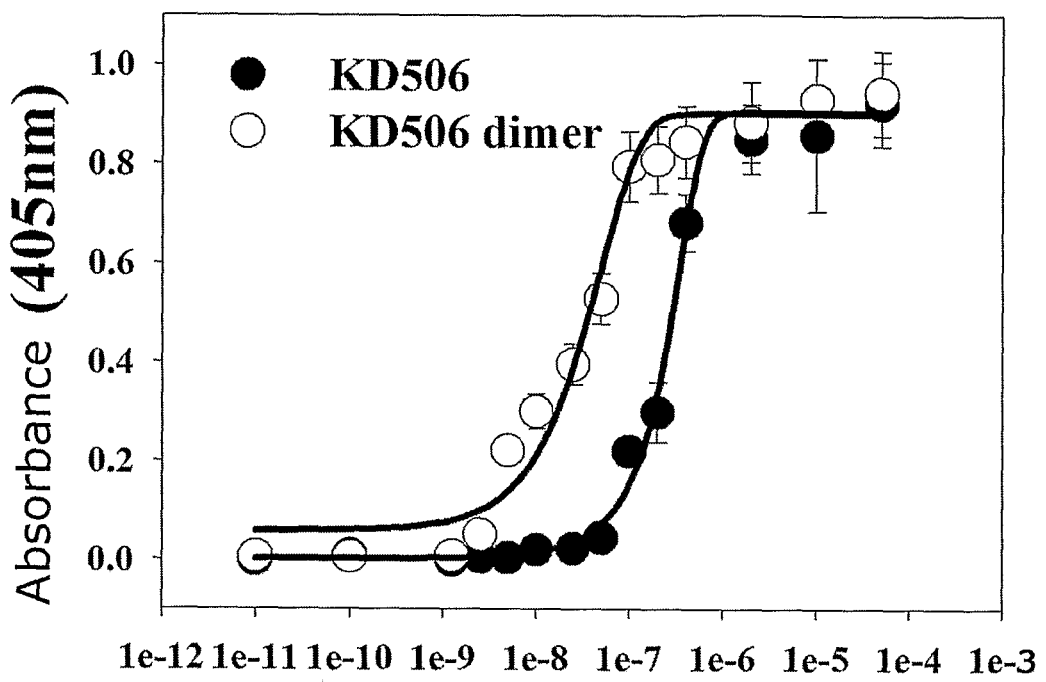
Figure 62:
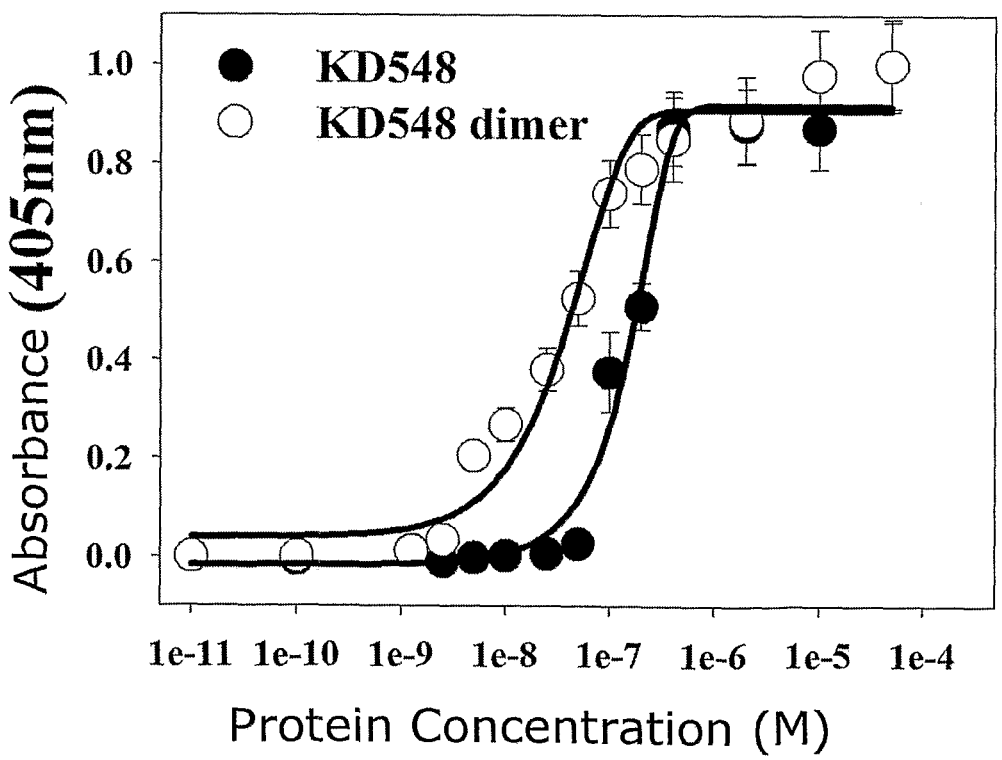
Figure 63:
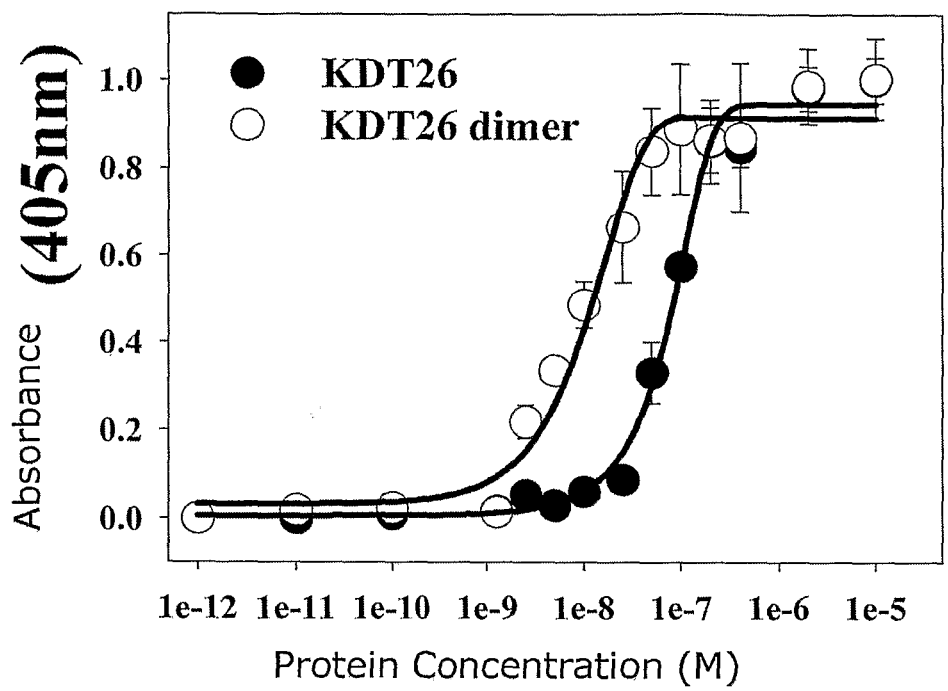

Also, the ELISA assay was performed to measure the affinity of the constructed Kringle domain homo-dimers against the target molecules, as described in example 8 and the results of the ELISA assay were compared with those of Kringle domain variant monomers (FIGS. 61, 62 and 63).

FIGS. 60-63 show schematic pictures of homo-dimers that constructed by linking anti-DR4 Kringle domain variants KD413, and KD415, anti-DR5 Kringle domain variants KD506, and KD548, and anti-TNFα Kringle domain variant KDT26 using the $(G_4S)_4$ linker, and also represents the affinity of the homo-dimers against the target molecules which is assayed by ELISA.

FIG. 60 shows a schematic picture of the constructed homo-dimers. FIG. 61 shows the affinity of the anti-DR4 KD413 and KD415 homo-dimers against target molecule DR4 which assayed by ELISA. The affinity value of the anti-DR4 KD413 homo-dimer is 43±5 nM, and the affinity value of the anti-DR4 KD415 homo-dimer is 87±6 nM. FIG. 62 shows the affinity of the anti-DR5 KD506 and KD548 homo-dimers against target molecule DR5 which assayed by ELISA. The affinity value of the anti-DR5 KD506 homo-dimer is 31±3 nM, and the affinity value of the anti-DR5 KD548 homo-dimer is 53±7 nM. FIG. 63 shows the affinity of the anti-TNFα KDT26 homo-dimer against target molecule TNFα which assayed by ELISA. The affinity value of the anti-TNFα KDT26 homo-dimer is 8±1 nM.

The experimental results show that when the Kringle domain variant monomers are converted to the Kringle domain variant homo-dimers, the affinity against target molecules is increased about 10 times due to avidity effect.

Example 17

A Method for Preparing Multispecific Oligomers by Linking Kringle Domain Variant with Different Target Binding Specificity The hetero-dimer was constructed by linking the monomers of anti-DR4 Kringle domain variant, KD413 and KD415, and anti-DR5 Kringle domain variant, KD506, using the $(G_4S)_4$ linker, as described in Example 16.

The expression and purification of the constructed Kringle domain hetero-dimer were performed with the same method as described in example 8.

FIGS. 64-68 show a schematic picture of hetero-dimer that constructed by linking anti-DR4 Kringle domain variant, KD413 and KD415, and anti-DR5 Kringle domain variant, KD506, with using the $(G_4S)_4$ linker, and also represents the affinity of the hetero-dimers against the target molecules which is assayed by ELISA.

Figure 64:
Figure 64:

FIG. 64 shows a schematic picture of the constructed hetero-dimers, KD413-KD415 and KD413-KD506.

Figure 65:
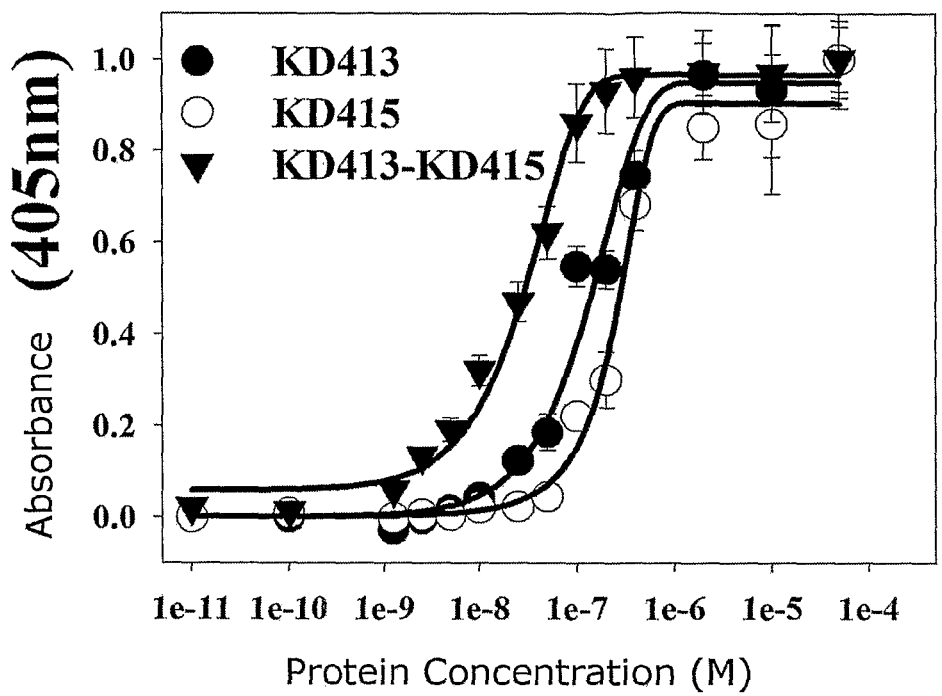
Figure 66:
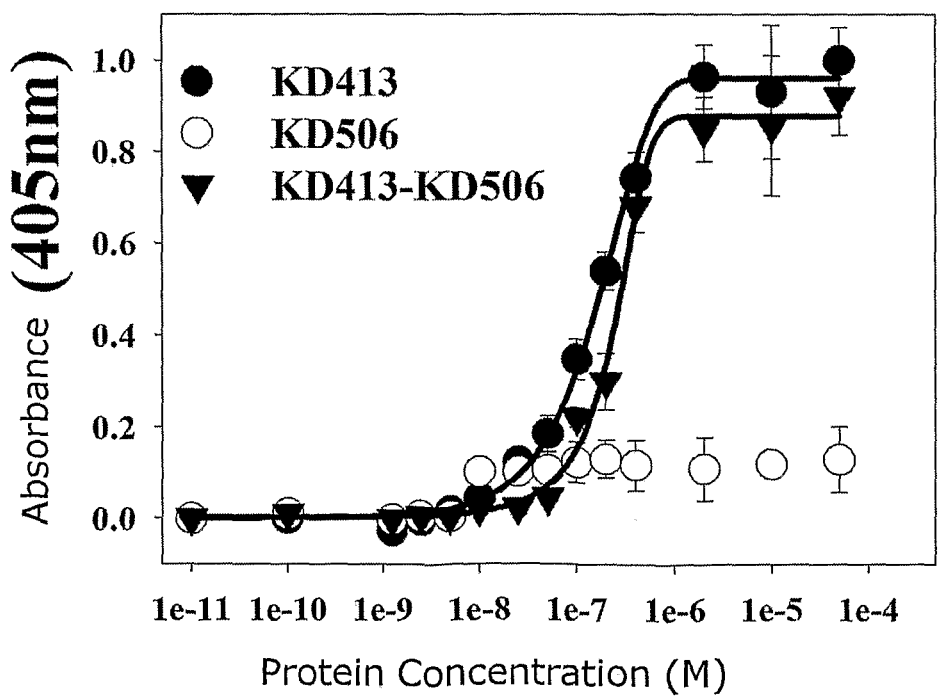
Figure 67:
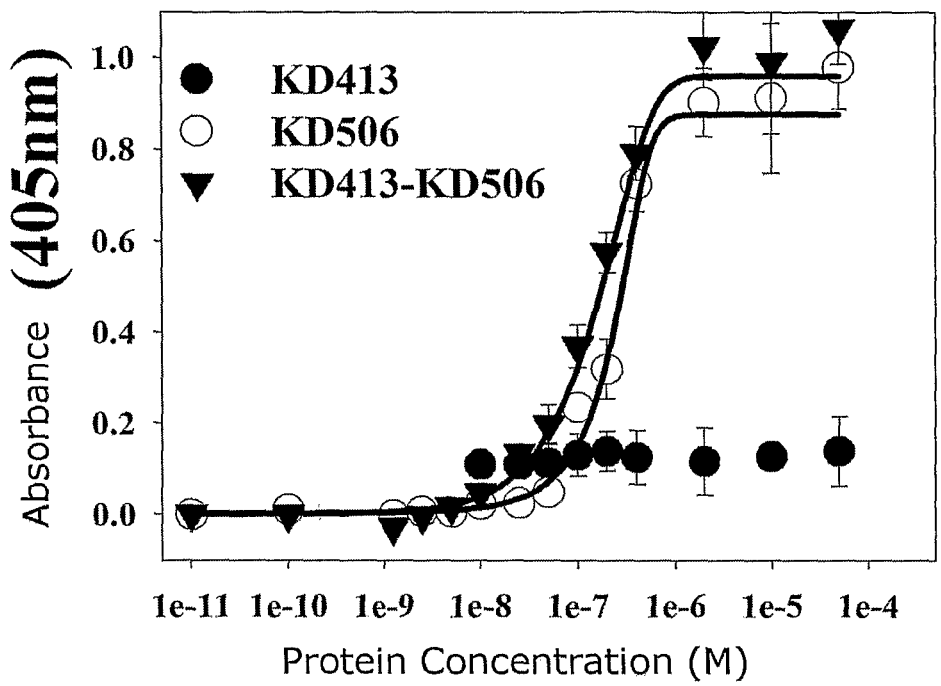
Figure 68:
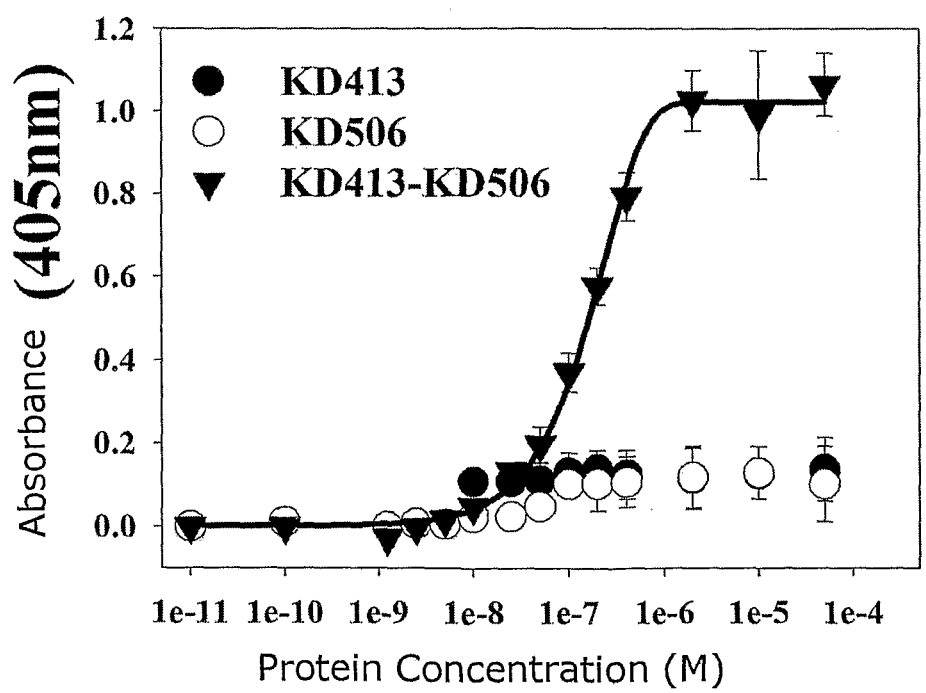

FIG. 65 shows the affinity of the KD413-KD415 hetero-dimer against target molecule DR4, FIG. 66 shows the affinity of the KD413-KD506 hetero-dimer against target molecule DR4 (left panel) and DR5 (right panel), and FIG. 67 shows the affinity of KD413-KD506 against plate-coated DR4 and soluble DR5, which was assayed by sandwich ELISA. As data show, KD413-KD415 hetero-dimer shows much higher affinity than their respective monomer because they recognize different regions of DR4 (FIG. 65). KD413-KD506 hetero-dimer binds to both DR4 and DR5 (FIG. 66), which was confirmed by the sandwich ELISA (FIG. 67). However, KD413 binds to only DR4 and KD506 binds to only DR5.

The experimental results show that when the two Kringle domain variants which bind to different target molecules are linked to the Kringle domain variant hetero-dimers, the Kringle domain variants obtain the bi-specificity.

Example 18

Binding Loop Mapping of Kringle Domain Variants that Specifically Bind to DR4, DR5, or TNFα

The Kringle domain has seven loops as described in example 1 and the protein scaffold library based on the Kringle domain was constructed by modifying all the seven loops. As a result, anti-DR4 Kringle domain variants, KD413, and KD415, anti-DR5 Kringle domain variants, KD506, and KD548, and anti-TNFα Kringle domain variant KDT26 contain seven loops which are able to bind target molecules. To investigate which loops out of the seven loops are involved in recognition for the target molecules, some loops of the anti-DR4 Kringle domain variants, KD413, and KD415, anti-DR5 Kringle domain variants, KD506, and KD548, and anti-TNFα Kringle domain variant KDT26 were back-mutated with wild-type Plasminogen Kringle domain 2. Clones that loops 1, 2, 3, and 4 are maintained with the amino acid sequences of the anti-DR4 Kringle domain variants, KD413, and KD415, anti-DR5 Kringle domain variants, KD506, and KD548, and anti-TNFα Kringle domain variant KDT26 Kringle domain variant and the rest of the loops have the with amino acid sequence of the wild-type Plasminogen Kringle domain 2 are named as KD413L1234, KD415L1234, KD506L1234, KD548L1234, and KDT26L1234, respectively. By using the same method, Clones that loops 5, 6, and 7 are maintained with amino acid sequence of Kringle domain variant and the rest of the loops have the with amino acid sequence of the wild-type Plasminogen Kringle domain 2 are named as KD413L567, KD415L567, KD506L567, KD548L567, and KDT26L567, respectively. Clones that loops 5 and 6 are maintained with amino acid sequence of Kringle domain variant and the rest of the loops have the with amino acid sequence of the wild-type Plasminogen Kringle domain 2 are named as KD413L56, KD415L56, KD506L56, KD548L56, and KDT26L56, respectively. Clone that loop 5 is maintained with amino acid sequence of Kringle domain variant and the rest of the loops have the with amino acid sequence of the wild-type Plasminogen Kringle domain 2 are named as KD413L5, KD415L5, KD506L5, KD548L567, and KDT26L5, respectively. The newly constructed clones were cloned into the yeast surface display vector, pCTCON, as described in detail in Example 3.

Figure 69:
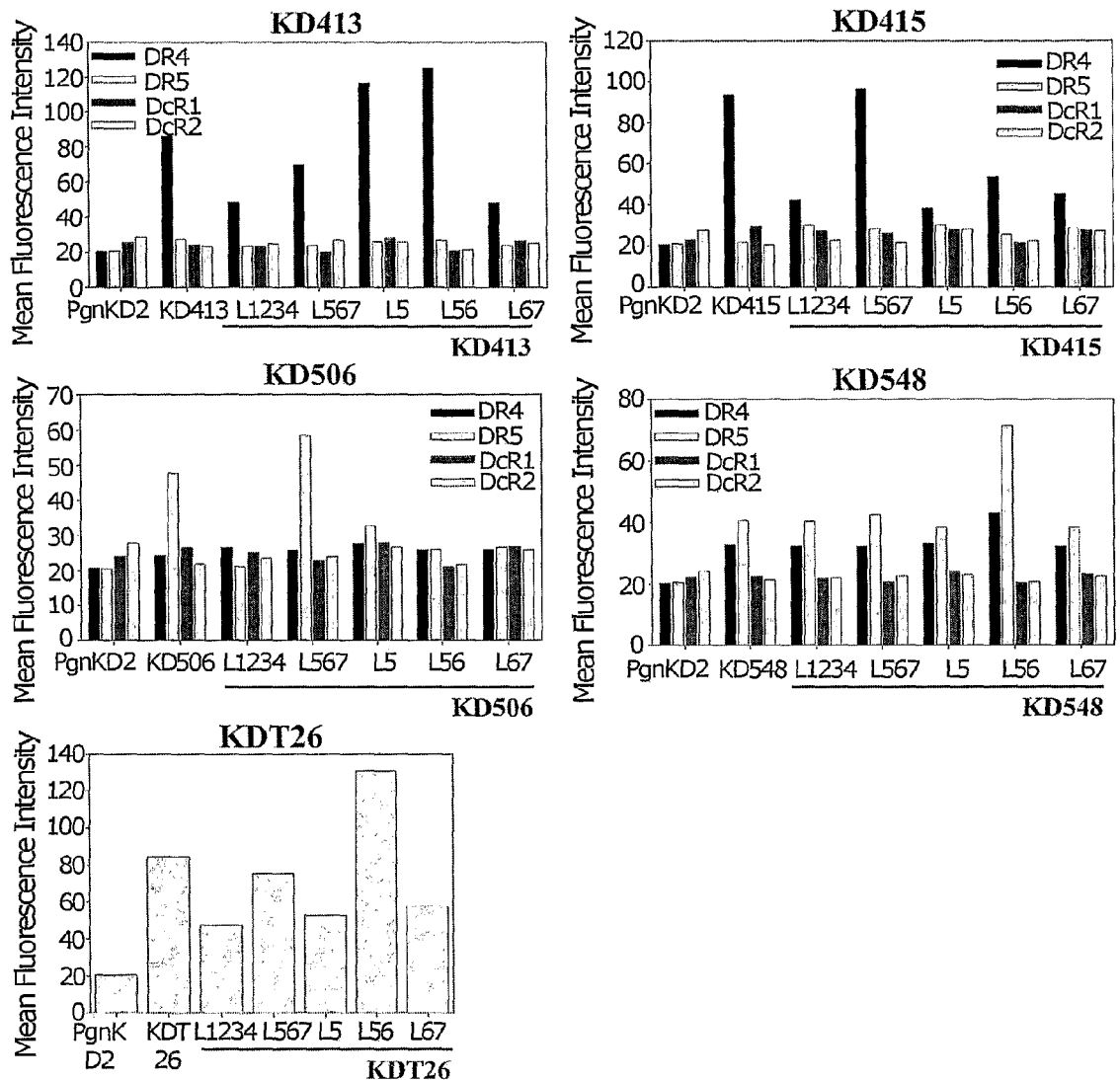
FIG. 69 shows the analysis of binding loop of Kringle domain variants selected against each target molecule. Briefly, each loop of the Kringle domain variants was back-mutated with the amino acid sequences of wild-type Plasminogen Kringle domain 2 and then expressed on the surface of the yeast cell, and the binding activities against DR4, DR5, DcR1, DcR2 and TNFα were analyzed with flow cytometry and then the level of the binding was assayed with MFI (mean fluorescence intensity).

FIG. 69 shows the analysis of binding activities of the newly constructed clones, which were expressed on the yeast cell surface, for DR4, DR5, DcR1, and DcR2, which were analyzed with flow cytometry, and then the level of the binding was assayed with MFI (mean fluorescence intensity). KD413 binds only to DR4 without cross reactivity with other target molecules, and KD413L56 has the highest affinity with target molecule DR4. Therefore, the result indicates that loops 5 and 6 are very important to binding of target molecule DR4. KD415 binds only to DR4 without cross reactivity with other target molecules, and KD415L567 has the highest affinity with target molecule DR4. Therefore, the result indicates that loops 5, 6, and 7 are very important to binding of target molecule DR4. KD506 binds only to DR5 without cross reactivity with other target molecules, and KD506L567 has the highest affinity with target molecule DR5. Therefore, the result indicates that loops 5, 6, and 7 are very important to binding of target molecule DR5. KD548 binds to both DR4 and DR5 as described in example 8, and KD548L56 has the highest affinity with target molecule DR5. Therefore, the result indicates that loop 5 and 6 are very important to binding of target molecule DR5. KDT26 binds only to TNFα without cross reactivity with other target molecules, and KDT26L56 has the highest affinity with target molecule TNFα. Therefore, the result indicates that loop 5 and 6 are very important to binding of target molecule TNFα.

Example 19

A Method for Preparing Multivalent Kringle Monomers or Multispecific Kringle Monomers by Grafting Target Binding Loops of the Kringle Monomer into Non-Binding Loops of Kringle Domain Monomer with the Same or Different Target Specificity In Example 18, by binding loop mapping analyses, the recognition loops of selected Kringle domain variants against DR4, DR5 and TNFα were identified. By grafting the binding loops into other loops, which are not or weakly participated in the binding with a target molecule, of the same or different Kringle domain monomers, multivalent Kringle monomers and multispecific Kringle monomers were constructed.

Figure 70:
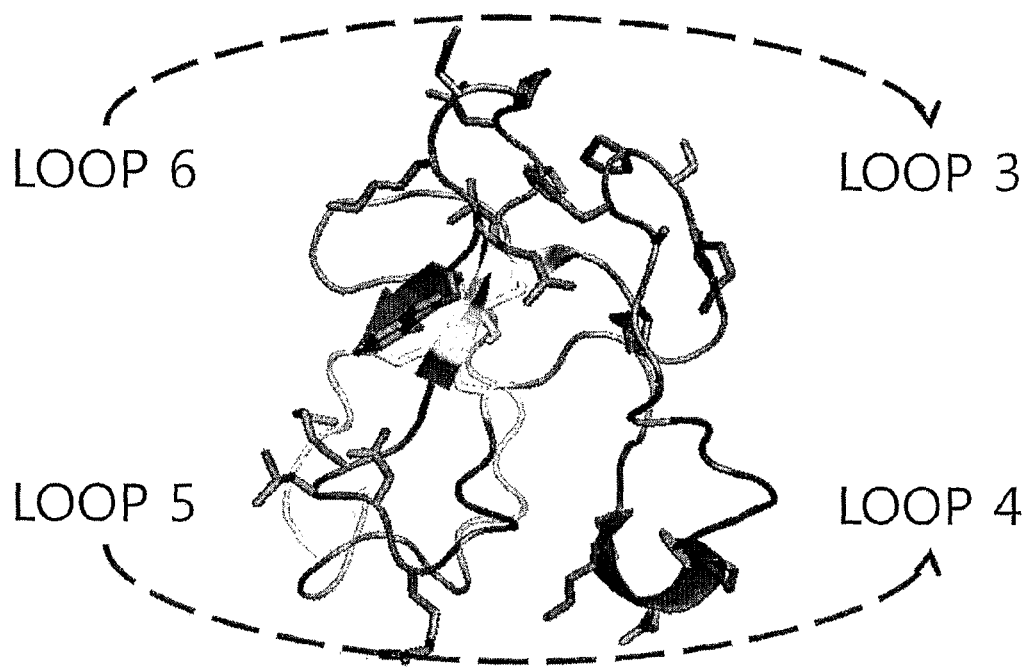
FIG. 70 shows example of grafting loops of Kringle domain variants as a schematic picture. For example, the picture schematically shows that loop 5 and 6 of Kringle domain are grafted to loops 3 and 4 which are oppositely oriented in three-dimensional structure and the structure of loop is mostly similar to that of the loops 5 and 6.

In anti-DR4 KD413, since loops 5 and 6 play an important role in binding to target molecule DR4, loops 5 and 6 of the KD413 was grafted to loops 3 and 4 of the KD413 which are oppositely oriented in three-dimensional structure, as shown in FIG. 70. The newly constructed clone was named as KD413-4. Further, loops 5 and 6 of KD413 was grafted to loops 3 and 4 of KD506 which are oppositely oriented in three-dimensional structure since in anti-DR5 KD506, loops 5, 6 and 7 play an important role in binding to target molecule DR5. The newly constructed clone was named as KD506-4. Also, loops 5 and 6 of KD548 was grafted to loops 3 and 4 of the KD413, resulting in the clone named as KD413-5

FIG. 70 shows example of grafting loops of Kringle domain variants as a schematic picture. For example, the picture schematically shows that loop 5 and 6 of Kringle domain are grafted to loops 3 and 4 which are oppositely oriented in three-dimensional structure and the structure of loop is mostly similar to that of the loops 5 and 6.

Figure 71:
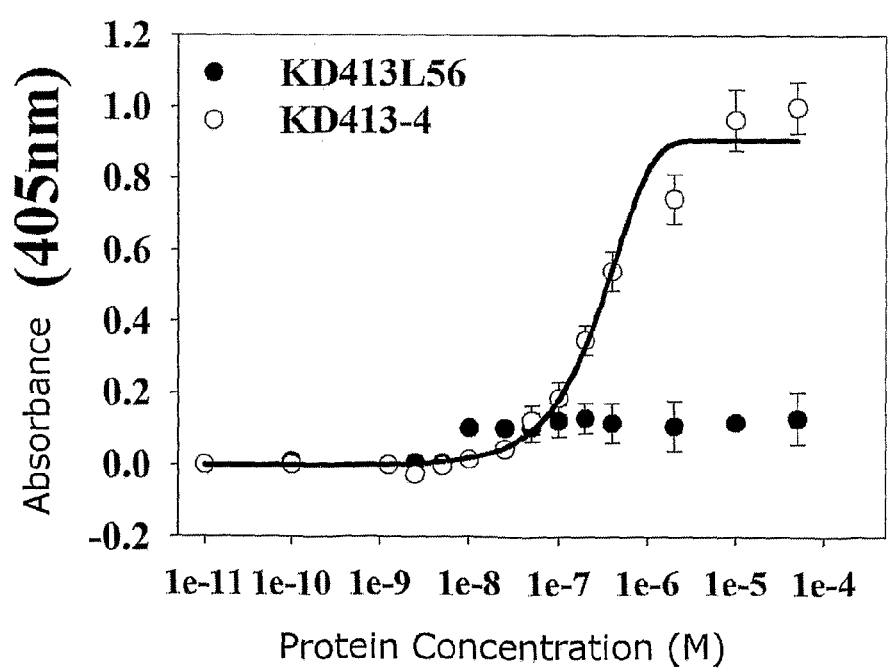
FIGS. 71-73 are quantitative results that Kringle domain variant KD413-4 constructed as the bivalent monomer and Kringle domain variants, KD506-4 and KD413-5, constructed as the bispecific monomer bind to the target molecules, by using sandwich ELISA.
Figure 72:
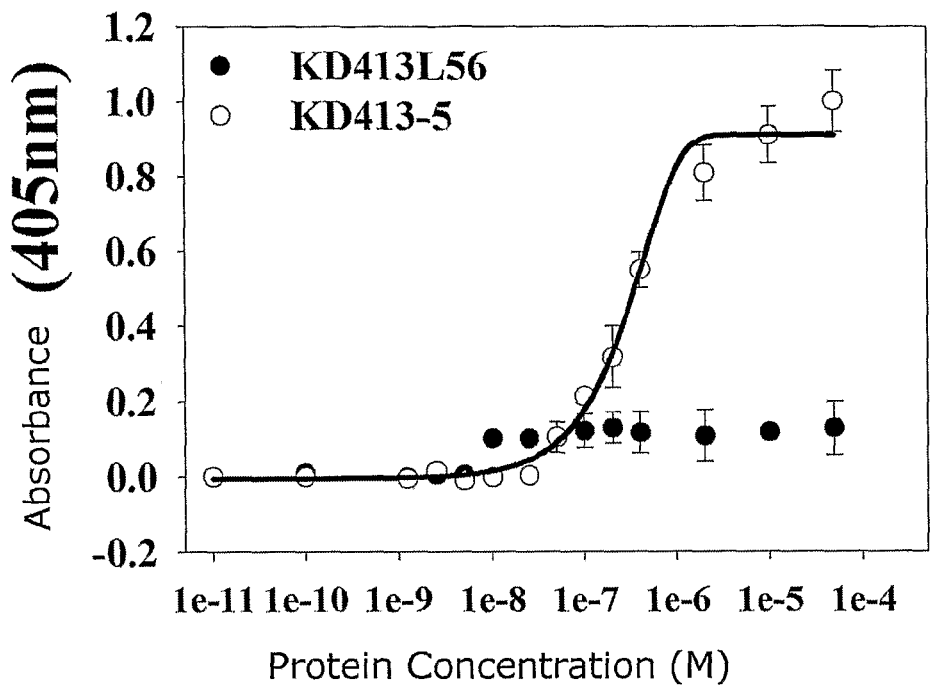
Figure 73:
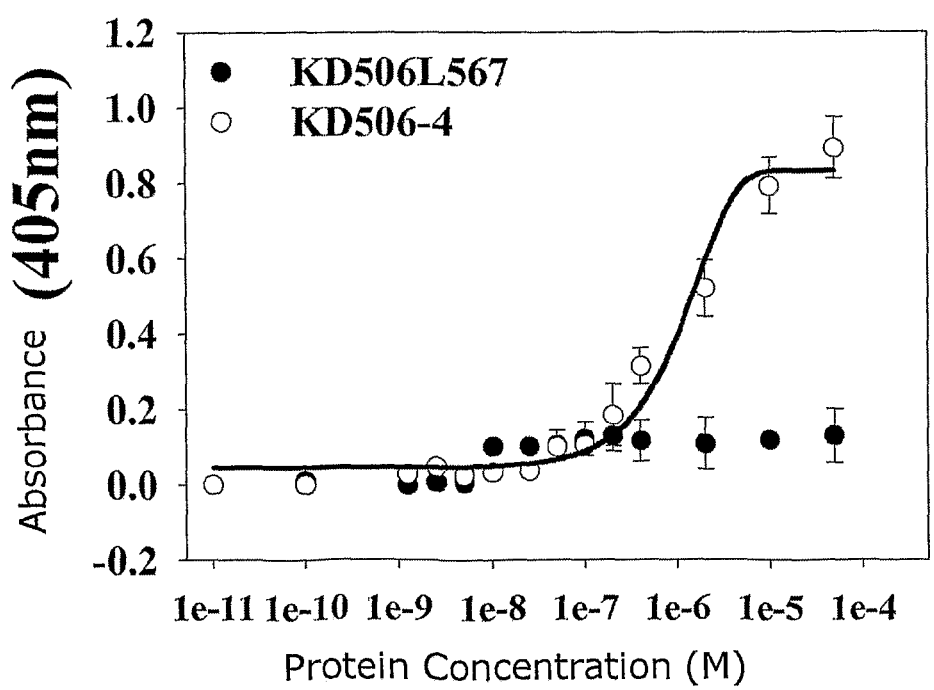

FIGS. 71-73 are quantitative results of sandwich ELISA that Kringle domain variant KD413-4 constructed as the bivalent monomer and Kringle domain variants KD506-4 and KD413-5 constructed as the bispecific monomer bind to the target molecules. FIG. 71 is the result that anti-DR4 bivalent monomer, KD413-4, simultaneously binds to target molecule DR4 which was plated-coated and the soluble DR4. KD415L56 is used as a control and it is confirmed that there is no bivalency. FIG. 72 is the result that anti-DR4/DR5 bispecific monomer, KD413-5, simultaneously binds to target molecule DR4 which was plated-coated and the soluble DR5. KD413L56 is used as a control and it is confirmed that there is no bivalency. FIG. 73 is the result that anti-DR4/DR5 bispecific monomer, KD506-4, simultaneously binds to target molecule DR5 which was plated-coated and the soluble DR4. KD506L567 is used as a control and it is confirmed that there is no bivalency.

These results suggest that multivalent monomers or multispecific monomers can be prepared by the grafting of the binding loops of the monomers of the protein scaffold variant, which binds to same site or different sites of the same target molecule or two or more different target molecules, to other loop regions of the same or different monomers.

The invention claimed is:

1. A method of preparing a protein scaffold library based on a Kringle domain, the method comprising:

providing an amino acid sequence comprising a Kringle domain, which comprises C1, G6, Y9, D10, G11, T16, G19, C22, Q23, W25, P30, H31, H33, G34, K48, N49, Y50, C51, R52, N53, P54, D55, P61, W62, C63, F64, T65, E73, L74, C75, P78, R79, and C80; and introducing artificial mutation in the amino acid sequence at one or more amino acid residues other than amino acid residues of C1, G6, Y9, D10, G11, T16, G19, C22, Q23, W25, P30, H31, H33, G34, K48, N49, Y50, C51, R52, N53, P54, D55, P61, W62, C63, F64, T65, E73, L74, C75, P78, R79, and C80, thereby producing a mutant amino acid sequence, which is part of the protein scaffold library.

2. The method according to claim 1, wherein the artificial mutation comprise deletion of at least one amino acid residue selected from the group consisting of amino acid residues 2, 3, 4, 5, 7, 8, 12, 13, 14, 15, 17, 18, 20, 21, 24, 26, 27, 28, 29, 32, 36, 37, 38, 39, 40, 41, 42, 43, 44, 45, 46, 47, 56, 57, 58, 59, 66, 67, 68, 69, 70, 71, 72, 76, and 77, wherein the deletion of at least one amino acid residue is designed to provide an amino acid sequence that does not exist in the nature.

3. The method according to claim 1, wherein the artificial mutation comprise replacement of at least one amino acid residue selected from the group consisting of amino acid residues 2, 3, 4, 5, 7, 8, 12, 13, 14, 15, 17, 18, 20, 21, 24, 26, 27, 28, 29, 32, 36, 37, 38, 39, 40, 41, 42, 43, 44, 45, 46, 47, 56, 57, 58, 59, 66, 67, 68, 69, 70, 71, 72, 76, and 77 with one amino acid residue for each replacement, the replacement amino acid residue being selected from the group consisting of serine, tyrosine, proline, histidine, threonine, asparagine, alanine, aspartate, glutamine, arginine, lysine, glutamic acid and glycine, wherein the replacement of at least one amino acid residue is designed to provide an amino acid sequence that does not exist in the nature.

4. The method according to claim 1, wherein introducing artificial mutation in the amino acid sequence comprises performing PCR on a naturally existing gene of the Kringle domain with primers; wherein the protein scaffold library comprises the an amino acid sequence of:

(SEQ ID NO: 19)
CXxXxGXxYDGXxXxTXxGXxCQXVVXxXxPHXHGXxXxXxXxXx

KNYCRNPDXxXxPWCFTXxXxXxXELCXxPRC wherein X represents an amino acid residue selected from the group consisting of serine, tyrosine, proline, histidine, threonine, asparagine, alanine or aspartate, and x represents an amino acid residue selected from the group consisting of glutamine, arginine, lysine, glutamic acid and glycine.

5. The method according to claim 4, wherein the primers are selected from the group consisting of SEQ ID NO: 1 to SEQ ID NO: 8.

6. The method according to claim 5, wherein the Kringle domain is a Kringle domain of human plasminogen.

7. The method according to claim 6, wherein the Kringle domain of the human plasminogen has an amino acid sequence set forth in SEQ ID NO: 49.

8. The method according to claim 6, wherein the Kringle domain of the human plasminogen has a DNA sequence set forth in SEQ ID NO: 50.

9. A method of producing a target-specific protein scaffold variant, the method comprising:
preparing a protein scaffold library by performing the method of claim 1;
screening the protein scaffold library to identify an amino acid sequence having specific affinity to a target molecule; and
isolating the identified amino acid sequence as a target-specific protein scaffold variant.

10. The method according to claim 9, wherein the target molecule comprises at least one selected from the group consisting of a death receptor (DR) 4, a death receptor (DR) 5, a tumor necrosis factor-α, a glycoprotein IIβIIIα receptor or glycoprotein IIβIIIα, a vascular endothelial growth factor (VEGF), a vascular endothelial growth factor receptor (VEGFR), a tyrosine kinase inhibitor, an epidermal growth factor receptor, a platelet-derived growth factor (PDGF), a platelet-derived growth factor receptor (PDGFR), a stem cell factor receptor (c-kit), an Fms-like tyrosine kinase-3 (Flt-3), interleukin 1, interleukin 6, interleukin 32, an interleukin 2 receptor, CD3, CD11a, CD14, CD15, CD16, CD20 CD32, CD64, and Raf.

11. A method of preparing a homo-oligomer or a hetero-oligomer, the method comprising:
providing two or more amino acid sequences by performing the method defined in claim 9 or 10, the two or more amino acid sequences having specific binding affinity to a single target molecule; and
combining the two or more amino acid sequences using a linker to provide an oligomer capable of binding to the single target molecule.

12. A method of preparing a homo-oligomer or a hetero-oligomer capable of binding to multi-target molecules at the same time, the method comprising:
providing two or more amino acid sequences by performing the method defined in claim 9 or 10, the two or more amino acid sequences comprising sequences having specific binding affinity to two or more different target molecules; and
combining the two or more amino acid sequences using a linker to provide an oligomer capable of binding to multi-target molecules at the same time.

13. A method of preparing a multivalent amino acid sequence or a multispecific amino acid sequence, the method comprising:
providing first and second amino acid sequences performing the method defined in claim 9 or 10, the first amino acid sequence comprising a first target binding loop capable of binding two or more sites of a single target molecule or capable of binding two or more different target molecules; and
grafting the first target binding loop to the second amino acid sequence.

* * * * *

SEQUENCE LISTING

<160> NUMBER OF SEQ ID NOS: 50

<210> SEQ ID NO 1
<211> LENGTH: 60
<212> TYPE: DNA
<213> ORGANISM: Artificial Sequence
<220> FEATURE:
<223> OTHER INFORMATION: Primer

<400> SEQUENCE: 1
ggtggtggtg gttctggtgg tggtggttct ggtggtggtg gttctgctag cgaggaatgt    60

<210> SEQ ID NO 2
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (11), (20), (26)
<223> OTHER INFORMATION: y is c or t
<220> FEATURE:
<221> NAME/KEY: misc_feature
<222> LOCATION: (12), (21), (27)
<223> OTHER INFORMATION: b is c or g or t; not a
<220> FEATURE:
<221> NAME/KEY: misc_feature
<222> LOCATION: (14), (23), (29)
<223> OTHER INFORMATION: k is g or t
<220> FEATURE:
<221> NAME/KEY: misc_feature
<222> LOCATION: (15), (24), (30)
<223> OTHER INFORMATION: n is a or c or g or t

<400> SEQUENCE: 2
gccgtcatac ybgkntcccy bgkncybgkn acattcctcg ctagcagaac    50

<210> SEQ ID NO 3
<211> LENGTH: 61
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (5), (20), (26), (35), (44), (56)
<223> OTHER INFORMATION: n is a or c or g or t
<220> FEATURE:
<221> NAME/KEY: misc_feature
<222> LOCATION: (6), (21), (27), (36), (45), (57)
<223> OTHER INFORMATION: m is a or c
<220> FEATURE:
<221> NAME/KEY: misc_feature
<222> LOCATION: (8), (23), (29), (38), (47)
<223> OTHER INFORMATION: v is a or c or g; not t
<220> FEATURE:
<221> NAME/KEY: misc_feature
<222> LOCATION: (9), (24), (30), (39), (48)
<223> OTHER INFORMATION: r is a or g

<400> SEQUENCE: 3
ggganmcvrg tatgacggcn mcvrgnmcvr gaccnmcvrg gganmcvrgt gccagnmctg    60
g                                                                    61

<210> SEQ ID NO 4
<211> LENGTH: 47
<212> TYPE: DNA
<213> ORGANISM: Artificial Sequence

```
<220> FEATURE:
<223> OTHER INFORMATION: primer
<220> FEATURE:
<221> NAME/KEY: misc_feature
<222> LOCATION: (17), (23), (41)
<223> OTHER INFORMATION: y is c or t
<220> FEATURE:
<221> NAME/KEY: misc_feature
<222> LOCATION: (18), (24), (42)
<223> OTHER INFORMATION: b is c or g or t; not a
<220> FEATURE:
<221> NAME/KEY: misc_feature
<222> LOCATION: (8), (20), (26), (32), (44)
<223> OTHER INFORMATION: k is g or t
<220> FEATURE:
<221> NAME/KEY: misc_feature
<222> LOCATION: (9), (21), (27), (33), (45)
<223> OTHER INFORMATION: n is a or c or g or t

<400> SEQUENCE: 4
tccatggkng tgtggcybgk ncybgkncca gknctggcac ybgkntc                  47

<210> SEQ ID NO 5
<211> LENGTH: 79
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (11), (20), (26), (32), (38), (44), (50)
<223> OTHER INFORMATION: n is a or c or g or t
<220> FEATURE:
<221> NAME/KEY: misc_feature
<222> LOCATION: (12), (21), (27), (33), (39), (45), (51)
<223> OTHER INFORMATION: m is a or c
<220> FEATURE:
<221> NAME/KEY: misc_feature
<222> LOCATION: (2), (23), (29), (35), (41), (47), (53)
<223> OTHER INFORMATION: v is a or c or g; not t
<220> FEATURE:
<221> NAME/KEY: misc_feature
<222> LOCATION: (3), (24), (30), (36), (42), (48), (54)
<223> OTHER INFORMATION: r is a or g

<400> SEQUENCE: 5
cvrgccacac nmccatggan mcvrgnmcvr gnmcvrgnmc vrgnmcvrgn mcvrgaagaa    60
ttactgtcgt aaccccgat                                                79

<210> SEQ ID NO 6
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17), (23)
<223> OTHER INFORMATION: y is c or t
<220> FEATURE:
<221> NAME/KEY: misc_feature
<222> LOCATION: (18), (24)
<223> OTHER INFORMATION: b is c or g or t; not a
<220> FEATURE:
<221> NAME/KEY: misc_feature
<222> LOCATION: (20), (26)
<223> OTHER INFORMATION: k is g or t
<220> FEATURE:
<221> NAME/KEY: misc_feature
<222> LOCATION: (21), (27)
<223> OTHER INFORMATION: n is a or c or g or t
```

<400> SEQUENCE: 6
ggtgaaacac caaggcybgk ncybgknatc ggggttacga cagtaatt          48

<210> SEQ ID NO 7
<211> LENGTH: 67
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20), (26), (32), (38), (50)
<223> OTHER INFORMATION: n is a or c or g or t
<220> FEATURE:
<221> NAME/KEY: misc_feature
<222> LOCATION: (21), (27), (33), (39), (51)
<223> OTHER INFORMATION: m is a or c
<220> FEATURE:
<221> NAME/KEY: misc_feature
<222> LOCATION: (2), (23), (29), (35), (53)
<223> OTHER INFORMATION: v is a or c or g; not t
<220> FEATURE:
<221> NAME/KEY: misc_feature
<222> LOCATION: (3), (24), (30), (36), (54)
<223> OTHER INFORMATION: r is a or g

<400> SEQUENCE: 7
cvrgccttgg tgtttcaccn mcvrgnmcvr gnmcvrgnmc gaactttgcn mcvrgccccg    60
ctgcaca                                                              67

<210> SEQ ID NO 8
<211> LENGTH: 75
<212> TYPE: DNA
<213> ORGANISM: Artificial Sequence
<220> FEATURE:
<223> OTHER INFORMATION: primer

<400> SEQUENCE: 8
atctcgagct attacaagtc ctcttcagaa ataagctttt gttcggatcc tggaggtgtt    60
gtgcagcggg gcybg                                                     75

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
ggtggtggtg gttctggtgg t                                              21

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
atctcgagct attacaagtc ctcttcag                                       28

<210> SEQ ID NO 11
<211> LENGTH: 22
<212> TYPE: DNA
<213> ORGANISM: Artificial Sequence
<220> FEATURE:
<223> OTHER INFORMATION: forward primer

<400> SEQUENCE: 11
gttccagact acgctctgca gg 22

<210> SEQ ID NO 12
<211> LENGTH: 24
<212> TYPE: DNA
<213> ORGANISM: Artificial Sequence
<220> FEATURE:
<223> OTHER INFORMATION: reverse primer

<400> SEQUENCE: 12
gattttgtta catctacact gttg 24

<210> SEQ ID NO 13
<211> LENGTH: 234
<212> TYPE: DNA
<213> ORGANISM: Artificial Sequence
<220> FEATURE:
<223> OTHER INFORMATION: kringle domain library
<220> FEATURE:
<221> NAME/KEY: misc_feature
<222> LOCATION: (4), (10), (19), (34), (40), (49), (58), (70), (76), (82), (94), (103), (109), (115), (121), (127), (133), (163), (169), (190), (196), (202), (208), (220)
<223> OTHER INFORMATION: n is a or c or g or t
<220> FEATURE:
<221> NAME/KEY: misc_feature
<222> LOCATION: (5), (11), (20), (35), (41), (50), (59), (71), (77), (83), (95), (104), (110), (116), (122), (128), (134), (164), (170), (191), (197), (203), (209), (221)
<223> OTHER INFORMATION: m is a or c
<220> FEATURE:
<221> NAME/KEY: misc_feature
<222> LOCATION: (7), (13), (22), (37), (43), (52), (61), (79), (85), (106), (112), (118), (124), (130), (136), (166), (172), (193), (199), (205), (223)
<223> OTHER INFORMATION: v is a or c or g; not t
<220> FEATURE:
<221> NAME/KEY: misc_feature
<222> LOCATION: (8), (14), (23), (38), (44), (53), (62), (80), (86), (107), (113), (119), (125), (131), (137), (167), (173), (194), (200), (206), (224)
<223> OTHER INFORMATION: r is a or g

<400> SEQUENCE: 13
tgtnmcvrgn mcvrgggANM cvrgtatgac ggcnmcvrgn mcvrgaccnm cvrggganmc 60
vrgtgccagn mctggnmcvr gnmcvrgcca cacnmccatg ganmcvrgnm cvrgnmcvrg 120
nmcvrgnmcv rgnmcvrgaa gaattactgt cgtaaccccg atnmcvrgnm cvrgccttgg 180
tgtttcaccn mcvrgnmcvr gnmcvrgnmc gaactttgcn mcvrgccccg ctgc 234

<210> SEQ ID NO 14
<211> LENGTH: 234
<212> TYPE: DNA
<213> ORGANISM: Artificial Sequence
<220> FEATURE:
<223> OTHER INFORMATION: kringle domain library

<400> SEQUENCE: 14
tgtaacgggg acgggggaga caggtatgac ggcaacaagc acaagaccct caagggatac 60
cggtgccagc actggaccag gaccaagcca caccaccatg gagtcgggca ccgggacaag 120
atccggtaca gggaccagaa gcattactgt cgtaaccccg ataccgagac cgggccttgg 180
tgtttcacca acaagaacgg ggacaggtac gaactttgcc acgagccccg ctgc 234

<210> SEQ ID NO 15
<211> LENGTH: 234

```
<212> TYPE: DNA
<213> ORGANISM: Artificial Sequence
<220> FEATURE:
<223> OTHER INFORMATION: kringle domain library

<400> SEQUENCE: 15
tgtaaccagc acaagggatc caggtatgac ggccacaaga accggaccgt caagggaaac    60
cagtgccagg actggtacaa gccccagcca cacttccatg gactcaggga caagtccaag   120
aacaagttca agttcaagaa gaattactgt cgtaaccccg atgccaggac caggccttgg   180
tgtttcaccc acgaggacaa ggacgagtac gaactttgcg acgggccccg ctgc         234

<210> SEQ ID NO 16
<211> LENGTH: 234
<212> TYPE: DNA
<213> ORGANISM: Artificial Sequence
<220> FEATURE:
<223> OTHER INFORMATION: kringle domain library

<400> SEQUENCE: 16
tgtcccgagg accagggaga cgagtatgac ggccacgagc acaagaccca caggggaaac    60
aggtgccagt cctggtacag gcccaagcca cacaaccatg gacacaggat caaggaccgg   120
tacaagtaca aggtcaagaa gaattactgt cgtaaccccg atacccaggc ccggccttgg   180
tgttttacca accggcacag ggacgagcac gaactttgcg accagccccg ctgc         234

<210> SEQ ID NO 17
<211> LENGTH: 234
<212> TYPE: DNA
<213> ORGANISM: Artificial Sequence
<220> FEATURE:
<223> OTHER INFORMATION: kringle domain library

<400> SEQUENCE: 17
tgtaccaagc accggggaac caagtatgac ggccacaaga acaggaccta ccagggaaac    60
aggtgccaga actggtcccg gaacaagcca caccaccatg gagacaagta cgagaacaag   120
ttccgggctc gggctcaaga agaattactg tcgtaacccc gatgacaagg ccgagccttg   180
gtgtttaccg gacggggaca ggaacgggat cgaactttgc tcaagccccg ctgc         234

<210> SEQ ID NO 18
<211> LENGTH: 234
<212> TYPE: DNA
<213> ORGANISM: Artificial Sequence
<220> FEATURE:
<223> OTHER INFORMATION: kringle domain library

<400> SEQUENCE: 18
tgtacccagc ccgagggacc caggtatgac ggcaacgggc acaagaccca ccggggacac    60
cagtgccagg cctggcccaa ggcccggcca cacgaccatg gactcaagca cagggacagg   120
ctccaggtcc gggacaagaa gaattactgt cgtaaccccg atgccgagga cgggccttgg   180
tgtttcaccc accggcacgg gtacgggcac gaactttgcg acgggccccg ctgc         234

<210> SEQ ID NO 19
<211> LENGTH: 78
<212> TYPE: PRT
<213> ORGANISM: Artificial Sequence
<220> FEATURE:
<223> OTHER INFORMATION: mutant
<220> FEATURE:
<221> NAME/KEY: misc_feature
<222> LOCATION: (2), (4), (7), (12), (14), (17), (20), (24), (26), (28),
      (32) (35), (37), (39), (41), (43), (45), (55), (57), (64), (66),
```

(68), (70), (74)
<223> OTHER INFORMATION: Xaa is Ser, Tyr, Pro, His, Thr, Asn, Ala or Asp
<220> FEATURE:
<221> NAME/KEY: misc_feature
<222> LOCATION: (3), (5), (8), (13), (15), (18), (21), (27), (29), (36),
      (38), (40), (42), (44), (46), (56), (58), (65), (67), (69), (75)
<223> OTHER INFORMATION: Xaa is Gln, Arg, Lys, Glu or Gly

<400> SEQUENCE: 19

Cys Xaa Xaa Xaa Gly Xaa Xaa Tyr Asp Gly Xaa Xaa Xaa Xaa Thr
 1               5                  10                  15

Xaa Xaa Gly Xaa Xaa Cys Gln Xaa Trp Xaa Xaa Xaa Xaa Pro His Xaa
                20                  25                  30

His Gly Xaa Xaa Xaa Xaa Xaa Xaa Xaa Xaa Xaa Xaa Lys Asn
             35                  40                  45

Tyr Cys Arg Asn Pro Asp Xaa Xaa Xaa Xaa Pro Trp Cys Phe Thr Xaa
 50                  55                  60

Xaa Xaa Xaa Xaa Xaa Xaa Glu Leu Cys Xaa Xaa Pro Arg Cys
 65                  70                  75

<210> SEQ ID NO 20
<211> LENGTH: 78
<212> TYPE: PRT
<213> ORGANISM: Artificial Sequence
<220> FEATURE:
<223> OTHER INFORMATION: KD404

<400> SEQUENCE: 20

Cys Ser Arg Asp Lys Gly Tyr Arg Tyr Asp Gly Asp Gly Asn Lys Thr
 1               5                  10                  15

Leu Lys Gly His Lys Cys Gln His Trp Thr Lys Ser Lys Pro His Asp
                20                  25                  30

His Gly Tyr Arg His Lys Leu Gly Asn Glu Asp Lys Phe Lys Lys Asn
             35                  40                  45

Tyr Cys Arg Asn Pro Asp Thr Arg Ala Gly Pro Trp Cys Phe Thr Asp
 50                  55                  60

Gln Tyr Arg Asp Arg Asp Glu Leu Cys Tyr Gln Pro Arg Cys
 65                  70                  75

<210> SEQ ID NO 21
<211> LENGTH: 78
<212> TYPE: PRT
<213> ORGANISM: Artificial Sequence
<220> FEATURE:
<223> OTHER INFORMATION: KD408

<400> SEQUENCE: 21

Cys Asp Arg His Lys Gly Pro Lys Tyr Asp Gly Phe Arg Asp Arg Thr
 1               5                  10                  15

His Lys Gly His Lys Cys Gln Tyr Trp Asp Lys Pro Arg Pro His His
                20                  25                  30

His Gly His Lys His Gly Asp Glu Phe Arg Asn Arg Leu Gly Lys Asn
             35                  40                  45

Tyr Cys Arg Asn Pro Asp Ser Gln Ala Glu Pro Trp Cys Phe Thr His
 50                  55                  60

Lys Asp Lys Tyr Lys Tyr Glu Leu Cys Tyr Gln Pro Arg Cys
 65                  70                  75

<210> SEQ ID NO 22
<211> LENGTH: 78
<212> TYPE: PRT
<213> ORGANISM: Artificial Sequence

```
<220> FEATURE:
<223> OTHER INFORMATION: KD409

<400> SEQUENCE: 22

Cys Ala Lys Asp Lys Gly Asp Lys Tyr Asp Gly His Lys His Lys Thr
1               5                   10                  15

Asn Arg Gly Asp Lys Cys Gln Thr Trp Ala Lys Asn Arg Pro His Phe
            20                  25                  30

His Gly His Arg Phe Glu Val Gly His Glu His Lys Ile Arg Lys Asn
        35                  40                  45

Tyr Cys Arg Asn Pro Asp Asp Gln Asp Lys Pro Trp Cys Phe Thr His
    50                  55                  60

Gly Tyr Arg Asn Gln Asp Glu Leu Cys Asp Gly Pro Arg Cys
65                  70                  75

<210> SEQ ID NO 23
<211> LENGTH: 78
<212> TYPE: PRT
<213> ORGANISM: Artificial Sequence
<220> FEATURE:
<223> OTHER INFORMATION: KD413

<400> SEQUENCE: 23

Cys Ala Lys Ala Glu Gly Thr Gly Tyr Asp Gly His Glu His Lys Thr
1               5                   10                  15

His Lys Gly Ile Arg Cys Gln Asn Trp Tyr Lys Ser Lys Pro His Tyr
            20                  25                  30

His Gly His Gln Phe Arg Asp Gly Asp Lys Ile Lys Asn Lys Lys Asn
        35                  40                  45

Tyr Cys Arg Asn Pro Asp Pro Arg Ala Gly Pro Trp Cys Phe Thr His
    50                  55                  60

Gly Asn Arg Asn Arg Tyr Glu Leu Cys Asn Gln Pro Arg Cys
65                  70                  75

<210> SEQ ID NO 24
<211> LENGTH: 78
<212> TYPE: PRT
<213> ORGANISM: Artificial Sequence
<220> FEATURE:
<223> OTHER INFORMATION: KD415

<400> SEQUENCE: 24

Cys Thr Arg Ser Lys Gly Asp Glu Tyr Asp Gly His Lys His Lys Thr
1               5                   10                  15

Asn Arg Gly Leu Arg Cys Gln His Trp Pro Gly Thr Lys Pro His Phe
            20                  25                  30

His Gly Asp Lys Ile Lys Asp Arg His Gly Phe Arg Leu Lys Lys Asn
        35                  40                  45

Tyr Cys Arg Asn Pro Asp Pro Gln Asp Gln Pro Trp Cys Phe Thr Asn
    50                  55                  60

Arg His Gln His Lys Asn Glu Leu Cys Asn Gln Pro Arg Cys
65                  70                  75

<210> SEQ ID NO 25
<211> LENGTH: 78
<212> TYPE: PRT
<213> ORGANISM: Artificial Sequence
<220> FEATURE:
<223> OTHER INFORMATION: KD421

<400> SEQUENCE: 25
```

Cys Ala Gly Ala Glu Gly Asn Glu Tyr Asp Gly Asp Lys Tyr Lys Thr
1               5                   10                  15

His Lys Gly Tyr Arg Cys Gln Arg Trp Asp Lys Ser Arg Pro His Asn
            20                  25                  30

His Gly Asn Lys Asp Arg His Gln His Glu Asn Lys Val Gly Lys Asn
        35                  40                  45

Tyr Cys Arg Asn Pro Asp Asn Glu Ala Glu Pro Trp Cys Phe Thr Asp
    50                  55                  60

Gln His Lys His Gly Asn Glu Leu Cys Asp Arg Pro Arg Cys
65                  70                  75

<210> SEQ ID NO 26
<211> LENGTH: 78
<212> TYPE: PRT
<213> ORGANISM: Artificial Sequence
<220> FEATURE:
<223> OTHER INFORMATION: KD437

<400> SEQUENCE: 26

Cys Ala Lys Ser Arg Gly Tyr Lys Tyr Asp Gly Asn Arg Tyr Lys Thr
1               5                   10                  15

Asn Lys Gly Asp Lys Cys Gln Ala Trp Thr Lys Thr Lys Pro His Asp
            20                  25                  30

His Gly His Arg His Gly His Gly Asp Arg Phe Arg Asn Arg Lys Asn
        35                  40                  45

Tyr Cys Arg Asn Pro Asp His Glu Ser Lys Pro Trp Cys Phe Thr Tyr
    50                  55                  60

Arg Asp Arg Tyr Arg His Glu Leu Cys Asn Arg Pro Arg Cys
65                  70                  75

<210> SEQ ID NO 27
<211> LENGTH: 78
<212> TYPE: PRT
<213> ORGANISM: Artificial Sequence
<220> FEATURE:
<223> OTHER INFORMATION: KD444

<400> SEQUENCE: 27

Cys His Arg Thr Arg Gly Asp Lys Tyr Asp Gly Tyr Glu His Lys Thr
1               5                   10                  15

His Gly Gly His Arg Cys Gln His Trp Thr Glu Pro Lys Pro His Tyr
            20                  25                  30

His Gly His Arg Asp Arg Asn Lys Asn Gly Ile Arg Asp Lys Lys Asn
        35                  40                  45

Tyr Cys Arg Asn Pro Asp Pro Arg Ala Glu Pro Trp Cys Phe Thr Asn
    50                  55                  60

Lys Asn Gly Asp Lys His Glu Leu Cys Asp Lys Pro Arg Cys
65                  70                  75

<210> SEQ ID NO 28
<211> LENGTH: 78
<212> TYPE: PRT
<213> ORGANISM: Artificial Sequence
<220> FEATURE:
<223> OTHER INFORMATION: KD445

<400> SEQUENCE: 28

Cys His Glu Thr Lys Gly His Lys Tyr Asp Gly His Arg Leu Arg Thr
1               5                   10                  15

Asn Lys Gly Asp Arg Cys Gln Pro Trp Thr Lys Asp Lys Pro His His
            20                  25                  30

His Gly Phe Arg Asp Gln Tyr Gln Val Arg Tyr Lys Leu Lys Lys Asn
            35                  40                  45

Tyr Cys Arg Asn Pro Asp Asp Gln Asn Lys Pro Trp Cys Phe Thr Asp
         50                  55                  60

Gly Asn Gln His Glu His Glu Leu Cys Asn Gly Pro Arg Cys
65                  70                  75

<210> SEQ ID NO 29
<211> LENGTH: 78
<212> TYPE: PRT
<213> ORGANISM: Artificial Sequence
<220> FEATURE:
<223> OTHER INFORMATION: KD449

<400> SEQUENCE: 29

Cys Asp Arg Tyr Lys Gly Tyr Arg Tyr Asp Gly His Arg Tyr Lys Thr
1               5                   10                  15

His Lys Gly His Lys Cys Gln His Trp Asp Glu Asp Gln Pro His Asn
            20                  25                  30

His Gly His Gly His Arg Ile Lys Asp Gly Phe Glu Val Arg Lys Asn
            35                  40                  45

Tyr Cys Arg Asn Pro Asp Ala Gly Thr Lys Pro Trp Cys Phe Thr Asp
         50                  55                  60

Lys Asp Gln Asn Arg His Glu Leu Cys Tyr Lys Pro Arg Cys
65                  70                  75

<210> SEQ ID NO 30
<211> LENGTH: 78
<212> TYPE: PRT
<213> ORGANISM: Artificial Sequence
<220> FEATURE:
<223> OTHER INFORMATION: KD456

<400> SEQUENCE: 30

Cys Asp Lys Asn Arg Gly Asn Gly Tyr Asp Gly Asn Glu Ile Gln Thr
1               5                   10                  15

Asp Gly Gly Val Gln Cys Gln His Trp Thr Lys Thr Lys Pro His His
            20                  25                  30

His Gly Leu Lys Leu Gln His Glu His Arg Val Lys His Glu Lys Asn
            35                  40                  45

Tyr Cys Arg Asn Pro Asp Ala Arg Thr Gln Pro Trp Cys Phe Thr Asp
         50                  55                  60

Lys His Gln His Lys Asp Glu Leu Cys Ile Glu Pro Arg Cys
65                  70                  75

<210> SEQ ID NO 31
<211> LENGTH: 78
<212> TYPE: PRT
<213> ORGANISM: Artificial Sequence
<220> FEATURE:
<223> OTHER INFORMATION: KD459

<400> SEQUENCE: 31

Cys Ser Arg Tyr Arg Gly His Lys Tyr Asp Gly Tyr Lys His Arg Thr
1               5                   10                  15

Tyr Lys Gly Tyr Gln Cys Gln Ser Trp Thr Lys Asp Lys Pro His His
            20                  25                  30

His Gly Ile Arg His Arg Asn Lys Ile Arg Asp Arg Phe Gly Lys Asn
            35                  40                  45

Tyr Cys Arg Asn Pro Asp Thr Gln Asn Gln Pro Trp Cys Phe Thr Tyr

```
                 50                  55                  60
Gly Asp Glu Tyr Arg Tyr Glu Leu Cys Asn Lys Pro Arg Cys
65                  70                  75

<210> SEQ ID NO 32
<211> LENGTH: 78
<212> TYPE: PRT
<213> ORGANISM: Artificial Sequence
<220> FEATURE:
<223> OTHER INFORMATION: CONSENSUS

<400> SEQUENCE: 32

Cys Ala Arg Asp Lys Gly Asp Lys Tyr Asp Gly His Lys His Lys Thr
1               5                   10                  15

His Lys Gly His Lys Cys Gln His Trp Thr Lys Asp Lys Pro His His
                20                  25                  30

His Gly His Arg His Arg Asp Lys His Arg Phe Lys Leu Lys Lys Asn
            35                  40                  45

Tyr Cys Arg Asn Pro Asp Ala Arg Ala Lys Pro Trp Cys Phe Thr Asp
        50                  55                  60

Lys Asp Arg His Arg His Glu Leu Cys Asn Gln Pro Arg Cys
65                  70                  75

<210> SEQ ID NO 33
<211> LENGTH: 78
<212> TYPE: PRT
<213> ORGANISM: Artificial Sequence
<220> FEATURE:
<223> OTHER INFORMATION: KD502

<400> SEQUENCE: 33

Cys Ala Glu Asp Lys Gly Ala Arg Tyr Asp Gly Tyr Gln Tyr Arg Thr
1               5                   10                  15

His Lys Gly Ile Lys Cys Gln Pro Trp Tyr Gln His Glu Pro His Tyr
                20                  25                  30

His Gly His Lys Asp Lys Ile Arg His Lys Asn Arg Asn Lys Lys Asn
            35                  40                  45

Tyr Cys Arg Asn Pro Asp Ala Gly Asp Arg Pro Trp Cys Phe Thr His
        50                  55                  60

Arg Asp Lys Tyr Glu His Glu Leu Cys Asn Arg Pro Arg Cys
65                  70                  75

<210> SEQ ID NO 34
<211> LENGTH: 78
<212> TYPE: PRT
<213> ORGANISM: Artificial Sequence
<220> FEATURE:
<223> OTHER INFORMATION: KD503

<400> SEQUENCE: 34

Cys Thr Gln Thr Lys Gly His Arg Tyr Asp Gly Tyr Lys Tyr Glu Thr
1               5                   10                  15

Asn Trp Gly His Gln Cys Gln Ala Trp Thr Lys His Lys Pro His Leu
                20                  25                  30

His Gly Asn Gly His Arg Asn Arg His Lys Val Gly His Glu Lys Asn
            35                  40                  45

Tyr Cys Arg Asn Pro Asp His Arg Asp Gly Pro Trp Cys Phe Thr Asn
        50                  55                  60

Gln Tyr Glu Asn Glu Asn Glu Leu Cys His Gln Pro Arg Cys
65                  70                  75
```

<210> SEQ ID NO 35
<211> LENGTH: 78
<212> TYPE: PRT
<213> ORGANISM: Artificial Sequence
<220> FEATURE:
<223> OTHER INFORMATION: KD505

<400> SEQUENCE: 35

```
Cys Pro Glu Asp Gln Gly Asp Glu Tyr Asp Gly His Glu His Lys Thr
 1               5                  10                  15

His Arg Gly Asn Arg Cys Gln Ser Trp Tyr Arg Pro Lys Pro His Asn
            20                  25                  30

His Gly His Arg Ile Lys Asp Arg Tyr Lys Tyr Lys Val Lys Lys Asn
        35                  40                  45

Tyr Cys Arg Asn Pro Asp Thr Gln Ala Arg Pro Trp Cys Phe Thr Asn
 50                  55                  60

Arg His Arg Asp Glu His Glu Leu Cys Asp Gln Pro Arg Cys
 65                  70                  75
```

<210> SEQ ID NO 36
<211> LENGTH: 78
<212> TYPE: PRT
<213> ORGANISM: Artificial Sequence
<220> FEATURE:
<223> OTHER INFORMATION: KD506

<400> SEQUENCE: 36

```
Cys Pro Glu Asp Arg Gly His Glu Tyr Asp Gly Asp Gly Asp Lys Thr
 1               5                  10                  15

Asn Arg Gly His Gly Cys Gln Tyr Trp Asp Gln Asn Lys Pro His His
            20                  25                  30

His Gly His Arg Asp Lys Asp Lys Phe Lys His Arg Ile Lys Lys Asn
        35                  40                  45

Tyr Cys Arg Asn Pro Asp Tyr Glu Thr Gly Pro Trp Cys Phe Thr Asn
 50                  55                  60

Arg Tyr Arg Asn Lys Asn Glu Leu Cys His Glu Pro Arg Cys
 65                  70                  75
```

<210> SEQ ID NO 37
<211> LENGTH: 78
<212> TYPE: PRT
<213> ORGANISM: Artificial Sequence
<220> FEATURE:
<223> OTHER INFORMATION: KD509

<400> SEQUENCE: 37

```
Cys Ala Gln Ser Lys Gly Tyr Arg Tyr Asp Gly Asp Lys Asp Lys Thr
 1               5                  10                  15

Asn Lys Gly His Lys Cys Gln Asp Trp Ala Gln Asn Lys Pro His Val
            20                  25                  30

His Gly His Arg His Glu Asp Arg His Gln Val Lys Ser Arg Lys Asn
        35                  40                  45

Tyr Cys Arg Asn Pro Asp Ala Arg Ala Arg Pro Trp Cys Phe Thr Asn
 50                  55                  60

Gln Val Arg Tyr Arg Asn Glu Leu Cys Tyr Lys Pro Arg Cys
 65                  70                  75
```

<210> SEQ ID NO 38
<211> LENGTH: 78
<212> TYPE: PRT
<213> ORGANISM: Artificial Sequence

```
<220> FEATURE:
<223> OTHER INFORMATION: KD537

<400> SEQUENCE: 38

Cys Thr Arg Thr Lys Gly Ala Lys Tyr Asp Gly Tyr Lys His Arg Thr
1               5                   10                  15

His Glu Gly Asn Lys Cys Gln Ser Trp Asn Lys Ala Arg Pro His Leu
            20                  25                  30

His Gly Asp Arg Leu Gly Asn Lys Tyr Glu His Lys Ala Arg Lys Asn
        35                  40                  45

Tyr Cys Arg Asn Pro Asp Asn Arg Ala Glu Pro Trp Cys Phe Thr Asp
    50                  55                  60

Lys Asn Gln Asn Gln His Glu Leu Cys Tyr Gly Pro Arg Cys
65                  70                  75

<210> SEQ ID NO 39
<211> LENGTH: 78
<212> TYPE: PRT
<213> ORGANISM: Artificial Sequence
<220> FEATURE:
<223> OTHER INFORMATION: KD542

<400> SEQUENCE: 39

Cys Asn Arg Ala Gly Gly His Lys Tyr Asp Gly Asp Arg Tyr Arg Thr
1               5                   10                  15

His Arg Gly Asp Gly Cys Gln Asn Trp Ala Lys Thr Lys Pro His His
            20                  25                  30

His Gly Ile Gly His Arg Asp Lys Ile Arg Asp Lys Tyr Arg Lys Asn
        35                  40                  45

Tyr Cys Arg Asn Pro Asp Ala Lys Asn Gly Pro Trp Cys Phe Thr Asn
    50                  55                  60

Arg Asn Gly Asp Lys Asn Glu Leu Cys Ile Gln Pro Arg Cys
65                  70                  75

<210> SEQ ID NO 40
<211> LENGTH: 78
<212> TYPE: PRT
<213> ORGANISM: Artificial Sequence
<220> FEATURE:
<223> OTHER INFORMATION: KD548

<400> SEQUENCE: 40

Cys His Gln Thr Gln Gly Pro Lys Tyr Asp Gly Asn Lys Asp Lys Thr
1               5                   10                  15

His Lys Gly His Lys Cys Gln Ser Trp Thr Lys Asn Arg Pro His His
            20                  25                  30

His Gly Asn Lys Ile Glu Asn Glu Asp Glu Asn Arg Phe Gln Lys Asn
        35                  40                  45

Tyr Cys Arg Asn Pro Asp Asn Lys His Glu Pro Trp Cys Phe Thr His
    50                  55                  60

Gly His Arg Asp Lys His Glu Leu Cys His Glu Pro Arg Cys
65                  70                  75

<210> SEQ ID NO 41
<211> LENGTH: 78
<212> TYPE: PRT
<213> ORGANISM: Artificial Sequence
<220> FEATURE:
<223> OTHER INFORMATION: KD555

<400> SEQUENCE: 41
```

```
Cys Asp Gly Ala Gln Gly Asn Gly Tyr Asp Gly Asn Lys His Lys Thr
1               5                   10                  15

His Arg Gly Asn Lys Cys Gln Ala Trp Pro Lys His Gly Pro His Tyr
            20                  25                  30

His Gly Asn Gly Asp Gln Asp Gly His Arg Asn Lys His Lys Lys Asn
        35                  40                  45

Tyr Cys Arg Asn Pro Asp Thr Arg Ser Arg Pro Trp Cys Phe Thr Asp
50                  55                  60

Gln Asn Gly His Lys Asp Glu Leu Cys His Gly Pro Arg Cys
65                  70                  75
```

<210> SEQ ID NO 42
<211> LENGTH: 78
<212> TYPE: PRT
<213> ORGANISM: Artificial Sequence
<220> FEATURE:
<223> OTHER INFORMATION: KD559

<400> SEQUENCE: 42

```
Cys Asn Lys His Lys Gly Pro Arg Tyr Asp Gly His Lys Asp Lys Thr
1               5                   10                  15

Asn Lys Gly His Glu Cys Gln Pro Trp Asn Arg Pro Lys Pro His Asp
            20                  25                  30

His Gly His Lys His Gln Phe Lys Asp Lys Asn Arg Leu Glu Lys Asn
        35                  40                  45

Tyr Cys Arg Asn Pro Asp His Arg Asn Glu Pro Trp Cys Phe Thr His
50                  55                  60

Gly Asn Arg Asn Gly Asp Glu Leu Cys Phe Arg Pro Arg Cys
65                  70                  75
```

<210> SEQ ID NO 43
<211> LENGTH: 78
<212> TYPE: PRT
<213> ORGANISM: Artificial Sequence
<220> FEATURE:
<223> OTHER INFORMATION: CONSENSUS

<400> SEQUENCE: 43

```
Cys Thr Glu Asp Lys Gly His Arg Tyr Asp Gly Asp Lys His Lys Thr
1               5                   10                  15

His Lys Gly His Lys Cys Gln Ser Trp Asn Lys His Lys Pro His His
            20                  25                  30

His Gly His Arg His Lys Asp Arg His Lys Asn Lys His Lys Lys Asn
        35                  40                  45

Tyr Cys Arg Asn Pro Asp His Arg Ala Arg Pro Trp Cys Phe Thr Asn
50                  55                  60

Arg Asn Arg Asn Glu Asn Glu Leu Cys His Arg Pro Arg Cys
65                  70                  75
```

<210> SEQ ID NO 44
<211> LENGTH: 78
<212> TYPE: PRT
<213> ORGANISM: Artificial Sequence
<220> FEATURE:
<223> OTHER INFORMATION: KDT01

<400> SEQUENCE: 44

```
Cys Tyr Glu Asp Lys Gly Pro Gln Tyr Asp Gly Asp Glu Tyr Gly Thr
1               5                   10                  15

His Lys Gly His Arg Cys Gln Asn Trp Asp Glu Asn Arg Pro His Pro
            20                  25                  30
```

His Gly Ile Gly His Gln His Lys His Gln Val Lys Asp Gly Lys Asn
             35                  40                  45

Tyr Cys Arg Asn Pro Asp Asp Glu Thr Glu Pro Trp Cys Phe Thr His
     50                  55                  60

Lys Asp Lys Tyr Gly His Glu Leu Cys Asn Arg Pro Arg Cys
 65                  70                  75

<210> SEQ ID NO 45
<211> LENGTH: 78
<212> TYPE: PRT
<213> ORGANISM: Artificial Sequence
<220> FEATURE:
<223> OTHER INFORMATION: KDT02

<400> SEQUENCE: 45

Cys Ala Gln Asp Gly Gly Pro Gly Tyr Asp Gly Asp Lys His Gly Thr
 1               5                  10                  15

His Gly Gly His Glu Cys Gln Asp Trp Thr Lys Asp Gly Pro His Ile
             20                  25                  30

His Gly Phe Arg Asp Gln Phe Arg Asp Glu Asp Gln His Gly Lys Asn
             35                  40                  45

Tyr Cys Arg Asn Pro Asp Ser Gln His Gly Pro Trp Cys Phe Thr Asn
     50                  55                  60

Glu Asp Glu His Arg Asn Glu Leu Cys His Pro Arg Cys
 65                  70                  75

<210> SEQ ID NO 46
<211> LENGTH: 78
<212> TYPE: PRT
<213> ORGANISM: Artificial Sequence
<220> FEATURE:
<223> OTHER INFORMATION: KDT08

<400> SEQUENCE: 46

Cys Pro Lys Ser Gly Gly Asn Gly Tyr Asp Gly Tyr Lys His Gly Thr
 1               5                  10                  15

Asn Glu Gly Leu Gln Cys Gln Asn Trp Asp Arg Ala Lys Pro His Asp
             20                  25                  30

His Gly Ile Glu Val Gln Asn Glu Tyr Gly Asp Arg His Glu Lys Asn
             35                  40                  45

Asn Cys Arg Asn Pro Asp Asp Lys Thr Arg Pro Trp Cys Phe Thr His
     50                  55                  60

Lys Asp Arg Tyr Arg Asn Glu Leu Cys Tyr Gln Pro Arg Cys
 65                  70                  75

<210> SEQ ID NO 47
<211> LENGTH: 78
<212> TYPE: PRT
<213> ORGANISM: Artificial Sequence
<220> FEATURE:
<223> OTHER INFORMATION: KDT26

<400> SEQUENCE: 47

Cys Pro Arg Asp Gln Gly Asn Gln Tyr Asp Gly Phe Arg Tyr Gly Thr
 1               5                  10                  15

Tyr Arg Gly His Arg Cys Gln His Trp Thr Asp Glu Pro His Phe
             20                  25                  30

His Gly Phe Gly His Gln His Lys Tyr Thr Tyr Arg His Lys Lys Asn
             35                  40                  45

Tyr Cys Arg Asn Pro Asp Ala Arg Pro Arg Pro Trp Cys Phe Thr His

```
                50              55              60
Arg Tyr Gln Asn Arg Asn Glu Leu Cys His Gln Pro Arg Cys
65                      70              75

<210> SEQ ID NO 48
<211> LENGTH: 78
<212> TYPE: PRT
<213> ORGANISM: Artificial Sequence
<220> FEATURE:
<223> OTHER INFORMATION: CONSENSUS

<400> SEQUENCE: 48

Cys Asp Glu Asp Lys Gly Pro Gly Tyr Asp Gly Lys His Gly Thr
1               5                   10                  15

His Lys Gly His Glu Cys Gln Asp Trp Thr Lys Asp Arg Pro His Asp
                20                  25                  30

His Gly His Gly Asp Gln His Lys Tyr Glu Asp Lys His Gly Lys Asn
            35                  40                  45

Tyr Cys Arg Asn Pro Asp Asp Glu Thr Arg Pro Trp Cys Phe Thr His
    50                  55                  60

Lys Asp Arg Asn Arg Asn Glu Leu Cys Asp Gln Pro Arg Cys
65                      70              75

<210> SEQ ID NO 49
<211> LENGTH: 78
<212> TYPE: PRT
<213> ORGANISM: Artificial Sequence
<220> FEATURE:
<223> OTHER INFORMATION: Kringle domain

<400> SEQUENCE: 49

Cys Met His Cys Ser Gly Glu Asn Tyr Asp Gly Lys Ile Ser Lys Thr
1               5                   10                  15

Met Ser Gly Leu Glu Cys Gln Ala Trp Asp Ser Gln Ser Pro His Ala
                20                  25                  30

His Gly Tyr Ile Pro Ser Lys Phe Pro Asn Lys Asn Leu Lys Lys Asn
            35                  40                  45

Tyr Cys Arg Asn Pro Asp Arg Glu Leu Arg Pro Trp Cys Phe Thr Thr
    50                  55                  60

Asp Pro Asn Lys Arg Trp Glu Leu Cys Asp Ile Pro Arg Cys
65                      70              75

<210> SEQ ID NO 50
<211> LENGTH: 234
<212> TYPE: DNA
<213> ORGANISM: Artificial Sequence
<220> FEATURE:
<223> OTHER INFORMATION: gene

<400> SEQUENCE: 50
tgtatgcatt gcagtggaga aaactatgac ggcaaaattt ccaagaccat gtctggactg      60
gaatgccagg cctgggactc tcagagccca cacgctcatg gatacattcc ttccaaattt     120
ccaaacaaga acctgaagaa gaattactgt cgtaaccccg atagggagct gcggccttgg     180
tgtttcacca ccgaccccaa caagcgctgg gaactttgcg acatcccccg ctgc           234
```